(12) United States Patent
Hackett et al.

(10) Patent No.: US 11,066,451 B2
(45) Date of Patent: Jul. 20, 2021

(54) METHODS FOR PURIFYING CLOSTRIDIAL NEUROTOXIN

(71) Applicant: Ipsen BioPharm Limited, Wrexham (GB)

(72) Inventors: Gavin Stephen Hackett, Milton Keynes (GB); Shilpa Palan, Oxfordshire (GB); Dina Brady Anderson, Abingdon (GB)

(73) Assignee: IPSEN BIOPHARM LIMITED, Wrexham (GB)

(*) Notice: Subject to any disclaimer, the term of this patent is extended or adjusted under 35 U.S.C. 154(b) by 250 days.

(21) Appl. No.: 15/765,427

(22) PCT Filed: Sep. 27, 2016

(86) PCT No.: PCT/EP2016/072986
§ 371 (c)(1),
(2) Date: Apr. 2, 2018

(87) PCT Pub. No.: WO2017/055274
PCT Pub. Date: Apr. 6, 2017

(65) Prior Publication Data
US 2019/0100564 A1    Apr. 4, 2019

(30) Foreign Application Priority Data
Oct. 2, 2015 (GB) .................................. 1517450

(51) Int. Cl.
*C07K 14/33* (2006.01)
*C12N 9/52* (2006.01)
*C07K 1/18* (2006.01)

(52) U.S. Cl.
CPC ............. *C07K 14/33* (2013.01); *C12N 9/52* (2013.01); *C12Y 304/24068* (2013.01); *C12Y 304/24069* (2013.01)

(58) Field of Classification Search
None
See application file for complete search history.

(56) References Cited

U.S. PATENT DOCUMENTS

2011/0092682 A1    4/2011    Ruegg

FOREIGN PATENT DOCUMENTS

| WO | 2010/127258 A1 | 11/2010 |
| WO | 2011050072 | 4/2011 |
| WO | 2013091895 | 6/2013 |
| WO | 2015004461 | 1/2015 |
| WO | 2015/097087 A1 | 7/2015 |
| WO | WO 2015/166242 A1 * | 11/2015 |
| WO | 2016/110662 A1 | 7/2016 |

OTHER PUBLICATIONS

International Search Report dated Feb. 15, 2017, in PCT/EP2016/072986.
European Search Report and Opinion dated Mar. 23, 2020, in EP Application No. 19198429.3.

* cited by examiner

*Primary Examiner* — Sarvamangala Devi
(74) *Attorney, Agent, or Firm* — Gene J. Yao; Barnes & Thornburg LLP

(57) ABSTRACT

A method for purifying a clostridial neurotoxin comprising contacting a cation exchange resin with a composition comprising a clostridial neurotoxin, wherein the contacting step is performed at at least pH 7.3, wherein the step of contacting a cation exchange resin with a composition comprising said clostridial neurotoxin occurs prior to conversion of the clostridial neurotoxin from a single chain form into a dichain form. Also provided are uses of a buffer having a pH value that is −1 pH unit or higher than the calculated pi of a clostridial neurotoxin, purification intermediates and clostridial neurotoxins obtainable by the invention, wherein the clostridial neurotoxin is in a single chain form.

16 Claims, 25 Drawing Sheets
Specification includes a Sequence Listing.

| Panel | Loading Buffer | Elution Gradient |
|---|---|---|
| A | Citrate phosphate buffer, pH 6.0 | pH 6.0 to pH 7.5 |
| B | 50mM Bis-Tris methane, pH 6.0 | 0 to 1M NaCl |
| C | 50mM HEPES, pH 7.5 | 0 to 1M NaCl |
| D | 50mM Bis-Tris methane, pH 7.5 | 0 to 1M NaCl |
| E | Tris, pH 8.0 | 0 to 1M NaCl |
| F | 50mM Bis-Tris propane, pH 8.0 | 0 to 1M NaCl |

FIGURE 3

(SEQ ID No. 1)
ATGCCATTCGTCAACAAGCAATTCAACTACAAAGACCCAGTCAACGGCGTCGACATCGCATACATCAAGATTCCG
AACGCCGGTCAAATGCAGCCGGTTAAGGCTTTTAAGATCCACAACAAGATTTGGGTTATCCCGGAGCGTGACACC
TTCACGAACCCGGAAGAAGGCGATCTGAACCCGCCACCGGAAGCGAAGCAAGTCCCTGTCAGCTACTACGATTCG
ACGTACCTGAGCACGGATAACGAAAAAGATAACTACCTGAAAGGTGTGACCAAGCTGTTCGAACGTATCTACAGC
ACGGATCTGGGTCGCATGCTGCTGACTAGCATTGTTCGCGGTATCCCGTTCTGGGTGGTAGCACGATTGACACC
GAACTGAAGGTTATCGACACTAACTGCATTAACGTTATTCAACCGGATGGTAGCTATCGTAGCGAAGAGCTGAAT
CTGGTCATCATTGGCCCGAGCGCAGACATTATCCAATTCGAGTGCAAGAGCTTTGGTCACGAGGTTCTGAATCTG
ACCCGCAATGGCTATGGTAGCACCCAGTACATTCGTTTTTCGCCGGATTTTACCTTCGGCTTTGAAGAGAGCCTG
GAGGTTGATACCAATCCGTTGCTGGGTGCGGGCAAATTCGCTACCGATCCGGCTGTCACGCTGGCCCATcAACTG
ATCtACGCAGGCCACCGCCTGTACGGCATTGCCATCAACCCAAACCGTGTGTTCAAGGTTAATACGAATGCATAC
TACGAGATGAGCGGCCTGGAAGTCAGCTTCGAAGAACTGCGCACCTTCGGTGGCCATGACGCTAAATTCATTGAC
AGCTTGCAAGAGAATGAGTTCCGTCTGTACTACTATAACAAATTCAAAGACATTGCAAGCACGTTGAACAAGGCC
AAAAGCATCGTTGGTACTACCGCGTCGTTGCAGTATATGAAGAATGTGTTTAAAGAGAAGTACCTGCTGTCCGAG
GATACCTCCGGCAAGTTTAGCGTTGATAAGCTGAAGTTTGACAAACTGTACAAGATGCTGACCGAGATTTACACC
GAGGACAACTTTGTGAAATTCTTCAAAGTGTTGAATCGTAAAACCTATCTGAATTTTGACAAAGCGGTTTTCAAG
ATTAACATCGTGCCGAAGGTGAACTACACCATCTATGACGGTTTTAACCTGCGTAACACCAACCTGGCGGCGAAC
TTTAACGGTCAGAATACGGAAATCAACAACATGAATTTCACGAAGTTGAAGAACTTCACGGGTCTGTTCGAGTTC
TATAAGCTGCTGTGCGTGCGCGGTATCATCACCAGCAAAACCAAAAGCCTGGACAAAGGCTACAACAAGGCGCTG
AATGACCTGTGCATTAAGGTAAACAATTGGGATCTGTTCTTTTCGCCATCCGAAGATAATTTTACCAACGACCTG
AACAAGGGTGAAGAAATCACCAGCGATACGAATATTGAAGCAGCGGAAGAGAATATCAGCCTGGATCTGATCCAG
CAGTACTATCTGACCTTTAACTTCGACAATGAACCGGAGAACATTAGCATTGAGAATCTGAGCAGCGACATTATC
GGTCAGCTGGAACTGATGCCGAATATCGAACGTTTCCCGAACGGCAAAAAGTACGAGCTGGACAAGTACACTATG
TTCCATTACCTGCGTGCACAGgAGTTTGAACACGGTAAAAGCCGTATCGCGCTGACCAACAGCGTTAACGAGGCC
CTGCTGAACCCGAGCCGTGTCTATACCTTCTTCAGCAGCGACTATGTTAAGAAAGTGAACAAAGCCACTGAGGCC
GCGATGTTCCTGGGCTGGGTGGAACAGCTGGTATATGACTTCACGGACGAGACGAGCGAAGTGAGCACTACCGAC
AAAATTGCTGATATTACCATCATTATCCCGTATATTGGTCCGGCACTGAACATTGGCAACATGCTGTACAAAGAC
GATTTTGTGGGTGCCCTGATCTTCTCCGGTGCCGTGATTCTGCTGGAGTTCATTCCGGAGATTGCGATCCCGGTG
TTGGGTACCTTCGCGCTGGTGTCCTACATCGCGAATAAGGTTCTGACGGTTCAGACCATCGATAACGCGCTGTCG
AAACGTAATGAAAAATGGGACGAGGTTTACAAATACATTGTTACGAATTGGCTGGCGAAAGTCAATACCCAGATC
GACCTGATCCGTAAGAAAATGAAAGAGGCGCTGGAGAATCAGGCGGAGGCCACCAAAGCAATTATCAACTACCAA
TACAACCAGTACACGGAAGAAGAGAAGAATAACATTAACTTCAATATCGATGATTtGAGCAGCAAGCTGAATGAA
TCTATCAACAAAGCGATGATCAATATCAACAAGTTTTTGAATCAGTGTAGCGTTTCGTACCTGATGAATAGCATG
ATTCCGTATGGCGTCAAACGTCTGGAGGACTTCGACGCCAGCCTGAAAGATGCGTTGCTGAAATACATTTACGAC
AATCGTGGTACGCTGATTGGCCAAGTTGACCGCTTGAAAGACAAAGTTAACAATACCCTGAGCACCGACATCCCA
TTTCAACTGAGCAAGTATGTTGATAATCAACGTCTGTTGAGCACTTTCACCGAGTATATCAAAACATCATCAAT
ACTAGCATTCTGAACCTGCGTTACGAGAGCAAGCATCTGATTGATCTGAGCCGTTATGCTAGCAAGATCAACATC
GGTAGCAAGGTCAATTTTGACCCGATCGATAAGAACCAGATCCAGCTGTTTAATCTGGAATCGAGCAAAATTGAG
GTTATCCTGAAAAAGGCCATTGTCTACAACTCCATGTACGAGAATTTCTCCACCAGCTTCTGGATTCGCATCCCG
AAATACTTCAACAAGATTAGCCTGAACAACGAGTATACTATCATCAACTGTATGGAGAACAACAGCGGTTGGAAG
GTGTCTCTGAACTATGGTGAGATCATTTGGACCTTGCAGGACACCAAAGAGATCAAGCAGCGCGTCGTGTTCAAG
TACTCTCAAATGATCAACATTTCCGATTACATTAATCGTTGGATCTTCGTGACCATTACGAATAACCGTCTGAAT
AAGAGCAAGATTTACATCAATGGTCGCTTGATCGATCAGAAACCGATTAGCAACCTGGGTAATATCCACGCAAGC
AACAAGATTATGTTCAAATTGGACGGTTGCCGCGATACCCATCGTTATATCTGGATCAAGTATTTCAACCTGTTT
GATAAAGAACTGAATGAGAAGGAGATCAAAGATTTGTATGACAACCAATCTAACAGCGGCATTTTGAAGGACTTC
TGGGGCGATTATCTGCAATACGATAAGCCGTACTATATGCTGAACCTGTATGATCCGAACAAATATGTGGATGTC
AATAATGTGGGTATTCGTGGTTACATGTATTTGAAGGGTCCGCGTGGCAGCGTTATGACGACCAACATTTACCTG
AACTCTAGCCTGTACCGTGGTACGAAATTCATCATTAAGAAATATGCCAGCGGCAACAAAGATAACATTGTGCGT
AATAACGATCGTGTCTACATCAACGTGGTCGTGAAGAATAAAGAGTACCGTCTGGCGACCAACGCTTCGCAGGCG
GGTGTTGAGAAATTCTGAGCGCGTTGGAGATCCCTGATGTCGGTAATCTGAGCCAAGTCGTGGTTATGAAGAGC
AAGAACGACAAGGGTATCACTAACAAGTGCAAGATGAACCTGCAAGACAACAATGGTAACGACATCGGCTTTATT
GGTTTCCACCAGTTCAACAATATTGCTAAACTGGTAGCGAGCAATTGGTACAATCGTCAGATTGAGCGCAGCAGC
cGTACTTTGGGCTGTAGCTGGGAGTTTATCCCGGTCGATGATGGTTGGGCGAACGTCCGCTG

FIGURE 4

(SEQ ID No. 2)
MPFVNKQFNYKDPVNGVDIAYIKIPNAGQMQPVKAFKIHNKIWVIPERDTFTNPEEGDLNPPPEAKQVPVSYYDS
TYLSTDNEKDNYLKGVTKLFERIYSTDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESLEVDTNPLLGAGKFATDPAVTLAHQL
IYAGHRLYGIAINPNRVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKVLNRKTYLNFDKAVFK
INIVPKVNYTIYDGFNLRNTNLAANFNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQQYYLTFNFDNEPENISIENLSSDII
GQLELMPNIERFPNGKKYELDKYTMFHYLRAQEFEHGKSRIALTNSVNEALLNPSRVYTFFSSDYVKKVNKATEA
AMFLGWVEQLVYDFTDETSEVSTTDKIADITIIIPYIGPALNIGNMLYKDDFVGALIFSGAVILLEFIPEIAIPV
LGTFALVSYIANKVLTVQTIDNALSKRNEKWDEVYKYIVTNWLAKVNTQIDLIRKKMKEALENQAEATKAIINYQ
YNQYTEEEKNNINFNIDDLSSKLNESINKAMININKFLNQCSVSYLMNSMIPYGVKRLEDFDASLKDALLKYIYD
NRGTLIGQVDRLKDKVNNTLSTDIPFQLSKYVDNQRLLSTFTEYIKNIINTSILNLRYESKHLIDLSRYASKINI
GSKVNFDPIDKNQIQLFNLESSKIEVILKKAIVYNSMYENFSTSFWIRIPKYFNKISLNNEYTIINCMENNSGWK
VSLNYGEIIWTLQDTKEIKQRVVFKYSQMINISDYINRWIFVTITNNRLNKSKIYINGRLIDQKPISNLGNIHAS
NKIMFKLDGCRDTHRYIWIKYFNLFDKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRNNDRVYINVVVKNKEYRLATNASQA
GVEKILSALEIPDVGNLSQVVVMKSKNDKGITNKCKMNLQDNNGNDIGFIGFHQFNNIAKLVASNWYNRQIERSS
RTLGCSWEFIPVDDGWGERPL

FIGURE 5

(SEQ ID No. 3)
ATGCCATTCGTCAACAAGCAATTCAACTACAAAGACCCAGTCAACGGCGTCGACATCGCATACATCAAGATTCCG
AACGCCGGTCAAATGCAGCCGGTTAAGGCTTTTAAGATCCACAACAAGATTTGGGTTATCCCGGAGCGTGACACC
TTCACGAACCCGGAAGAAGGCGATCTGAACCCGCCACCGGAAGCGAAGCAAGTCCCTGTCAGCTACTACGATTCG
ACGTACCTGAGCACGGATAACGAAAAAGATAACTACCTGAAAGGTGTGACCAAGCTGTTCGAACGTATCTACAGC
ACGGATCTGGGTCGCATGCTGCTGACTAGCATTGTTCGCGGTATCCCGTTCTGGGGTGGTAGCACGATTGACACC
GAACTGAAGGTTATCGACACTAACTGCATTAACGTTATTCAACCGGATGGTAGCTATCGTAGCGAAGAGCTGAAT
CTGGTCATCATTGGCCCGAGCGCAGACATTATCCAATTCGAGTGCAAGAGCTTTGGTCACGAGGTTCTGAATCTG
ACCCGCAATGGCTATGGTAGCACCCAGTACATTCGTTTTTCGCCGGATTTTACCTTCGGCTTTGAAGAGAGCCTG
GAGGTTGATACCAATCCGTTGCTGGGTGCGGGCAAATTCGCTACCGATCCGGCTGTCACGCTGGCCCATcAACTG
ATCtACGCAGGCCACCGCCTGTACGGCATTGCCATCAACCCAAACCGTGTGTTCAAGGTTAATACGAATGCATAC
TACGAGATGAGCGGCCTGGAAGTCAGCTTCGAAGAACTGCGCACCTTCGGTGGCCATGACGCTAAATTCATTGAC
AGCTTGCAAGAGAATGAGTTCCGTCTGTACTACTATAACAAATTCAAAGACATTGCAAGCACGTTGAACAAGGCC
AAAAGCATCGTTGGTACTACCGCGTCGTTGCAGTATATGAAGAATGTGTTTAAAGAGAAGTACCTGCTGTCCGAG
GATACCTCCGGCAAGTTTAGCGTTGATAAGCTGAAGTTTGACAAACTGTACAAGATGCTGACCGAGATTTACACC
GAGGACAACTTTGTGAAATTCTTCAAAGTGTTGAATCGTAAAACCTATCTGAATTTTGACAAAGCGGTTTTCAAG
ATTAACATCGTGCCGAAGGTGAACTACACCATCTATGACGGTTTTAACCTGCGTAACACCAACCTGGCGGCGAAC
TTTAACGGTCAGAATACGGAAATCAACAACATGAATTTCACGAAGTTGAAGAACTTCACGGGTCTGTTCGAGTTC
TATAAGCTGCTGTGCGTGCGCGGTATCATCACCAGCAAAACCAAAAGCCTGGACAAAGGCTACAACAAGGCGCTG
AATGACCTGTGCATTAAGGTAAACAATTGGGATCTGTTCTTTTCGCCATCCGAAGATAATTTTACCAACGACCTG
AACAAGGGTGAAGAAATCACCAGCGATACGAATATTGAAGCAGCGGAAGAGAATATCAGCCTGGATCTGATCCAG
CAGTACTATCTGACCTTTAACTTCGACAATGAACCGGAGAACATTAGCATTGAGAATCTGAGCAGCGACATTATC
GGTCAGCTGGAACTGATGCCGAATATCGAACGTTTCCCGAACGGCAAAAAGTACGAGCTGGACAAGTACACTATG
TTCCATTACCTGCGTGCACAGGAGTTTGAACACGGTAAAAGCCGTATCGCGCTGACCAACAGCGTTAACGAGGCC
CTGCTGAACCCGAGCCGTGTCTATACCTTCTTCAGCAGCGACTATGTTAAGAAAGTGAACAAAGCCACTGAGGCC
GCGATGTTCCTGGGCTGGGTGGAACAGCTGGTATATGACTTCACGGACGAGACGAGCGAAGTGAGCACTACCGAC
AAAATTGCTGATATTACCATCATTATCCCGTATATTGGTCCGGCACTGAACATTGGCAACATGCTGTACAAAGAC
GATTTTGTGGGTGCCCTGATCTTCTCCGGTGCCGTGATTCTGCTGGAGTTCATTCCGGAGATTGCGATCCCGGTG
TTGGGTACCTTCGCGCTGGTGTCCTACATCGCGAATAAGGTTCTGACGGTTCAGACCATCGATAACGCGCTGTCG
AAACGTAATGAAAAATGGGACGAGGTTTACAAATACATTGTTACGAATTGGCTGGCGAAAGTCAATACCCAGATC
GACCTGATCCGTAAGAAAATGAAAGAGGCGCTGGAGAATCAGGCGGAGGCCACCAAAGCAATTATCAACTACCAA
TACAACCAGTACACGGAAGAAGAGAAGAATAACATTAACTTCAATATCGATGATTTGAGCAGCAAGCTGAATGAA
TCTATCAACAAAGCGATGATCAATATCAACAAGTTTTTGAATCAGTGTAGCGTTTCGTACCTGATGAATAGCATG
ATTCCGTATGGCGTCAAACGTCTGGAGGACTTCGACGCCAGCCTGAAAGATGCGTTGCTGAAATACATTTACGAC
AATCGTGGTACGCTGATTGGCCAAGTTGACCGCTTGAAAGACAAAGTTAACAATACCCTGAGCACCGACATCCCA
TTTCAACTGAGCAAGTATGTTGATAATCAACGTCTGTTGAGCACTTTCACCGAGTATATCAAAACATCATCAAT
ACTAGCATTCTGAACCTGCGTTACGAGAGCAATCATCTGATTGATCTGAGCCGTTATGCAAGCAAGATCAACATC
GGTAGCAAGGTCAATTTTGACCCGATCGATAAGAACCAGATCCAGCTGTTTAATCTGGAATCGAGCAAAATTGAG
GTTATCCTGAAAAACGCCATTGTCTACAACTCCATGTACGAGAATTTCTCCACCAGCTTCTGGATTCGCATCCCG
AAATACTTCAACAGCATTAGCCTGAACAACGAGTATACTATCATCAACTGTATGGAGAACAACAGCGGTTGGAAG
GTGTCTCTGAACTATGGTGAGATCATTTGGACCTTGCAGGACACCCAAGAGATCAAGCAGCGCGTCGTGTTCAAG
TACTCTCAAATGATCAACATTTCCGATTACATTAATCGTTGGATCTTCGTGACCATTACGAATAACCGTCTGAAT
AACAGCAAGATTTACATCAATGGTCGCTTGATCGATCAGAAACCGATTAGCAACCTGGGTAATATCCACGCAAGC
AACAACATTATGTTCAAATTGGACGGTTGCCGCGATACCCATCGTTATATCTGGATCAAGTATTTCAACCTGTTT
GATAAAGAACTGAATGAGAAGGAGATCAAAGATTTGTATGACAACCAATCTAACAGCGGCATTTTGAAGGACTTC
TGGGGCGATTATCTGCAATACGATAAGCCGTACTATATGCTGAACCTGTATGATCCGAACAAATATGTGGATGTC
AATAATGTGGGTATTCGTGGTTACATGTATTTGAAGGGTCCGCGTGGCAGCGTTATGACGACCAACATTTACCTG
AACTCTAGCCTGTACCGTGGTACGAAATTCATCATTAAGAAATATGCCAGCGGCAACAAAGATAACATTGTGCGT
AATAACGATCGTGTCTACATCAACGTGGTCGTGAAGAATAAAGAGTACCGTCTGGCGACCAACGCTTCGCAGGCG
GGTGTTGAGAAAATTCTGAGCGCGTTGGAGATCCCTGATGTCGGTAATCTGAGCCAAGTCGTGGTTATGAAGAGC
AAGAACGACCAGGGTATCACTAACAAGTGCAAGATGAACCTGCAAGACAACAATGGTAACGACATCGGCTTTATT
GGTTTCCACCAGTTCAACAATATTGCTAAACTGGTAGCGAGCAATTGGTACAATCGTCAGATTGAGCGCAGCAGC
CGTACTTTGGGCTGTAGCTGGGAGTTTATCCCGGTCGATGATGGTTGGGCGAACGTCCGCTG

FIGURE 6

(SEQ ID No. 4)
MPFVNKQFNYKDPVNGVDIAYIKIPNAGQMQPVKAFKIHNKIWVIPERDTFTNPEEGDLNPPPEAKQVPVSYYDS
TYLSTDNEKDNYLKGVTKLFERIYSTDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESLEVDTNPLLGAGKFATDPAVTLAHQL
IYAGHRLYGIAINPNRVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKVLNRKTYLNFDKAVFK
INIVPKVNYTIYDGFNLRNTNLAANFNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQQYYLTFNFDNEPENISIENLSSDII
GQLELMPNIERFPNGKKYELDKYTMFHYLRAQEFEHGKSRIALTNSVNEALLNPSRVYTFFSSDYVKKVNKATEA
AMFLGWVEQLVYDFTDETSEVSTTDKIADITIIIPYIGPALNIGNMLYKDDFVGALIFSGAVILLEFIPEIAIPV
LGTFALVSYIANKVLTVQTIDNALSKRNEKWDEVYKYIVTNWLAKVNTQIDLIRKKMKEALENQAEATKAIINYQ
YNQYTEEEKNNINFNIDDLSSKLNESINKAMININKFLNQCSVSYLMNSMIPYGVKRLEDFDASLKDALLKYIYD
NRGTLIGQVDRLKDKVNNTLSTDIPFQLSKYVDNQRLLSTFTEYIKNIINTSILNLRYESNHLIDLSRYASKINI
GSKVNFDPIDKNQIQLFNLESSKIEVILKNAIVYNSMYENFSTSFWIRIPKYFNSISLNNEYTIINCMENNSGWK
VSLNYGEIIWTLQDTQEIKQRVVFKYSQMINISDYINRWIFVTITNNRLNNSKIYINGRLIDQKPISNLGNIHAS
NNIMFKLDGCRDTHRYIWIKYFNLFDKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRNNDRVYINVVVKNKEYRLATNASQA
GVEKILSALEIPDVGNLSQVVVMKSKNDQGITNKCKMNLQDNNGNDIGFIGFHQFNNIAKLVASNWYNRQIERSS
RTLGCSWEFIPVDDGWGERPL

FIGURE 7

(SEQ ID No. 5)

```
ATGCCATTCGTCAACAAGCAATTCAACTACAAAGACCCAGTCAACGGCGTCGACATCGCATACATCAAGATTCCG
AACGCCGGTCAAATGCAGCCGGTTAAGGCTTTTAAGATCCACAACAAGATTTGGGTTATCCCGGAGCGTGACACC
TTCACGAACCCGGAAGAAGGCGATCTGAACCCGCCACCGGAAGCGAAGCAAGTCCCTGTCAGCTACTACGATTCG
ACGTACCTGAGCACGGATAACGAAAAGATAACTACCTGAAAGGTGTGACCAAGCTGTTCGAACGTATCTACAGC
ACGGATCTGGGTCGCATGCTGCTGACTAGCATTGTTCGCGGTATCCCGTTCTGGGGTGGTAGCACGATTGACACC
GAACTGAAGGTTATCGACACTAACTGCATTAACGTTATTCAACCGGATGGTAGCTATCGTAGCGAAGAGCTGAAT
CTGGTCATCATTGGCCCGAGCGCAGACATTATCCAATTCGAGTGCAAGAGCTTTGGTCACGAGGTTCTGAATCTG
ACCCGCAATGGCTATGGTAGCACCCAGTACATTCGTTTTCGCCGGATTTTACCTTCGGCTTTGAAGAGAGCCTG
GAGGTTGATACCAATCCGTTGCTGGGTGCGGGCAAATTCGCTACCGATCCGGCTGTCACGCTGGCCCATGAACTG
ATCCACGCAGGCCACCGCCTGTACGGCATTGCCATCAACCCAAACCGTGTGTTCAAGGTTAATACGAATGCATAC
TACGAGATGAGCGGCCTGGAAGTCAGCTTCGAAGAACTGCGCACCTTCGGTGGCCATGACGCTAAATTCATTGAC
AGCTTGCAAGAGAATGAGTTCCGTCTGTACTACTATAACAAATTCAAAGACATTGCAAGCACGTTGAACAAGGCC
AAAAGCATCGTTGGTACTACCGCGTCGTTGCAGTATATGAAGAATGTGTTTAAAGAGAAGTACCTGCTGTCCGAG
GATACCTCCGGCAAGTTTAGCGTTGATAAGCTGAAGTTTGACAAACTGTACAAGATGCTGACCGAGATTTACACC
GAGGACAACTTTGTGAAATTCTTCAAAGTGTTGAATCGTAAAACCTATCTGAATTTTGACAAAGCGGTTTTCAAG
ATTAACATCGTGCCGAAGGTGAACTACACCATCTATGACGGTTTTAACCTGCGTAACACCAACCTGGCGGCGAAC
TTTAACGGTCAGAATACGGAAATCAACAACATGAATTTCACGAAGTTGAAGAACTTCACGGGTCTGTTCGAGTTC
TATAAGCTGCTGTGCGTGCGCGGTATCATCACCAGCAAAACCAAAAGCCTGGACAAAGGCTACAACAAGGCGCTG
AATGACCTGTGCATTAAGGTAAACAATTGGGATCTGTTCTTTTCGCCATCCGAAGATAATTTTACCAACGACCTG
AACAAGGGTGAAGAAATCACCAGCGATACGAATATTGAAGCAGCGGAAGAGAATATCAGCCTGGATCTGATCCAG
CAGTACTATCTGACCTTTAACTTCGACAATGAACCGGAGAACATTAGCATTGAGAATCTGAGCAGCGACATTATC
GGTCAGCTGGAACTGATGCCGAATATCGAACGTTTCCCGAACGGCAAAAAGTACGAGCTGGACAAGTACACTATG
TTCCATTACCTGCGTGCACAGGAGTTTGAACACGGTAAAcgtCGTATCGCGCTGACCAACAGCGTTAACGAGGCC
CTGCTGAACCCGAGCCGTGTCTATACCTTCTTCAGCAGCGACTATGTTAAGAAAGTGAACAAAGCCACTGAGGCC
GCGATGTTCCTGGGCTGGGTGGAACAGCTGGTATATGACTTCACGGACGAGACGAGCGAAGTGAGCACTACCGAC
AAAATTGCTGATATTACCATCATTATCCCGTATATTGGTCCGGCACTGAACATTGGCAACATGCgtTACAAAcgt
cgTTTTGTGGGTGCCCTGATCTTCTCCGGTGCCGTGATTCTGCTGGAGTTCATTCCGGAGATTGCGATCCCGGTG
TTGGGTACCTTCGCGCTGGTGTCCTACATCGCGAATAAGGTTCTGACGGTTCAGACCATCGATAACGCGCTGTCG
AAACGTAATGAAAAATGGGACGAGGTTTACAAATACATTGTTACGAATTGGCTGGCGAAAGTCAATACCCAGATC
GACCTGATCCGTAAGAAAATGAAAGAGGCGCTGGAGAATCAGGCGGAGGCCACCAAAGCAATTATCAACTACCAA
TACAACCAGTACACGGAAGAAGAGAAGAATAACATTAACTTCAATATCGATGATTTGAGCAGCAAGCTGAATGAA
TCTATCAACAAAGCGATGATCAATATCAACAAGTTTTTGAATCAGTGTAGCGTTTCGTACCTGATGAATAGCATG
ATTCCGTATGGCGTCAAACGTCTGGAGGACTTCGACGCCAGCCTGAAAGATGCGTTGCTGAAATACATTTACGAC
AATCGTGGTACGCTGATTGGCCAAGTTGACCGCTTGAAAGACAAAGTTAACAATACCCTGAGCCgtGACcgtCCA
TTTCAACTGAGCAAGTATGTTGATAATCAACGTCTGTTGAGCACTTTCACCGAGTATATCAAAAACATCATCAAT
ACTAGCATTCTGAACCTGCGTTACGAGAGCAATCATCTGATTGATCTGAGCCGTTATGCAAGCAAGATCAACATC
GGTAGCAAGGTCAATTTTGACCCGATCGATAAGAACCAGATCCAGCTGTTTAATCTGGAATCGAGCAAAATTGAG
GTTATCCTGAAAAACGCCATTGTCTACAACTCCATGTACGAGAATTTCTCCACCAGCTTCTGGATTCGCATCCCG
AAATACTTCAACAGCATTAGCCTGAACAACGAGTATACTATCATCAACTGTATGGAGAACAACAGCGGTTGGAAG
GTGTCTCTGAACTATGGTGAGATCATTTGGACCTTGCAGGACACCCAAGAGATCAAGCAGCGCGTCGTGTTCAAG
TACTCTCAAATGATCAACATTTCCGATTACATTAATCGTTGGATCTTCGTGACCATTACGAATAACCGTCTGAAT
AACAGCAAGATTTACATCAATGGTCGCTTGATCGATCAGAAACCGATTAGCAACCTGGGTAATATCCACGCAAGC
AACAACATTATGTTCAAATTGGACGGTTGCCGCGATACCCATCGTTATATCTGGATCAAGTATTTCAACCTGTTT
GATAAAGAACTGAATGAGAAGGAGATCAAAGATTTGTATGACAACCAATCTAACAGCGGCATTTTGAAGGACTTC
TGGGGCGATTATCTGCAATACGATAAGCCGTACTATATGCTGAACCTGTATGATCCGAACAAATATGTGGATGTC
AATAATGTGGGTATTCGTGGTTACATGTATTTGAAGGGTCCGCGTGGCAGCGTTATGACGACCAACATTTACCTG
AACTCTAGCCTGTACCGTGGTACGAAATTCATCATTAAGAAATATGCCAGCGGCAACAAAGATAACATTGTGCGT
AATAACGATCGTGTCTACATCAACGTGGTCGTGAAGAATAAAGAGTACCGTCTGGCGACCAACGCTTCGCAGGCG
GGTGTTGAGAAAATTCTGAGCGCGTTGGAGATCCCTGATGTCGGTAATCTGAGCCAAGTCGTGGTTATGAAGAGC
AAGAACGACCAGGGTATCACTAACAAGTGCAAGATGAACCTGCAAGACAACAATGGTAACGACATCGGCTTTATT
GGTTTCCACCAGTTCAACAATATTGCTAAACTGGTAGCGAGCAATTGGTACAATCGTCAGATTGAGCGCAGCAGC
CGTACTTTGGGCTGTAGCTGGGAGTTTATCCCGGTCGATGATGGTTGGGGCGAACGTCCGCTG
```

FIGURE 8

(SEQ ID No. 6)

```
MPFVNKQFNYKDPVNGVDIAYIKIPNAGQMQPVKAFKIHNKIWVIPERDTFTNPEEGDLNPPPEAKQVPVSYYDS
TYLSTDNEKDNYLKGVTKLFERIYSTDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESLEVDTNPLLGAGKFATDPAVTLAHEL
IHAGHRLYGIAINPNRVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKVLNRKTYLNFDKAVFK
INIVPKVNYTIYDGFNLRNTNLAANFNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQQYYLTFNFDNEPENISIENLSSDII
GQLELMPNIERFPNGKKYELDKYTMFHYLRAQEFEHGKRRIALTNSVNEALLNPSRVYTFFSSDYVKKVNKATEA
AMFLGWVEQLVYDFTDETSEVSTTDKIADITIIIPYIGPALNIGNMRYKRRFVGALIFSGAVILLEFIPEIAIPV
LGTFALVSYIANKVLTVQTIDNALSKRNEKWDEVYKYIVTNWLAKVNTQIDLIRKKMKEALENQAEATKAIINYQ
YNQYTEEEKNNINFNIDDLSSKLNESINKAMININKFLNQCSVSYLMNSMIPYGVKRLEDFDASLKDALLKYIYD
NRGTLIGQVDRLKDKVNNTLSRDRPFQLSKYVDNQRLLSTFTEYIKNIINTSILNLRYESNHLIDLSRYASKINI
GSKVNFDPIDKNQIQLFNLESSKIEVILKNAIVYNSMYENFSTSFWIRIPKYFNSISLNNEYTIINCMENNSGWK
VSLNYGEIIWTLQDTQEIKQRVVFKYSQMINISDYINRWIFVTITNNRLNNSKIYINGRLIDQKPISNLGNIHAS
NNIMFKLDGCRDTHRYIWIKYFNLFDKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRNNDRVYINVVVKNKEYRLATNASQA
GVEKILSALEIPDVGNLSQVVVMKSKNDQGITNKCKMNLQDNNGNDIGFIGFHQFNNIAKLVASNWYNRQIERSS
RTLGCSWEFIPVDDGWGERPL
```

FIGURE 9

(SEQ ID No. 7)

ATGCCATTCGTCAACAAGCAATTCAACTACAAAGACCCAGTCAACGGCGTCGACATCGCATACATCAAGATTCCG
AACGCCGGTCAAATGCAGCCGGTTAAGGCTTTTAAGATCCACAACAAGATTTGGGTTATCCCGGAGCGTGACACC
TTCACGAACCCGGAAGAAGGCGATCTGAACCCGCCACCGGAAGCGAAGCAAGTCCCTGTCAGCTACTACGATTCG
ACGTACCTGAGCACGGATAACGAAAAGATAACTACCTGAAAGGTGTGACCAAGCTGTTCGAACGTATCTACAGC
ACGGATCTGGGTCGCATGCTGCTGACTAGCATTGTTCGCGGTATCCCGTTCTGGGGTGGTAGCACGATTGACACC
GAACTGAAGGTTATCGACACTAACTGCATTAACGTTATTCAACCGGATGGTAGCTATCGTAGCGAAGAGCTGAAT
CTGGTCATCATTGGCCCGAGCGCAGACATTATCCAATTCGAGTGCAAGAGCTTTGGTCACGAGGTTCTGAATCTG
ACCCGCAATGGCTATGGTAGCACCCAGTACATTCGTTTTCGCCGGATTTTACCTTCGGCTTTGAAGAGAGCCTG
GAGGTTGATACCAATCCGTTGCTGGGTGCGGGCAAATTCGCTACCGATCCGGCTGTCACGCTGGCCCATGAACTG
ATCCACGCAGGCCACCGCCTGTACGGCATTGCCATCAACCCAAACCGTGTGTTCAAGGTTAATACGAATGCATAC
TACGAGATGAGCGGCCTGGAAGTCAGCTTCGAAGAACTGCGCACCTTCGGTGGCCATGACGCTAAATTCATTGAC
AGCTTGCAAGAGAATGAGTTCCGTCTGTACTACTATAACAAATTCAAAGACATTGCAAGCACGTTGAACAAGGCC
AAAAGCATCGTTGGTACTACCGCGTCGTTGCAGTATATGAAGAATGTGTTTAAAGAGAAGTACCTGCTGTCCGAG
GATACCTCCGGCAAGTTTAGCGTTGATAAGCTGAAGTTTGACAAACTGTACAAGATGCTGACCGAGATTTACACC
GAGGACAACTTTGTGAAATTCTTCAAAGTGTTGAATCGTAAAACCTATCTGAATTTTGACAAAGCGGTTTTCAAG
ATTAACATCGTGCCGAAGGTGAACTACACCATCTATGACGGTTTTAACCTGCGTAACACCAACCTGGCGGCGAAC
TTTAACGGTCAGAATACGGAAATCAACAACATGAATTTCACGAAGTTGAAGAACTTCACGGGTCTGTTCGAGTTC
TATAAGCTGCTGTGCGTGCGCGGTATCATCACCAGCAAAACCAAAAGCCTGGACAAAGGCTACAACAAGGCGCTG
AATGACCTGTGCATTAAGGTAAACAATTGGGATCTGTTCTTTTCGCCATCCGAAGATAATTTTACCAACGACCTG
AAgAAGGGTGAAGAAATCACCAGCGATACGAATATTGAAGCAGCGGAAGAGAATATCAGCCTGGATCTGATCCAG
CAGTACTATCTGACCTTTAACTTCGACAATGAACCGGAGAACATTAGCATTGAGAATCTGAGCAGCGACATTATC
GGTCAGCTGGAACTGATGCCGAATATCGAACGTTTCCCGAACGGCAAAAGTACGAGCTGGACAAGTACACTATG
TTCCATTACCTGCGTGCACAGGAGTTTGAACACGGTAAAAGCCGTATCGCGCTGACCAACAGCGTTAACGAGGCC
CTGCTGAACCCGAGCCGTGTCTATACCTTCTTCAGCAGCGACTATGTTAAGAAAGTGAACAAAGCCACTaAGGCC
GCGATGTTCCTGGGCTGGGTGGAACAGCTGGTATATGACTTCACGGACGAGACGAGCGAAGTGAGCACTACCGAC
AAAATTGCTGATATTACCATCATTATCCCGTATATTGGTCCGGCACTGAACATTGGCAACATGCTGTACAAAGAC
GATTTTGTGGGTGCCCTGATCTTCTCCGGTGCCGTGATTCTGCTGGAGTTCATTCCGGAGATTGCGATCCCGGTG
TTGGGTACCTTCGCGCTGGTGTCCTACATCGCGAAgAAGGTTCTGACGGTTCAGACCATCGATAACGCGCTGTCG
AAACGTAATGAAAAATGGGACGAGGTTTACAAATACATTGTTACGAATTGGCTGGCGAAAGTCAATACCCAGATC
GACCTGATCCGTAAGAAAATGAAAGAGGCGCTGGAGAATCAGGCGGAGGCCACCAAAGCAATTATCAACTACCAA
TACAACCAGTACACGGAAGAAGAGAAGAATAAgATTAAgTTCAATATCGATGATTTGAGCAGCAAGCTGAATGAA
TCTATCAACAAAGCGATGATCAATATCAACAAGTTTTTGAATCAGTGTAGCGTTTCGTACCTGATGAATAGCATG
ATTCCGTATGGCGTCAAACGTCTGGAGGACTTCGACGCCAGCCTGAAAGATGCGTTGCTGAAATACATTTACGAC
AATCGTGGTACGCTGAagGGCCAAGTTGACCGCTTGAAAGACAAAGTTAACAATACCCTGAGCACCGACATCCCA
TTTCAACTGAGCAAGTATGTTGATAATCAACGTCTGTTGAGCACTTTCACCGAGTATATCAAAAACATCATCAAT
ACTAGCATTCTGAACCTGCGTTACGAGAGCAATCATCTGATTGATCTGAGCCGTTATGCAAGCAAGATCAACATC
GGTAGCAAGGTCAATTTTGACCCGATCGATAAGAACCAGATCCAGCTGTTTAATCTGGAATCGAGCAAAATTGAG
GTTATCCTGAAAAACGCCATTGTCTACAACTCCATGTACGAGAATTTCTCCACCAGCTTCTGGATTCGCATCCCG
AAATACTTCAACAGCATTAGCCTGAACAACGAGTATACTATCATCAACTGTATGGAGAACAACAGCGGTTGGAAG
GTGTCTCTGAACTATGGTGAGATCATTTGGACCTTGCAGGACACCCAAGAGATCAAGCAGCGCGTCGTGTTCAAG
TACTCTCAAATGATCAACATTTCCGATTACATTAATCGTTGGATCTTCGTGACCATTACGAATAACCGTCTGAAT
AACAGCAAGATTTACATCAATGGTCGCTTGATCGATCAGAAACCGATTAGCAACCTGGGTAATATCCACGCAAGC
AACAACATTATGTTCAAATTGGACGGTTGCCGCGATACCCATCGTTATATCTGGATCAAGTATTTCAACCTGTTT
GATAAAGAACTGAATGAGAAGGAGATCAAAGATTTGTATGACAACCAATCTAACAGCGGCATTTTGAAGGACTTC
TGGGGCGATTATCTGCAATACGATAAGCCGTACTATATGCTGAACCTGTATGATCCGAACAAATATGTGGATGTC
AATAATGTGGGTATTCGTGGTTACATGTATTTGAAGGGTCCGCGTGGCAGCGTTATGACGACCAACATTTACCTG
AACTCTAGCCTGTACCGTGGTACGAAATTCATCATTAAGAAATATGCCAGCGGCAACAAAGATAACATTGTGCGT
AATAACGATCGTGTCTACATCAACGTGGTCGTGAAGAATAAAGAGTACCGTCTGGCGACCAACGCTTCGCAGGCG
GGTGTTGAGAAAATTCTGAGCGCGTTGGAGATCCCTGATGTCGGTAATCTGAGCCAAGTCGTGGTTATGAAGAGC
AAGAACGACCAGGGTATCACTAACAAGTGCAAGATGAACCTGCAAGACAACAATGGTAACGACATCGGCTTTATT
GGTTTCCACCAGTTCAACAATATTGCTAAACTGGTAGCGAGCAATTGGTACAATCGTCAGATTGAGCGCAGCAGC
CGTACTTTGGGCTGTAGCTGGGAGTTTATCCCGGTCGATGATGGTTGGGGCGAACGTCCGCTG

FIGURE 10

(SEQ ID No. 8)

MPFVNKQFNYKDPVNGVDIAYIKIPNAGQMQPVKAFKIHNKIWVIPERDTFTNPEEGDLNPPPEAKQVPVSYYDS
TYLSTDNEKDNYLKGVTKLFERIYSTDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESLEVDTNPLLGAGKFATDPAVTLAHEL
IHAGHRLYGIAINPNRVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKVLNRKTYLNFDKAVFK
INIVPKVNYTIYDGFNLRNTNLAANFNGQNTEINNMNFTKLKNFTGLFEFYKLLCVRGIITSKTKSLDKGYNKAL
NDLCIKVNNWDLFFSPSEDNFTNDLKKGEEITSDTNIEAAEENISLDLIQQYYLTFNFDNEPENISIENLSSDII
GQLELMPNIERFPNGKKYELDKYTMFHYLRAQEFEHGKSRIALTNSVNEALLNPSRVYTFFSSDYVKKVNKATKA
AMFLGWVEQLVYDFTDETSEVSTTDKIADITIIIPYIGPALNIGNMLYKDDFVGALIFSGAVILLEFIPEIAIPV
LGTFALVSYIAKKVLTVQTIDNALSKRNEKWDEVYKYIVTNWLAKVNTQIDLIRKKMKEALENQAEATKAIINYQ
YNQYTEEEKNKIKFNIDDLSSKLNESINKAMININKFLNQCSVSYLMNSMIPYGVKRLEDFDASLKDALLKYIYD
NRGTLKGQVDRLKDKVNNTLSTDIPFQLSKYVDNQRLLSTFTEYIKNIINTSILNLRYESNHLIDLSRYASKINI
GSKVNFDPIDKNQIQLFNLESSKIEVILKNAIVYNSMYENFSTSFWIRIPKYFNSISLNNEYTIINCMENNSGWK
VSLNYGEIIWTLQDTQEIKQRVVFKYSQMINISDYINRWIFVTITNNRLNNSKIYINGRLIDQKPISNLGNIHAS
NNIMFKLDGCRDTHRYIWIKYFNLFDKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRNNDRVYINVVVKNKEYRLATNASQA
GVEKILSALEIPDVGNLSQVVVMKSKNDQGITNKCKMNLQDNNGNDIGFIGFHQFNNIAKLVASNWYNRQIERSS
RTLGCSWEFIPVDDGWGERPL

FIGURE 11

(SEQ ID No. 9)

```
ATGCCATTCGTCAACAAGCAATTCAACTACAAAGACCCAGTCAACGGCGTCGACATCGCATACATCAAGATTCCG
AACGCCGGTCAAATGCAGCCGGTTAAGGCTTTTAAGATCCACAACAAGATTTGGGTTATCCCGGAGCGTGACACC
TTCACGAACCCGGAAGAAGGCGATCTGAACCCGCCACCGGAAGCGAAGCAAGTCCCTGTCAGCTACTACGATTCG
ACGTACCTGAGCACGGATAACGAAAAGATAACTACCTGAAAGGTGTGACCAAGCTGTTCGAACGTATCTACAGC
ACGGATCTGGGTCGCATGCTGCTGACTAGCATTGTTCGCGGTATCCCGTTCTGGGGTGGTAGCACGATTGACACC
GAACTGAAGGTTATCGACACTAACTGCATTAACGTTATTCAACCGGATGGTAGCTATCGTAGCGAAGAGCTGAAT
CTGGTCATCATTGGCCCGAGCGCAGACATTATCCAATTCGAGTGCAAGAGCTTTGGTCACGAGGTTCTGAATCTG
ACCCGCAATGGCTATGGTAGCACCCAGTACATTCGTTTTCGCCGGATTTTACCTTCGGCTTTGAAGAGAGCCTG
GAGGTTGATACCAATCCGTTGCTGGGTGCGGGCAAATTCGCTACCGATCCGGCTGTCACGCTGGCCCATGAACTG
ATCCACGCAGGCCACCGCCTGTACGGCATTGCCATCAACCCAAACCGTGTGTTCAAGGTTAATACGAATGCATAC
TACGAGATGAGCGGCCTGGAAGTCAGCTTCGAAGAACTGCGCACCTTCGGTGGCCATGACGCTAAATTCATTGAC
AGCTTGCAAGAGAATGAGTTCCGTCTGTACTACTATAACAAATTCAAAGACATTGCAAGCACGTTGAACAAGGCC
AAAAGCATCGTTGGTACTACCGCGTCGTTGCAGTATATGAAGAATGTGTTTAAAGAGAAGTACCTGCTGTCCGAG
GATACCTCCGGCAAGTTTAGCGTTGATAAGCTGAAGTTTGACAAACTGTACAAGATGCTGACCGAGATTTACACC
GAGGACAACTTTGTGAAATTCTTCAAAGTGTTGAATCGTAAAACCTATCTGAATTTTGACAAAGCGGTTTTCAAG
ATTAACATCGTGCCGAAGGTGAACTACACCATCTATGACGGTTTTAACCTGCGTAACACCAACCTGGCGGCGAAC
TTTAACGGTCAGAATACGGAAATCAACAACATGAATTTCACGAAGTTGAAGAACTTCACGGGTCTGTTCGAGTTC
TATAAGCTGCTGTGCGTGCGCGGTATCATCACCAGCAAAACCAAAAGCCTGGACAAAGGCTACAACAAGGCGCTG
AATGACCTGTGCATTAAGGTAAACAATTGGGATCTGTTCTTTTCGCCATCCGAAGATAATTTTACCAACGACCTG
AACAAGGGTGAAGAAATCACCAGCGaTACGAATATTGAAGCAGCGGAAGAGAATATCAGCCTGGATCTGATCCAG
CAGTACTATCTGACCTTTAACTTCGACAATGAACCGGAGAACATTAGCATTGAGAATCTGAGCAGCGACATTATC
GGTCAGCTGGAACTGATGCCGAATATCGAACGTTTCCCGAACGGCAAAAAGTACGAGCTGGACAAGTACACTATG
TTCCATTACCTGCGTGCACAGGAGTTTGAACACGGTAAAAGCCGTATCGCGCTGACCAACAGCGTTAACGAGGCC
CTGCTGAAaCCGAGCCGTGTCTATACCTTCTTCAGCAGCGACTATGTTAAGAAAGTGAACAAAGCCACTGAGGCC
GCGATGTTCCTGGGCTGGGTGGAACAGCTGGTATATGACTTCACGGACGAGACGAGCGAAGTGAGCACTACCGAC
AAAAATTGCTGATATTACCATCATTATCCCGTATATTGGTCCGGCACTGAACATTGGCAACATGCTGTACAAAGAC
GATTTTGTGGGTGCCCTGATCTTCTCCGGTGCCGTGATTCTGCTGGAGTTCATTCCGGAGATTGCGATCCCGaaG
TTGGGTACCTTCGCGCTGGTGTCCTACAagGCGAATAAGGTTCTGACGGTTCAGACCATCGATAACGCGCTGTCG
AAACGTAATGAAAAATGGGACGAGGTTTACAAATACATTGTTACGAATTGGCTGGCGAAAGTCAATACCCAGATC
GACCTGATCCGTAAGAAAATGAAAGAGGCGCTGGAGAATCAGGCGGAGGCCACCAAAGCAATTATCAACTACCAA
TACAACCAGTACAaGGAAaAAGAGAAGAATAACATTAACTTCAATATCGATGATTTGAGCAGCAAGCTGAATGAA
TCTATCAACAAAGCGATGATCAATATCAACAAGTTTTTGAATCAGTGTAGCGTTTCGTACCTGATGAATAGCATG
ATTCCGTATGGCGTCAAACGTCTGGAGGACTTCGACGCCAGCCTGAAAGATGCGTTGCTGAAATACATTTACGAC
AATCGTGGTACGCTGATTGGCCAAGTTGACCGCTTGAAAGACAAAGTTAACAATACCCTGAGCACCGACATCCCA
TTTCAACTGAGCAAGTATGTTGATAATCAACGTCTGTTGAGCACTTTCACCGAGTATATCAAAAACATCATCAAT
ACTAGCATTCTGAACCTGCGTTACGAGAGCAATCATCTGATTGATCTGAGCCGTTATGCAAGCAAGATCAACATC
GGTAGCAAGGTCAATTTTGACCCGATCGATAAGAACCAGATCCAGCTGTTTAATCTGGAATCGAGCAAAATTGAG
GTTATCCTGAAAAACGCCATTGTCTACAACTCCATGTACGAGAATTTCTCCACCAGCTTCTGGATTCGCATCCCG
AAATACTTCAACAGCATTAGCCTGAACAACGAGTATACTATCATCAACTGTATGGAGAACAACAGCGGTTGGAAG
GTGTCTCTGAACTATGGTGAGATCATTTGGACCTTGCAGGACACCCAAGAGATCAAGCAGCGCGTCGTGTTCAAG
TACTCTCAAATGATCAACATTTCCGATTACATTAATCGTTGGATCTTCGTGACCATTACGAATAACCGTCTGAAT
AACAGCAAGATTTACATCAATGGTCGCTTGATCGATCAGAAACCGATTAGCAACCTGGGTAATATCCACGCAAGC
AACAACATTATGTTCAAATTGGACGGTTGCCGCGATACCCATCGTTATATCTGGATCAAGTATTTCAACCTGTTT
GATAAAGAACTGAATGAGAAGGAGATCAAAGATTTGTATGACAACCAATCTAACAGCGGCATTTTGAAGGACTTC
TGGGGCGATTATCTGCAATACGATAAGCCGTACTATATGCTGAACCTGTATGATCCGAACAAATATGTGGATGTC
AATAATGTGGGTATTCGTGGTTACATGTATTTGAAGGGTCCGCGTGGCAGCGTTATGACGACCAACATTTACCTG
AACTCTAGCCTGTACCGTGGTACGAAATTCATCATTAAGAAATATGCCAGCGGCAACAAAGATAACATTGTGCGT
AATAACGATCGTGTCTACATCAACGTGGTCGTGAAGAATAAAGAGTACCGTCTGGCGACCAACGCTTCGCAGGCG
GGTGTTGAGAAAATTCTGAGCGCGTTGGAGATCCCTGATGTCGGTAATCTGAGCCAAGTCGTGGTTATGAAGAGC
AAGAACGACCAGGGTATCACTAACAAGTGCAAGATGAACCTGCAAGACAACAATGGTAACGACATCGGCTTTATT
GGTTTCCACCAGTTCAACAATATTGCTAAACTGGTAGCGAGCAATTGGTACAATCGTCAGATTGAGCGCAGCAGC
CGTACTTTGGGCTGTAGCTGGGAGTTTATCCCGGTCGATGATGGTTGGGGCGAACGTCCGCTG
```

FIGURE 12

(SEQ ID No. 10)

MPFVNKQFNYKDPVNGVDIAYIKIPNAGQMQPVKAFKIHNKIWVIPERDTFTNPEEGDLNPPPEAKQVPVSYYDS
TYLSTDNEKDNYLKGVTKLFERIYSTDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESLEVDTNPLLGAGKFATDPAVTLAHEL
IHAGHRLYGIAINPNRVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKVLNRKTYLNFDKAVFK
INIVPKVNYTIYDGFNLRNTNLAANFNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQQYYLTFNFDNEPENISIENLSSDII
GQLELMPNIERFPNGKKYELDKYTMFHYLRAQEFEHGKSRIALTNSVNEALLKPSRVYTFFSSDYVKKVNKATEA
AMFLGWVEQLVYDFTDETSEVSTTDKIADITIIIPYIGPALNIGNMLYKDDFVGALIFSGAVILLEFIPEIAIPK
LGTFALVSYKANKVLTVQTIDNALSKRNEKWDEVYKYIVTNWLAKVNTQIDLIRKKMKEALENQAEATKAIINYQ
YNQYKEKEKNNINFNIDDLSSKLNESINKAMININKFLNQCSVSYLMNSMIPYGVKRLEDFDASLKDALLKYIYD
NRGTLIGQVDRLKDKVNNTLSTDIPFQLSKYVDNQRLLSTFTEYIKNIINTSILNLRYESNHLIDLSRYASKINI
GSKVNFDPIDKNQIQLFNLESSKIEVILKNAIVYNSMYENFSTSFWIRIPKYFNSISLNNEYTIINCMENNSGWK
VSLNYGEIIWTLQDTQEIKQRVVFKYSQMINISDYINRWIFVTITNNRLNNSKIYINGRLIDQKPISNLGNIHAS
NNIMFKLDGCRDTHRYIWIKYFNLFDKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRNNDRVYINVVVKNKEYRLATNASQA
GVEKILSALEIPDVGNLSQVVVMKSKNDQGITNKCKMNLQDNNGNDIGFIGFHQFNNIAKLVASNWYNRQIERSS
RTLGCSWEFIPVDDGWGERPL

FIGURE 13

(SEQ ID No. 11)

ATGAAAATCGAAGAAGGTAAACTGGTAATCTGGATTAACGGCGATAAAGGCTATAACGGTCTCGCTGAAGTCGGT
AAGAAATTCGAGAAAGATACCGGAATTAAAGTCACCGTTGAGCATCCGGATAAACTGGAAGAGAAATTCCCACAG
GTTGCGGCAACTGGCGATGGCCCTGACATTATCTTCTGGGCACACGACCGCTTTGGTGGCTACGCTCAATCTGGC
CTGTTGGCTGAAATCACCCCGGACAAAGCGTTCCAGGACAAGCTGTATCCGTTTACCTGGGATGCCGTACGTTAC
AACGGCAAGCTGATTGCTTACCCGATCGCTGTTGAAGCGTTATCGCTGATTTATAACAAAGATCTGCTGCCGAAC
CCGCCAAAAACCTGGGAAGAGATCCCGGCGCTGGATAAAGAACTGAAAGCGAAAGGTAAGAGCGCGCTGATGTTC
AACCTGCAAGAACCGTACTTCACCTGGCCGCTGATTGCTGCTGACGGGGGTTATGCGTTCAAGTATGAAAACGGC
AAGTACGACATTAAAGACGTGGGCGTGGATAACGCTGGCGCGAAAGCGGGTCTGACCTTCCTGGTTGACCTGATT
AAAAACAAACACATGAATGCAGACACCGATTACTCCATCGCAGAAGCTGCCTTTAATAAAGGCGAAACAGCGATG
ACCATCAACGGCCCGTGGGCATGGTCCAACATCGACACCAGCAAAGTGAATTATGGTGTAACGGTACTGCCGACC
TTCAAGGGTCAACCATCCAAACCGTTCGTTGGCGTGCTGAGCGCAGGTATTAACGCCGCCAGTCCGAACAAAGAG
CTGGCAAAAGAGTTCCTCGAAAACTATCTGCTGACTGATGAAGGTCTGGAAGCGGTTAATAAAGACAAACCGCTG
GGTGCCGTAGCGCTGAAGTCTTACGAGGAAGAGTTGGCGAAAGATCCACGTATTGCCGCCACTATGGAAAACGCC
CAGAAAGGTGAAATCATGCCGAACATCCCGCAGATGTCCGCTTTCTGGTATGCCGTGCGTACTGCGGTGATCAAC
GCCGCCAGCGGTCGTCAGACTGTCGATGAAGCCCTGAAAGACGCGCAGACTAATTCGAGCTCGAACAACAACAAC
AATAACAATAACAACAACCTCGGGATCGAGGGAAGGATTTCAGAATTCGGATCCATGCCAAAAATCAACAGCTTT
AATTACAATGACCCTGTAAACGATCGTACCATCCTATACATAAAGCCGGGTGGGTGTCAAGAGTTCTACAAATCT
TTCAATATTATGAAGAATATATGGATTATACCTGAGCGTAACGTTATTGGTACGACACCGCAAGATTTTCATCCA
CCTACTTCGTTGAAGAACGGTGACTCTTCCTATTACGACCCCAATTATCTCCAGTCGGATGAAGAGAAGGACAGA
TTCCTTAAAATAGTAACCAAAATCTTTAACAGGATTAATAACAATCTATCCGGAGGTATTTTGCTTGAAGAGCTT
AGTAAAGCTAATCCTTACCTAGGTAACGATAATACACCAGACAACAAGTTTCATATAGGCGATGCATCCGCCGTG
GAAATCAAATTTAGCAAGGGATCACAGCATATTCTCTTGCCCAACGTTATTATAATGGGGCGGAACCAGATTTA
TTTGAAACAAATTCGAGTAATATTAGCCTGAGAAATAACTATATGCCGTCAAACCATGGGTTCGGTAGCATAGCG
ATCGTTACTTTTTCTCCCGAATACAGTTTTCGCTTCAATGATAATAGTATAAATGAGTTTATCCAAGACCCCGCA
CTCACGCTTATGCACGAACTCATACACTCTTTACACGGCCTGTATGGCGCTAAGGGGATAACCACTACGTGTATC
ATTACTCAGCAAAAGAACCCATTGATAACGAACAGGAAGGGCATTAACATCGAGGAATTTCTTACATTTGGAGGC
AACGATCTGAACATTATAACTGTCGCACAGTACAATGACATCTATACCAACTTACTAAATGATTATAGAAAAATC
GCTTCTAAGTTATCCAAGGTTCAAGTCTCAAACCCTCAACTGAATCCGTATAAGGACATATTCCAAGAGAAATAT
GGATTAGACAAAGACGCGTCAGGAATCTATTCGGTAAACATTAACAAATTCGACGATATTTTGAAGAAACTTTAC
AGCTTCACGGAGTTCGACTTGGCCACCAAATTCCAGGTCAAATGCCGAGAGACATACATCGGACAGTATAAGTAT
TTCAAGCTGTCGAATCTCCTGAATGATTCCATATACAACATTAGTGAGGGTTACAATATAAATAACCTAAAGGTG
AATTTCCGAGGCCAAAACGCCAACCTAAATCCGCGCATCATTAAACCCATCACAGGACGGGGGTTAGTGAAGAAA
ATAATCCGGTTTGCGGTCGACAAGCTTGCGGCCGCACTCGAGCACCACCACCACCACCAC

FIGURE 14

(SEQ ID No. 12)

MKIEEGKLVIWINGDKGYNGLAEVGKKFEKDTGIKVTVEHPDKLEEKFPQVAATGDGPDIIFWAHDRFGGYAQSG
LLAEITPDKAFQDKLYPFTWDAVRYNGKLIAYPIAVEALSLIYNKDLLPNPPKTWEEIPALDKELKAKGKSALMF
NLQEPYFTWPLIAADGGYAFKYENGKYDIKDVGVDNAGAKAGLTFLVDLIKNKHMNADTDYSIAEAAFNKGETAM
TINGPWAWSNIDTSKVNYGVTVLPTFKGQPSKPFVGVLSAGINAASPNKELAKEFLENYLLTDEGLEAVNKDKPL
GAVALKSYEEELAKDPRIAATMENAQKGEIMPNIPQMSAFWYAVRTAVINAASGRQTVDEALKDAQTNSSSNNNN
NNNNNNLGIEGRISEFGSMPKINSFNYNDPVNDRTILYIKPGGCQEFYKSFNIMKNIWIIPERNVIGTTPQDFHP
PTSLKNGDSSYYDPNYLQSDEEKDRFLKIVTKIFNRINNNLSGGILLEELSKANPYLGNDNTPDNKFHIGDASAV
EIKFSKGSQHILLPNVIIMGAEPDLFETNSSNISLRNNYMPSNHGFGSIAIVTFSPEYSFRFNDNSINEFIQDPA
LTLMHELIHSLHGLYGAKGITTTCIITQQKNPLITNRKGINIEEFLTFGGNDLNIITVAQYNDIYTNLLNDYRKI
ASKLSKVQVSNPQLNPYKDIFQEKYGLDKDASGIYSVNINKFDDILKKLYSFTEFDLATKFQVKCRETYIGQYKY
FKLSNLLNDSIYNISEGYNINNLKVNFRGQNANLNPRIIKPITGRGLVKKIIRFAVDKLAAALEHHHHHH

FIGURE 15

(SEQ ID No. 13)

```
ATGCCATTCGTCAACAAGCAATTCAACTACAAAGACCCAGTCAACGGCGTCGACATCGCATACATCAAGATTCCG
AACGCCGGTCAAATGCAGCCGGTTAAGGCTTTTAAGATCCACAACAAGATTTGGGTTATCCCGGAGCGTGACACC
TTCACGAACCCGGAAGAAGGCGATCTGAACCCGCCACCGGAAGCGAAGCAAGTCCCTGTCAGCTACTACGATTCG
ACGTACCTGAGCACGGATAACGAAAAGATAACTACCTGAAAGGTGTGACCAAGCTGTTCGAACGTATCTACAGC
ACGGATCTGGGTCGCATGCTGCTGACTAGCATTGTTCGCGGTATCCCGTTCTGGGGTGGTAGCACGATTGACACC
GAACTGAAGGTTATCGACACTAACTGCATTAACGTTATTCAACCGGATGGTAGCTATCGTAGCGAAGAGCTGAAT
CTGGTCATCATTGGCCCGAGCGCAGACATTATCCAATTCGAGTGCAAGAGCTTTGGTCACGAGGTTCTGAATCTG
ACCCGCAATGGCTATGGTAGCACCCAGTACATTCGTTTTCGCCGGATTTTACCTTCGGCTTTGAAGAGAGCCTG
GAGGTTGATACCAATCCGTTGCTGGGTGCGGGCAAATTCGCTACCGATCCGGCTGTCACGCTGGCCCATGAACTG
ATCCACGCAGGCCACCGCCTGTACGGCATTGCCATCAACCCAAACCGTGTGTTCAAGGTTAATACGAATGCATAC
TACGAGATGAGCGGCCTGGAAGTCAGCTTCGAAGAACTGCGCACCTTCGGTGGCCATGACGCTAAATTCATTGAC
AGCTTGCAAGAGAATGAGTTCCGTCTGTACTACTATAACAAATTCAAAGACATTGCAAGCACGTTGAACAAGGCC
AAAAGCATCGTTGGTACTACCGCGTCGTTGCAGTATATGAAGAATGTGTTTAAAGAGAAGTACCTGCTGTCCGAG
GATACCTCCGGCAAGTTTAGCGTTGATAAGCTGAAGTTTGACAAACTGTACAAGATGCTGACCGAGATTTACACC
GAGGACAACTTTGTGAAATTCTTCAAAGTGTTGAATCGTAAAACCTATCTGAATTTTGACAAAGCGGTTTTCAAG
ATTAACATCGTGCCGAAGGTGAACTACACCATCTATGACGGTTTTAACCTGCGTAACACCAACCTGGCGGCGAAC
TTTAACGGTCAGAATACGGAAATCAACAACATGAATTTCACGAAGTTGAAGAACTTCACGGGTCTGTTCGAGTTC
TATAAGCTGCTGTGCGTGCGCGGTATCATCACCAGCAAAACCAAAAGCCTGGACAAAGGCTACAACAAGGCGCTG
AATGACCTGTGCATTAAGGTAAACAATTGGGATCTGTTCTTTTCGCCATCCGAAGATAATTTTACCAACGACCTG
AACAAGGGTGAAGAAATCACCAGCGATACGAATATTGAAGCAGCGGAAGAGAATATCAGCCTGGATCTGATCCAG
CAGTACTATCTGACCTTTAACTTCGACAATGAACCGGAGAACATTAGCATTGAGAATCTGAGCAGCGACATTATC
GGTCAGCTGGAACTGATGCCGAATATCGAACGTTTCCCGAACGGCAAAAGTACGAGCTGGACAAGTACACTATG
TTCCATTACCTGCGTGCACAGGAGTTTGAACACGGTAAAAGCCGTATCGCGCTGACCAACAGCGTTAACGAGGCC
CTGCTGAACCCGAGCCGTGTCTATACCTTCTTCAGCAGCGACTATGTTAAGAAAGTGAACAAAGCCACTGAGGCC
GCGATGTTCCTGGGCTGGGTGGAACAGCTGGTATATGACTTCACGGACGAGACGAGCGAAGTGAGCACTACCGAC
AAAATTGCTGATATTACCATCATTATCCCGTATATTGGTCCGGCACTGAACATTGGCAACATGCTGTACAAAGAC
GATTTTGTGGGTGCCCTGATCTTCTCCGGTGCCGTGATTCTGCTGGAGTTCATTCCGGAGATTGCGATCCCGGTG
TTGGGTACCTTCGCGCTGGTGTCCTACATCGCGAATAAGGTTCTGACGGTTCAGACCATCGATAACGCGCTGTCG
AAACGTAATGAAAAATGGGACGAGGTTTACAAATACATTGTTACGAATTGGCTGGCGAAAGTCAATACCCAGATC
GACCTGATCCGTAAGAAAATGAAAGAGGCGCTGGAGAATCAGGCGGAGGCCACCAAAGCAATTATCAACTACCAA
TACAACCAGTACACGGAAGAAGAGAAGAATAACATTAACTTCAATATCGATGATTTGAGCAGCAAGCTGAATGAA
TCTATCAACAAAGCGATGATCAATATCAACAAGTTTTTGAATCAGTGTAGCGTTTCGTACCTGATGAATAGCATG
ATTCCGTATGGCGTCAAACGTCTGGAGGACTTCGACGCCAGCCTGAAAGATGCGTTGCTGAAATACATTTACGAC
AATCGTGGTACGCTGATTGGCCAAGTTGACCGCTTGAAAGACAAAGTTAACAATACCCTGAGCACCGACATCCCA
TTTCAACTGAGCAAGTATGTTGATAATCAACGTCTGTTGAGCACTTTCACCGAGTATATCAAAAACATCATCAAT
ACTAGCATTCTGAACCTGCGTTACGAGAGCAATCATCTGATTGATCTGAGCCGTTATGCAAGCAAGATCAACATC
GGTAGCAAGGTCAATTTTGACCCGATCGATAAGAACCAGATCCAGCTGTTTAATCTGGAATCGAGCAAAATTGAG
GTTATCCTGAAAAACGCCATTGTCTACAACTCCATGTACGAGAATTTCTCCACCAGCTTCTGGATTCGCATCCCG
AAATACTTCAACAGCATTAGCCTGAACAACGAGTATACTATCATCAACTGTATGGAGAACAACAGCGGTTGGAAG
GTGTCTCTGAACTATGGTGAGATCATTTGGACCTTGCAGGACACCCAAGAGATCAAGCAGCGCGTCGTGTTCAAG
TACTCTCAAATGATCAACATTTCCGATTACATTAATCGTTGGATCTTCGTGACCATTACGAATAACCGTCTGAAT
AACAGCAAGATTTACATCAATGGTCGCTTGATCGATCAGAAACCGATTAGCAACCTGGGTAATATCCACGCAAGC
AACAACATTATGTTCAAATTGGACGGTTGCCGCGATACCCATCGTTATATCTGGATCAAGTATTTCAACCTGTTT
GATAAAGAACTGAATGAGAAGGAGATCAAAGATTTGTATGACAACCAATCTAACAGCGGCATTTTGAAGGACTTC
TGGGGCGATTATCTGCAATACGATAAGCCGTACTATATGCTGAACCTGTATGATCCGAACAAATATGTGGATGTC
AATAATGTGGGTATTCGTGGTTACATGTATTTGAAGGGTCCGCGTGGCAGCGTTATGACGACCAACATTTACCTG
AACTCTAGCCTGTACCGTGGTACGAAATTCATCATTAAGAAATATGCCAGCGGCAACAAAGATAACATTGTGCGT
AATAACGATCGTGTCTACATCAACGTGGTCGTGAAGAATAAAGAGTACCGTCTGGCGACCAACGCTTCGCAGGCG
GGTGTTGAGAAAATTCTGAGCGCGTTGGAGATCCCTGATGTCGGTAATCTGAGCCAAGTCGTGGTTATGAAGAGC
AAGAACGACCAGGGTATCACTAACAAGTGCAAGATGAACCTGCAAGACAACAATGGTAACGACATCGGCTTTATT
GGTTTCCACCAGTTCAACAATATTGCTAAACTGGTAGCGAGCAATTGGTACAATCGTCAGATTGAGCGCAGCAGC
CGTACTTTGGGCTGTAGCTGGGAGTTTATCCCGGTCGATGATGGTTGGGGCGAACGTCCGCTG
```

FIGURE 16

(SEQ ID No. 14)

```
MPFVNKQFNYKDPVNGVDIAYIKIPNAGQMQPVKAFKIHNKIWVIPERDTFTNPEEGDLNPPPEAKQVPVSYYDS
TYLSTDNEKDNYLKGVTKLFERIYSTDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESLEVDTNPLLGAGKFATDPAVTLAHEL
IHAGHRLYGIAINPNRVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKVLNRKTYLNFDKAVFK
INIVPKVNYTIYDGFNLRNTNLAANFNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQQYYLTFNFDNEPENISIENLSSDII
GQLELMPNIERFPNGKKYELDKYTMFHYLRAQEFEHGKSRIALTNSVNEALLNPSRVYTFFSSDYVKKVNKATEA
AMFLGWVEQLVYDFTDETSEVSTTDKIADITIIIPYIGPALNIGNMLYKDDFVGALIFSGAVILLEFIPEIAIPV
LGTFALVSYIANKVLTVQTIDNALSKRNEKWDEVYKYIVTNWLAKVNTQIDLIRKKMKEALENQAEATKAIINYQ
YNQYTEEEKNNINFNIDDLSSKLNESINKAMININKFLNQCSVSYLMNSMIPYGVKRLEDFDASLKDALLKYIYD
NRGTLIGQVDRLKDKVNNTLSTDIPFQLSKYVDNQRLLSTFTEYIKNIINTSILNLRYESNHLIDLSRYASKINI
GSKVNFDPIDKNQIQLFNLESSKIEVILKNAIVYNSMYENFSTSFWIRIPKYFNSISLNNEYTIINCMENNSGWK
VSLNYGEIIWTLQDTQEIKQRVVFKYSQMINISDYINRWIFVTITNNRLNNSKIYINGRLIDQKPISNLGNIHAS
NNIMFKLDGCRDTHRYIWIKYFNLFDKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRNNDRVYINVVVKNKEYRLATNASQA
GVEKILSALEIPDVGNLSQVVVMKSKNDQGITNKCKMNLQDNNGNDIGFIGFHQFNNIAKLVASNWYNRQIERSS
RTLGCSWEFIPVDDGWGERPL
```

FIGURE 17

(SEQ ID No. 15)

ATGCCATTCGTCAACAAGCAATTCAACTACAAAGACCCAGTCAACGGCGTCGACATCGCATACATCAAGATTCCG
AACGCCGGTCAAATGCAGCCGGTTAAGGCTTTTAAGATCCACAACAAGATTTGGGTTATCCCGGAGCGTGACACC
TTCACGAACCCGGAAGAAGGCGATCTGAACCCGCCACCGGAAGCGAAGCAAGTCCCTGTCAGCTACTACGATTCG
ACGTACCTGAGCACGGATAACGAAAAGATAACTACCTGAAAGGTGTGACCAAGCTGTTCGAACGTATCTACAGC
ACGGATCTGGGTCGCATGCTGCTGACTAGCATTGTTCGCGGTATCCCGTTCTGGGGTGGTAGCACGATTGACACC
GAACTGAAGGTTATCGACACTAACTGCATTAACGTTATTCAACCGGATGGTAGCTATCGTAGCGAAGAGCTGAAT
CTGGTCATCATTGGCCCGAGCGCAGACATTATCCAATTCGAGTGCAAGAGCTTTGGTCACGAGGTTCTGAATCTG
ACCCGCAATGGCTATGGTAGCACCCAGTACATTCGTTTTCGCCGGATTTTACCTTCGGCTTTGAAGAGAGCCTG
GAGGTTGATACCAATCCGTTGCTGGGTGCGGGCAAATTCGCTACCGATCCGGCTGTCACGCTGGCCCATGAACTG
ATCCACGCAGGCCACCGCCTGTACGGCATTGCCATCAACCCAAACCGTGTGTTCAAGGTTAATACGAATGCATAC
TACGAGATGAGCGGCCTGGAAGTCAGCTTCGAAGAACTGCGCACCTTCGGTGGCCATGACGCTAAATTCATTGAC
AGCTTGCAAGAGAATGAGTTCCGTCTGTACTACTATAACAAATTCAAAGACATTGCAAGCACGTTGAACAAGGCC
AAAAGCATCGTTGGTACTACCGCGTCGTTGCAGTATATGAAGAATGTGTTTAAAGAGAAGTACCTGCTGTCCGAG
GATACCTCCGGCAAGTTTAGCGTTGATAAGCTGAAGTTTGACAAACTGTACAAGATGCTGACCGAGATTTACACC
GAGGACAACTTTGTGAAATTCTTCAAAGTGTTGAATCGTAAAACCTATCTGAATTTTGACAAAGCGGTTTTCAAG
ATTAACATCGTGCCGAAGGTGAACTACACCATCTATGACGGTTTTAACCTGCGTAACACCAACCTGGCGGCGAAC
TTTAACGGTCAGAATACGGAAATCAACAACATGAATTTCACGAAGTTGAAGAACTTCACGGGTCTGTTCGAGTTC
TATAAGCTGCTGTGCGTGCGCGGTATCATCACCAGCAAAACCAAAAGCCTGGACAAAGGCTACAACAAGGCGCTG
AATGACCTGTGCATTAAGGTAAACAATTGGGATCTGTTCTTTTCGCCATCCGAAGATAATTTTACCAACGACCTG
AACAAGGGTGAAGAAATCACCAGCGATACGAATATTGAAGCAGCGGAAGAGAATATCAGCCTGGATCTGATCCAG
CAGTACTATCTGACCTTTAACTTCGACAATGAACCGGAGAACATTAGCATTGAGAATCTGAGCAGCGACATTATC
GGTCAGCTGGAACTGATGCCGAATATCGAACGTTTCCCGAACGGCAAAAGTACGAGCTGGACAAGTACACTATG
TTCCATTACCTGCGTGCACAGGAGTTTGAACACGGTAAAAGCCGTATCGCGCTGACCAACAGCGTTAACGAGGCC
CTGCTGAACCCGAGCCGTGTCTATACCTTCTTCAGCAGCGACTATGTTAAGAAAGTGAACAAAGCCACTGAGGCC
GCGATGTTCCTGGGCTGGGTGGAACAGCTGGTATATGACTTCACGGACGAGACGAGCGAAGTGAGCACTACCGAC
AAAATTGCTGATATTACCATCATTATCCCGTATATTGGTCCGGCACTGAACATTGGCAACATGCTGTACAAAGAC
GATTTTGTGGGTGCCCTGATCTTCTCCGGTGCCGTGATTCTGCTGGAGTTCATTCCGGAGATTGCGATCCCGGTG
TTGGGTACCTTCGCGCTGGTGTCCTACATCGCGAATAAGGTTCTGACGGTTCAGACCATCGATAACGCGCTGTCG
AAACGTAATGAAAAATGGGACGAGGTTTACAAATACATTGTTACGAATTGGCTGGCGAAAGTCAATACCCAGATC
GACCTGATCCGTAAGAAAATGAAAGAGGCGCTGGAGAATCAGGCGGAGGCCACCAAAGCAATTATCAACTACCAA
TACAACCAGTACACGGAAGAAGAGAAGAATAACATTAACTTCAATATCGATGATTTGAGCAGCAAGCTGAATGAA
TCTATCAACAAAGCGATGATCAATATCAACAAGTTTTTGAATCAGTGTAGCGTTTCGTACCTGATGAATAGCATG
ATTCCGTATGGCGTCAAACGTCTGGAGGACTTCGACGCCAGCCTGAAAGATGCGTTGCTGAAATACATTTACGAC
AATCGTGGTACGCTGATTGGCCAAGTTGACCGCTTGAAAGACAAAGTTAACAATACCCTGAGCACCGACATCCCA
TTTCAACTGAGCAAGTATGTTGATAATCAACGTCTGTTGAGCACTTTCACCGAGTATATCAAAAACATCATCAAT
ACTAGCATTCTGAACCTGCGTTACGAGAGCAAGCATCTGATTGATCTGAGCCGTTATGCTAGCAAGATCAACATC
GGTAGCAAGGTCAATTTTGACCCGATCGATAAGAACCAGATCCAGCTGTTTAATCTGGAATCGAGCAAAATTGAG
GTTATCCTGAAAAAGGCCATTGTCTACAACTCCATGTACGAGAATTTCTCCACCAGCTTCTGGATTCGCATCCCG
AAATACTTCAACAAGATTAGCCTGAACAACGAGTATACTATCATCAACTGTATGGAGAACAACAGCGGTTGGAAG
GTGTCTCTGAACTATGGTGAGATCATTTGGACCTTGCAGGACACCAAAGAGATCAAGCAGCGCGTCGTGTTCAAG
TACTCTCAAATGATCAACATTTCCGATTACATTAATCGTTGGATCTTCGTGACCATTACGAATAACCGTCTGAAT
AAGAGCAAGATTTACATCAATGGTCGCTTGATCGATCAGAAACCGATTAGCAACCTGGGTAATATCCACGCAAGC
AACAAGATTATGTTCAAATTGGACGGTTGCCGCGATACCCATCGTTATATCTGGATCAAGTATTTCAACCTGTTT
GATAAAGAACTGAATGAGAAGGAGATCAAAGATTTGTATGACAACCAATCTAACAGCGGCATTTTGAAGGACTTC
TGGGGCGATTATCTGCAATACGATAAGCCGTACTATATGCTGAACCTGTATGATCCGAACAAATATGTGGATGTC
AATAATGTGGGTATTCGTGGTTACATGTATTTGAAGGGTCCGCGTGGCAGCGTTATGACGACCAACATTTACCTG
AACTCTAGCCTGTACCGTGGTACGAAATTCATCATTAAGAAATATGCCAGCGGCAACAAAGATAACATTGTGCGT
AATAACGATCGTGTCTACATCAACGTGGTCGTGAAGAATAAAGAGTACCGTCTGGCGACCAACGCTTCGCAGGCG
GGTGTTGAGAAAATTCTGAGCGCGTTGGAGATCCCTGATGTCGGTAATCTGAGCCAAGTCGTGGTTATGAAGAGC
AAGAACGACAAGGGTATCACTAACAAGTGCAAGATGAACCTGCAAGACAACAATGGTAACGACATCGGCTTTATT
GGTTTCCACCAGTTCAACAATATTGCTAAACTGGTAGCGAGCAATTGGTACAATCGTCAGATTGAGCGCAGCAGC
cGTACTTTGGGCTGTAGCTGGGAGTTTATCCCGGTCGATGATGGTTGGGGCGAACGTCCGCTG

FIGURE 18

(SEQ ID No. 16)

```
MPFVNKQFNYKDPVNGVDIAYIKIPNAGQMQPVKAFKIHNKIWVIPERDTFTNPEEGDLNPPPEAKQVPVSYYDS
TYLSTDNEKDNYLKGVTKLFERIYSTDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESLEVDTNPLLGAGKFATDPAVTLAHEL
IHAGHRLYGIAINPNRVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKVLNRKTYLNFDKAVFK
INIVPKVNYTIYDGFNLRNTNLAANFNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQQYYLTFNFDNEPENISIENLSSDII
GQLELMPNIERFPNGKKYELDKYTMFHYLRAQEFEHGKSRIALTNSVNEALLNPSRVYTFFSSDYVKKVNKATEA
AMFLGWVEQLVYDFTDETSEVSTTDKIADITIIIPYIGPALNIGNMLYKDDFVGALIFSGAVILLEFIPEIAIPV
LGTFALVSYIANKVLTVQTIDNALSKRNEKWDEVYKYIVTNWLAKVNTQIDLIRKKMKEALENQAEATKAIINYQ
YNQYTEEEKNNINFNIDDLSSKLNESINKAMININKFLNQCSVSYLMNSMIPYGVKRLEDFDASLKDALLKYIYD
NRGTLIGQVDRLKDKVNNTLSTDIPFQLSKYVDNQRLLSTFTEYIKNIINTSILNLRYESKHLIDLSRYASKINI
GSKVNFDPIDKNQIQLFNLESSKIEVILKKAIVYNSMYENFSTSFWIRIPKYFNKISLNNEYTIINCMENNSGWK
VSLNYGEIIWTLQDTKEIKQRVVFKYSQMINISDYINRWIFVTITNNRLNKSKIYINGRLIDQKPISNLGNIHAS
NKIMFKLDGCRDTHRYIWIKYFNLFDKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRNNDRVYINVVVKNKEYRLATNASQA
GVEKILSALEIPDVGNLSQVVVMKSKNDKGITNKCKMNLQDNNGNDIGFIGFHQFNNIAKLVASNWYNRQIERSS
RTLGCSWEFIPVDDGWGERPL
```

FIGURE 19

(SEQ ID No. 17)

```
ATGCCATTCGTCAACAAGCAATTCAACTACAAAGACCCAGTCAACGGCGTCGACATCGCATACATCAAGATTCCG
AACGCCGGTCAAATGCAGCCGGTTAAGGCTTTTAAGATCCACAACAAGATTTGGGTTATCCCGGAGCGTGACACC
TTCACGAACCCGGAAGAAGGCGATCTGAACCCGCCACCGGAAGCGAAGCAAGTCCCTGTCAGCTACTACGATTCG
ACGTACCTGAGCACGGATAACGAAAAGATAACTACCTGAAAGGTGTGACCAAGCTGTTCGAACGTATCTACAGC
ACGGATCTGGGTCGCATGCTGCTGACTAGCATTGTTCGCGGTATCCCGTTCTGGGGTGGTAGCACGATTGACACC
GAACTGAAGGTTATCGACACTAACTGCATTAACGTTATTCAACCGGATGGTAGCTATCGTAGCGAAGAGCTGAAT
CTGGTCATCATTGGCCCGAGCGCAGACATTATCCAATTCGAGTGCAAGAGCTTTGGTCACGAGGTTCTGAATCTG
ACCCGCAATGGCTATGGTAGCACCCAGTACATTCGTTTTCGCCGGATTTTACCTTCGGCTTTGAAGAGAGCCTG
GAGGTTGATACCAATCCGTTGCTGGGTGCGGGCAAATTCGCTACCGATCCGGCTGTCACGCTGGCCCATGAACTG
ATCCACGCAGGCCACCGCCTGTACGGCATTGCCATCAACCCAAACCGTGTGTTCAAGGTTAATACGAATGCATAC
TACGAGATGAGCGGCCTGGAAGTCAGCTTCGAAGAACTGCGCACCTTCGGTGGCCATGACGCTAAATTCATTGAC
AGCTTGCAAGAGAATGAGTTCCGTCTGTACTACTATAACAAATTCAAAGACATTGCAAGCACGTTGAACAAGGCC
AAAAGCATCGTTGGTACTACCGCGTCGTTGCAGTATATGAAGAATGTGTTTAAAGAGAAGTACCTGCTGTCCGAG
GATACCTCCGGCAAGTTTAGCGTTGATAAGCTGAAGTTTGACAAACTGTACaGATGCTGACCGAGATTTACACC
GAGGACAACTTTGTGAAATTCTTCAAAGTGTTGAATCGTAAAACCTATCTGAATTTTGACAAAGCGGTTTTCAAG
ATTAACATCGTGCCGAAGGTGAACTACACCATCTATGACGGTTTTAACCTGCGTAACACCAACCTGGCGGCGAAC
TTTAACGGTCAGAATACGGAAATCAACAACATGAATTTCACGAAGTTGAAGAACTTCACGGGTCTGTTCGAGTTC
TATAAGCTGCTGTGCGTGCGCGGTATCATCACCAGCAAAACCAAAAGCCTGGACAAAGGCTACAACAAGGCGCTG
AATGACCTGTGCATTAAGGTAAACAATTGGGATCTGTTCTTTTCGCCATCCGAAGATAATTTTACCAACGACCTG
AACAAGGGTGAAGAAATCACCAGCGATACGAATATTGAAGCAGCGGAAGAGAATATCAGCCTGGATCTGATCCAG
CAGTACTATCTGACCTTTAACTTCGACAATGAACCGGAGAACATTAGCATTGAGAATCTGAGCAGCGACATTATC
GGTCAGCTGGAACTGATGCCGAATATCGAACGTTTCCCGAACGGCAAAAGTACGAGCTGGACAAGTACACTATG
TTCCATTACCTGCGTGCACAGGAGTTTGAACACGGTAAAAGCCGTATCGCGCTGACCAACAGCGTTAACGAGGCC
CTGCTGAACCCGAGCCGTGTCTATACCTTCTTCAGCAGCGACTATGTTAAGAAAGTGAACAAAGCCACTGAGGCC
GCGATGTTCCTGGGCTGGGTGGAACAGCTGGTATATGACTTCACGGACGAGACGAGCGAAGTGAGCACTACCGAC
AAAATTGCTGATATTACCATCATTATCCCGTATATTGGTCCGGCACTGAACATTGGCAACATGCTGTACAAAGAC
GATTTTGTGGGTGCCCTGATCTTCTCCGGTGCCGTGATTCTGCTGGAGTTCATTCCGGAGATTGCGATCCCGGTG
TTGGGTACCTTCGCGCTGGTGTCCTACATCGCGAATAAGGTTCTGACGGTTCAGACCATCGATAACGCGCTGTCG
AAACGTAATGAAAAATGGGACGAGGTTTACAAATACATTGTTACGAATTGGCTGGCGAAAGTCAATACCCAGATC
GACCTGATCCGTAAGAAAATGAAAGAGGCGCTGGAGAATCAGGCGGAGGCCACCAAAGCAATTATCAACTACCAA
TACAACCAGTACACGGAAGAAGAGAAGAATAACATTAACTTCAATATCGATGATTTGAGCAGCAAGCTGAATGAA
TCTATCAACAAAGCGATGATCAATATCAACAAGTTTTTGAATCAGTGTAGCGTTTCGTACCTGATGAATAGCATG
ATTCCGTATGGCGTCAAACGTCTGGAGGACTTCGACGCCAGCCTGAAAGATGCGTTGCTGAAATACATTTACGAC
AaTCGTGGTACGCTGATTGGCCAAGTTGACCGCTTGAAAGACAAAGTTAACAATACCCTGAGCACCGACATCCCA
TTTCAACTGAGCAAGTATGTTGATAATCAACGTCTGTTGAGCACTTTCACCGAGTATATCAAAAACATCATCAAT
ACTAGCATTCTGAACCTGCGTTACGAGAGCAATCATCTGATTGATCTGAGCCGTTATGCTAGCAAGATCAACATC
GGTAGCAAGGTCAATTTTGACCCGATCGATAAGAACCAGATCCAGCTGTTTAATCTGGAATCGAGCAAAATTGAG
GTTATCCTGAAAAAGGCCATTGTCTACAACTCCATGTACGAGAATTTCTCCACCAGCTTCTGGATTCGCATCCCG
AAATACTTCAAGAAGATTAGCCTGAACAACGAGTATACTATCATCAACTGTATGGAGAACAACAGCGGTTGGAAG
GTGTCTCTGAACTATGGTGAGATCATTTGGACCTTGCAGGACACCAAAGAGATCAAGCAGCGCGTCGTGTTCAAG
TACTCTCAAATGATCAACATTTCCGATTACATTAATCGTTGGATCTTCGTGACCATTACGAATAACCGTCTGAAT
AAGAGCAAGATTTACATCAATGGTCGCTTGATCGATCAGAAACCGATTAGCAACCTGGGTAATATCCACGCAAGC
AACAAGATTATGTTCAAATTGGACGGTTGCCGCGATACCCATCGTTATATCTGGATCAAGTATTTCAACCTGTTT
GATAAAGAACTGAATGAGAAGGAGATCAAAGATTTGTATGACAACCAATCTAACAGCGGCATTTTGAAGGACTTC
TGGGGCGATTATCTGCAATACGATAAGCCGTACTATATGCTGAACCTGTATGATCCGAACAAATATGTGGATGTC
AATAATGTGGGTATTCGTGGTTACATGTATTTGAAGGGTCCGCGTGGCAGCGTTATGACGACCAACATTTACCTG
AACTCTAGCCTGTACCGTGGTACGAAATTCATCATTAAGAAATATGCCAGCGGCAACAAAGATAACATTGTGCGT
AATAACGATCGTGTCTACATCAACGTGGTCGTGAAGAATAAAGAGTACCGTCTGGCGACCAACGCTTCGCAGGCG
GGTGTTGAGAAAATTCTGAGCGCGTTGGAGATCCCTGATGTCGGTAATCTGAGCCAAGTCGTGGTTATGAAGAGC
AAGAACGACAAGGGTATCACTAACAAGTGCAAGATGAACCTGCAAGACAACAATGGTAACGACATCGGCTTTATT
GGTTTCCACCAGTTCAACAATATTGCTAAACTGGTAGCGAGCAATTGGTACAATCGTCAGATTGAGCGCAGCAGC
CGTACTTTGGGCTGTAGCTGGGAGTTTATCCCGGTCGATGATGGTTGGGGCGAACGTCCGCTG
```

FIGURE 20

(SEQ ID No. 18)

```
MPFVNKQFNYKDPVNGVDIAYIKIPNAGQMQPVKAFKIHNKIWVIPERDTFTNPEEGDLNPPPEAKQVPVSYYDS
TYLSTDNEKDNYLKGVTKLFERIYSTDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESLEVDTNPLLGAGKFATDPAVTLAHEL
IHAGHRLYGIAINPNRVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKVLNRKTYLNFDKAVFK
INIVPKVNYTIYDGFNLRNTNLAANFNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQQYYLTFNFDNEPENISIENLSSDII
GQLELMPNIERFPNGKKYELDKYTMFHYLRAQEFEHGKSRIALTNSVNEALLNPSRVYTFFSSDYVKKVNKATEA
AMFLGWVEQLVYDFTDETSEVSTTDKIADITIIIPYIGPALNIGNMLYKDDFVGALIFSGAVILLEFIPEIAIPV
LGTFALVSYIANKVLTVQTIDNALSKRNEKWDEVYKYIVTNWLAKVNTQIDLIRKKMKEALENQAEATKAIINYQ
YNQYTEEEKNNINFNIDDLSSKLNESINKAMININKFLNQCSVSYLMNSMIPYGVKRLEDFDASLKDALLKYIYD
NRGTLIGQVDRLKDKVNNTLSTDIPFQLSKYVDNQRLLSTFTEYIKNIINTSILNLRYESNHLIDLSRYASKINI
GSKVNFDPIDKNQIQLFNLESSKIEVILKKAIVYNSMYENFSTSFWIRIPKYFKKISLNNEYTIINCMENNSGWK
VSLNYGEIIWTLQDTKEIKQRVVFKYSQMINISDYINRWIFVTITNNRLNKSKIYINGRLIDQKPISNLGNIHAS
NKIMFKLDGCRDTHRYIWIKYFNLFDKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRNNDRVYINVVVKNKEYRLATNASQA
GVEKILSALEIPDVGNLSQVVVMKSKNDKGITNKCKMNLQDNNGNDIGFIGFHQFNNIAKLVASNWYNRQIERSS
RTLGCSWEFIPVDDGWGERPL
```

FIGURE 21

(SEQ ID No. 19)

```
ATGCCATTCGTCAACAAGCAATTCAACTACAAAGACCCAGTCAACGGCGTCGACATCGCATACATCAAGATTCCG
AACGCCGGTCAAATGCAGCCGGTTAAGGCTTTTAAGATCCACAACAAGATTTGGGTTATCCCGGAGCGTGACACC
TTCACGAACCCGGAAGAAGGCGATCTGAACCCGCCACCGGAAGCGAAGCAAGTCCCTGTCAGCTACTACGATTCG
ACGTACCTGAGCACGGATAACGAAAAGATAACTACCTGAAAGGTGTGACCAAGCTGTTCGAACGTATCTACAGC
ACGGATCTGGGTCGCATGCTGCTGACTAGCATTGTTCGCGGTATCCCGTTCTGGGGTGGTAGCACGATTGACACC
GAACTGAAGGTTATCGACACTAACTGCATTAACGTTATTCAACCGGATGGTAGCTATCGTAGCGAAGAGCTGAAT
CTGGTCATCATTGGCCCGAGCGCAGACATTATCCAATTCGAGTGCAAGAGCTTTGGTCACGAGGTTCTGAATCTG
ACCCGCAATGGCTATGGTAGCACCCAGTACATTCGTTTTCGCCGGATTTTACCTTCGGCTTTGAAGAGAGCCTG
GAGGTTGATACCAATCCGTTGCTGGGTGCGGGCAAATTCGCTACCGATCCGGCTGTCACGCTGGCCCATGAACTG
ATCCACGCAGGCCACCGCCTGTACGGCATTGCCATCAACCCAAACCGTGTGTTCAAGGTTAATACGAATGCATAC
TACGAGATGAGCGGCCTGGAAGTCAGCTTCGAAGAACTGCGCACCTTCGGTGGCCATGACGCTAAATTCATTGAC
AGCTTGCAAGAGAATGAGTTCCGTCTGTACTACTATAACAAATTCAAAGACATTGCAAGCACGTTGAACAAGGCC
AAAAGCATCGTTGGTACTACCGCGTCGTTGCAGTATATGAAGAATGTGTTTAAAGAGAAGTACCTGCTGTCCGAG
GATACCTCCGGCAAGTTTAGCGTTGATAAGCTGAAGTTTGACAAACTGTACAAGATGCTGACCGAGATTTACACC
GAGGACAACTTTGTGAAATTCTTCAAAGTGTTGAATCGTAAAACCTATCTGAATTTTGACAAAGCGGTTTTCAAG
ATTAACATCGTGCCGAAGGTGAACTACACCATCTATGACGGTTTTAACCTGCGTAACACCAACCTGGCGGCGAAC
TTTAACGGTCAGAATACGGAAATCAACAACATGAATTTCACGAAGTTGAAGAACTTCACGGGTCTGTTCGAGTTC
TATAAGCTGCTGTGCGTGCGCGGTATCATCACCAGCAAAACCAAAAGCCTGGACAAAGGCTACAACAAGGCGCTG
AATGACCTGTGCATTAAGGTAAACAATTGGGATCTGTTCTTTTCGCCATCCGAAGATAATTTTACCAACGACCTG
AACAAGGGTGAAGAAATCACCAGCGATACGAATATTGAAGCAGCGGAAGAGAATATCAGCCTGGATCTGATCCAG
CAGTACTATCTGACCTTTAACTTCGACAATGAACCGGAGAACATTAGCATTGAGAATCTGAGCAGCGACATTATC
GGTCAGCTGGAACTGATGCCGAATATCGAACGTTTCCCGAACGGCAAAAGTACGAGCTGGACAAGTACACTATG
TTCCATTACCTGCGTGCACAGGAGTTTGAACACGGTAAAAGCCGTATCGCGCTGACCAACAGCGTTAACGAGGCC
CTGCTGAACCCGAGCCGTGTCTATACCTTCTTCAGCAGCGACTATGTTAAGAAAGTGAACAAAGCCACTGAGGCC
GCGATGTTCCTGGGCTGGGTGGAACAGCTGGTATATGACTTCACGGACGAGACGAGCGAAGTGAGCACTACCGAC
AAAATTGCTGATATTACCATCATTATCCCGTATATTGGTCCGGCACTGAACATTGGCAACATGCTGTACAAAGAC
GATTTTGTGGGTGCCCTGATCTTCTCCGGTGCCGTGATTCTGCTGGAGTTCATTCCGGAGATTGCGATCCCGGTG
TTGGGTACCTTCGCGCTGGTGTCCTACATCGCGAATAAGGTTCTGACGGTTCAGACCATCGATAACGCGCTGTCG
AAACGTAATGAAAAATGGGACGAGGTTTACAAATACATTGTTACGAATTGGCTGGCGAAAGTCAATACCCAGATC
GACCTGATCCGTAAGAAAATGAAAGAGGCGCTGGAGAATCAGGCGGAGGCCACCAAAGCAATTATCAACTACCAA
TACAACCAGTACACGGAAGAAGAGAAGAATAACATTAACTTCAATATCGATGATTTGAGCAGCAAGCTGAATGAA
TCTATCAACAAAGCGATGATCAATATCAACAAGTTTTGAATCAGTGTAGCGTTTCGTACCTGATGAATAGCATG
ATTCCGTATGGCGTCAAACGTCTGGAGGACTTCGACGCCAGCCTGAAAGATGCGTTGCTGAAATACATTTACGAC
AATCGTGGTACGCTGATTGGCCAAGTTGACCGCTTGAAAGACAAAGTTAACAATACCCTGAGCACCGACATCCCA
TTTCAACTGAGCAAGTATGTTGATAATCAACGTCGTTGAGCACTTTCACCGAGTATATCAAAAACATCATCAAT
ACTAGCATTCTGAACCTGCGTTACGAGAGCAATCATCTGATTGATCTGAGCCGTTATGCTAGCAAGATCAACATC
GGTAGCAAGGTCAATTTTGACCCGATCGATAAGAACCAGATCCAGCTGTTTAATCTGGAATCGAGCAAAATTGAG
GTTATCCTGAAAAAGGCCATTGTCTACAACTCCATGTACGAGAATTTCTCCACCAGCTTCTGGATTCGCATCCCG
AAATACTTCAACAAGATTAGCCTGAACAACGAGTATACTATCATCAACTGTATGGAGAACAACAGCGGTTGGAAG
GTGTCTCTGAACTATGGTGAGATCATTTGGACCTTGCAGGACACCAAAGAGATCAAGCAGCGCGTCGTGTTCAAG
TACTCTCAAATGATCAACATTTCCGATTACATTAATCGTTGGATCTTCGTGACCATTACGAATAACCGTCTGAAG
AAGAGCAAGATTTACATCAATGGTCGCTTGATCGATCAGAAACCGATTAGCAACCTGGGTAATATCCACGCAAGC
AACAAGATTATGTTCAAATTGGACGGTTGCCGCGATACCCATCGTTATATCTGGATCAAGTATTTCAACCTGTTT
GATAAAGAACTGAATGAGAAGGAGATCAAAGATTTGTATGACAACCAATCTAACAGCGGCATTTTGAAGGACTTC
TGGGGCGATTATCTGCAATACGATAAGCCGTACTATATGCTGAACCTGTATGATCCGAACAAATATGTGGATGTC
AATAATGTGGGTATTCGTGGTTACATGTATTTGAAGGGTCCGCGTGGCAGCGTTATGACGACCAACATTTACCTG
AACTCTAGCCTGTACCGTGGTACGAAATTCATCATTAAGAAATATGCCAGCGGCAACAAAGATAACATTGTGCGT
AATAACGATCGTGTCTACATCAACGTGGTCGTGAAGAATAAAGAGTACCGTCTGGCGACCAACGCTTCGCAGGCG
GGTGTTGAGAAATTCTGAGCGCGTTGGAGATCCCTGATGTCGGTAATCTGAGCCAAGTCGTGGTTATGAAGAGC
AAGAACGACAAGGGTATCACTAACAAGTGCAAGATGAACCTGCAAGACAACAATGGTAACGACATCGGCTTTATT
GGTTTCCACCAGTTCAACAATATTGCTAAACTGGTAGCGAGCAATTGGTACAATCGTCAGATTGAGCGCAGCAGC
CGTACTTTGGGCTGTAGCTGGGAGTTTATCCCGGTCGATGATGGTTGGGGCGAACGTCCGCTG
```

FIGURE 22

(SEQ ID No. 20)

MPFVNKQFNYKDPVNGVDIAYIKIPNAGQMQPVKAFKIHNKIWVIPERDTFTNPEEGDLNPPPEAKQVPVSYYDS
TYLSTDNEKDNYLKGVTKLFERIYSTDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESLEVDTNPLLGAGKFATDPAVTLAHEL
IHAGHRLYGIAINPNRVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKVLNRKTYLNFDKAVFK
INIVPKVNYTIYDGFNLRNTNLAANFNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQQYYLTFNFDNEPENISIENLSSDII
GQLELMPNIERFPNGKKYELDKYTMFHYLRAQEFEHGKSRIALTNSVNEALLNPSRVYTFFSSDYVKKVNKATEA
AMFLGWVEQLVYDFTDETSEVSTTDKIADITIIIPYIGPALNIGNMLYKDDFVGALIFSGAVILLEFIPEIAIPV
LGTFALVSYIANKVLTVQTIDNALSKRNEKWDEVYKYIVTNWLAKVNTQIDLIRKKMKEALENQAEATKAIINYQ
YNQYTEEEKNNINFNIDDLSSKLNESINKAMININKFLNQCSVSYLMNSMIPYGVKRLEDFDASLKDALLKYIYD
NRGTLIGQVDRLKDKVNNTLSTDIPFQLSKYVDNQRLLSTFTEYIKNIINTSILNLRYESNHLIDLSRYASKINI
GSKVNFDPIDKNQIQLFNLESSKIEVILKKAIVYNSMYENFSTSFWIRIPKYFNKISLNNEYTIINCMENNSGWK
VSLNYGEIIWTLQDTKEIKQRVVFKYSQMINISDYINRWIFVTITNNRLKKSKIYINGRLIDQKPISNLGNIHAS
NKIMFKLDGCRDTHRYIWIKYFNLFDKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRNNDRVYINVVVKNKEYRLATNASQA
GVEKILSALEIPDVGNLSQVVVMKSKNDKGITNKCKMNLQDNNGNDIGFIGFHQFNNIAKLVASNWYNRQIERSS
RTLGCSWEFIPVDDGWGERPL

FIGURE 23

(SEQ ID No. 21)

```
ATGCCATTCGTCAACAAGCAATTCAACTACAAAGACCCAGTCAACGGCGTCGACATCGCATACATCAAGATTCCG
AACGCCGGTCAAATGCAGCCGGTTAAGGCTTTTAAGATCCACAACAAGATTTGGGTTATCCCGGAGCGTGACACC
TTCACGAACCCGGAAGAAGGCGATCTGAACCCGCCACCGGAAGCGAAGCAAGTCCCTGTCAGCTACTACGATTCG
ACGTACCTGAGCACGGATAACGAAAAGATAACTACCTGAAAGGTGTGACCAAGCTGTTCGAACGTATCTACAGC
ACGGATCTGGGTCGCATGCTGCTGACTAGCATTGTTCGCGGTATCCCGTTCTGGGGTGGTAGCACGATTGACACC
GAACTGAAGGTTATCGACACTAACTGCATTAACGTTATTCAACCGGATGGTAGCTATCGTAGCGAAGAGCTGAAT
CTGGTCATCATTGGCCCGAGCGCAGACATTATCCAATTCGAGTGCAAGAGCTTTGGTCACGAGGTTCTGAATCTG
ACCCGCAATGGCTATGGTAGCACCCAGTACATTCGTTTTCGCCGGATTTTACCTTCGGCTTTGAAGAGAGCCTG
GAGGTTGATACCAATCCGTTGCTGGGTGCGGGCAAATTCGCTACCGATCCGGCTGTCACGCTGGCCCATGAACTG
ATCCACGCAGGCCACCGCCTGTACGGCATTGCCATCAACCCAAACCGTGTGTTCAAGGTTAATACGAATGCATAC
TACGAGATGAGCGGCCTgGAAGTCAGCTTCGAAGAACTGCGCACCTTCGGTGGCCATGACGCTAAATTCATTGAC
AGCTTGCAAGAGAATGAGTTCCGTCTGTACTACTATAACAAATTCAAAGACATTGCAAGCACGTTGAACAAGGCC
AAAAGCATCGTTGGTACTACCGCGTCGTTGCAGTATATGAAGAATGTGTTTAAAGAGAAGTACCTGCTGTCCGAG
GATACCTCCGGCAAGTTTAGCGTTGATAAGCTGAAGTTTGACAAACTGTACAAGATGCTGACCGAGATTTACACC
GAGGACAACTTTGTGAAATTCTTCAAaGTGTTGAATCGTAAAACCTATCTGAATTTTGACAAAGCGGTTTTCaAG
ATTAACATCGTGCCGAAGGTGAACTACACCATCTATGACGGTTTTAACCTGCGTAACACCAACCTGGCGGCGAAC
TTTAACGGTCAGAATACGGAAATCAACAACATGAATTTCACGAAGTTGAAGAACTTCACGGGTCTGTTCGAGTTC
TATAAGCTGCTGTGCGTGCGCGGTATCATCACCAGCAAAACCAAAAGCCTGGACAAAGGCTACAACAAGGCGCTG
AATGACCTGTGCATTAAGGTAAACAATTGGGATCTGTTCTTTTCGCCATCCGAAGATAATTTTACCAACGACCTG
AACAAGGGTGAAGAAATCACCAGCGATACGAATATTGAAGCAGCGGAAGAGAATATCAGCCTGGATCTGATCCAG
CAGTACTATCTGACCTTTAACTTCGACAATGAACCGGAGAACATTAGCATTGAGAATCTGAGCAGCGACATTATC
GGTCAGCTGGAACTGATGCCGAATATCGAACGTTTCCCGAACGGCAAAAGTACGAGCTGGACAAGTACACTATG
TTCCATTACCTGCGTGCACAGGAGTTTGAACACGGTAAAAGCCGTATCGCGCTGACCAACAGCGTTAACGAGGCC
CTGCTGAACCCGAGCCGTGTCTATACCTTCTTCAGCAGCGACTATGTTAAGAAAGTGAACAAAGCCACTGAGGCC
GCGATGTTCCTGGGCTGGGTGGAACAGCTGGTATATGACTTCACGGACGAGACGAGCGAAGTGAGCACTACCGAC
AAAaTTGCTGATaTTACCATCATTATCCCGTATATTGGTCCGGCACTGAACATTGGCAACATGCTGTACAAAGAC
GATTTTGTGGGTGCCCTGATCTTCTCCGGTGCCGTGATTCTGCTGGAGTTCATTCCGGAGATTGCGATCCCGGTG
TTGGGTACCTTCGCGCTGGTGTCCTACATCGCGAATAAGGTTCTGACGGTTCAGACCATCGATAACGCGCTGTCG
AAACGTAATGAAAAATGGGACGAGGTTTACAAATACATTGTTACGAATTGGCTGGCGAAAGTCaATACCCAGATC
GACCTGATCCGTAAGAAAATGAAAGAGGCGCTGGAGAATCAGGCGGAGGCCACCAAAGCAATTATCAACTACCAA
TACAACCAGTACACGGAAGAAGAGAAGAATAACATTAACTTCAATATCGATGATTTGAGCAGCAAGCTGAATGAA
TCTATCAACAAAGCGATGATCAATATCAACAAGTTTTTGAATCAGTGTAGCGTTTCGTACCTGATGAATAGCATG
ATTCCGTATGGCGTCAAACGTCTGGAGGACTTCGACGCCAGCCTGAAAGATGCGTTGCTGAAATACATTTACGAC
AATCGTGGTACGCTGATTGGCCAAGTTGACCGCTTGAAAGACAAAGTTAACAATACCCTGAGCACCGACATCCCA
TTTCAACTGAGCAAGTATGTTGATAATCAACGTCTGTTGAGCACTTTCACCGAGTATATCAAAAACATCATCAAT
ACTAGCATTCTGAACCTGCGTTACGAGAGCAATCATCTGATtGATCTGAGCCGTTATGCAAGCAAGATCAACATC
GGTAGCAAGGTCAATTTTGACCCGATCGATAAGAACCAGATCCAGCTGTTTAATCTGGAATCGAGCAAAATTGAG
GTTATCCTGAAAAACGCCATTGTCTACAACTCCATGTACGAGAATTTCTCCACCAGCTTCTGGATTCGCATCCCG
AAATACTTCAACAGCATTAGCCTGAACAACGAGTATACTATCATCAACTGTATGGAGAACAACAGCGGTTGGAAG
GTGTCTCTGAACTATGGTGAGATCATTTGGACCTTGCAGGACACCCAAGAGATCAAGCAGCGCGTCGTGTTCAAG
TACTCTCAAATGATCAACATTTCCGATTACATTAATCGTTGGATCTTCGTGACCATTACGAATAACCGTCTGAAT
AACAGCAAGATTTACATCAATGGTCGCTTGATCGATCAGAAACCGATTAGCAACCTGGGTAATATCCACGCAAGC
AACAACATTATGTTCAAATTGGACGGTTGCCGCGATACCCATCGTTATATCTGGATCAAGTATTTCAACCTGTTT
GATAAAGAACTGAATGAGAAGGAGATCAAAGATTTGTATGACAACCAATCTAACAGCGGCATTTTGAAGGACTTC
TGGGGCGATTATCTGCAATACGATAAGCCGTACTATATGCTGAACCTGTATGATCCGAACAAATATGTGGATGTC
AATAATGTGGGTATTCGTGGTTACATGTATTTGAAGGGTCCGCGTGGCAGCGTTATGACGACCAACATTTACCTG
AACTCTAGCCTGTACCGTGGTACGAAATTCATCATTAAGAAATATGCCAGCGGCAACAAAGATAACATTGTGCGT
AATAACGATCGTGTCTACATCAACGTGGTCGTGAAGCGTAAAGAGTACCGTCTGGCGACCAACGCTTCGCAGGCG
GGTGTTGAGAAAATTCTGAGCGCGTTGGAGATCCCTCGTGTCCGTCGTCTGAGCCAAGTCGTGGTTATGAAGAGC
AAGAACGACCAGGGTATCACTAACAAGTGCAAGATGAACCTGCAAGACCGTCGTGGTAACGACATCGGCTTTATT
GGTTTCCACCAGTTCAACAATATTGCTAAACTGGTAGCGAGCAATTGGTACAATCGTCAGATTGAGCGCCGTAGC
CGTCGTTTGGGCTGTAGCTGGGAGTTTATCCCGGTCGATGATGGTTGGGGCGAACGTCCGCTG
```

FIGURE 24

(SEQ ID No. 22)

```
MPFVNKQFNYKDPVNGVDIAYIKIPNAGQMQPVKAFKIHNKIWVIPERDTFTNPEEGDLNPPPEAKQVPVSYYDS
TYLSTDNEKDNYLKGVTKLFERIYSTDLGRMLLTSIVRGIPFWGGSTIDTELKVIDTNCINVIQPDGSYRSEELN
LVIIGPSADIIQFECKSFGHEVLNLTRNGYGSTQYIRFSPDFTFGFEESLEVDTNPLLGAGKFATDPAVTLAHEL
IHAGHRLYGIAINPNRVFKVNTNAYYEMSGLEVSFEELRTFGGHDAKFIDSLQENEFRLYYYNKFKDIASTLNKA
KSIVGTTASLQYMKNVFKEKYLLSEDTSGKFSVDKLKFDKLYKMLTEIYTEDNFVKFFKVLNRKTYLNFDKAVFK
INIVPKVNYTIYDGFNLRNTNLAANFNGQNTEINNMNFTKLKNFTGLFEFYKLLCVRGIITSKTKSLDKGYNKAL
NDLCIKVNNWDLFFSPSEDNFTNDLNKGEEITSDTNIEAAEENISLDLIQQYYLTFNFDNEPENISIENLSSDII
GQLELMPNIERFPNGKKYELDKYTMFHYLRAQEFEHGKSRIALTNSVNEALLNPSRVYTFFSSDYVKKVNKATEA
AMFLGWVEQLVYDFTDETSEVSTTDKIADITIIIPYIGPALNIGNMLYKDDFVGALIFSGAVILLEFIPEIAIPV
LGTFALVSYIANKVLTVQTIDNALSKRNEKWDEVYKYIVTNWLAKVNTQIDLIRKKMKEALENQAEATKAIINYQ
YNQYTEEEKNNINFNIDDLSSKLNESINKAMININKFLNQCSVSYLMNSMIPYGVKRLEDFDASLKDALLKYIYD
NRGTLIGQVDRLKDKVNNTLSTDIPFQLSKYVDNQRLLSTFTEYIKNIINTSILNLRYESNHLIDLSRYASKINI
GSKVNFDPIDKNQIQLFNLESSKIEVILKNAIVYNSMYENFSTSFWIRIPKYFNSISLNNEYTIINCMENNSGWK
VSLNYGEIIWTLQDTQEIKQRVVFKYSQMINISDYINRWIFVTITNNRLNNSKIYINGRLIDQKPISNLGNIHAS
NNIMFKLDGCRDTHRYIWIKYFNLFDKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVRNNDRVYINVVVKRKEYRLATNASQA
GVEKILSALEIPRVRRLSQVVVMKSKNDQGITNKCKMNLQDRRGNDIGFIGFHQFNNIAKLVASNWYNRQIERRS
RRLGCSWEFIPVDDGWGERPL
```

METHODS FOR PURIFYING CLOSTRIDIAL NEUROTOXIN

The present application is a national stage filing of International Application No. PCT/EP2016/072986, filed Sep. 27, 2016, which claims the priority benefit of United Kingdom Application No. GB 1517450.1, filed Oct. 2, 2015, the contents of each of which are incorporated by reference in their entireties.

The instant application contains a Sequence Listing that has been submitted electronically in ASCII format and is hereby incorporated by reference in its entirety. Said ASCII copy, created on Sep. 12, 2018, is named 15765427SeqList.txt and is 176,791 bytes in size.

FIELD OF THE INVENTION

The present invention relates to a method of purifying clostridial neurotoxins, uses of a buffer, purification intermediates and clostridial neurotoxins obtained by the methods and uses herein.

BACKGROUND

Bacteria in the genus *Clostridia* produce highly potent and specific protein toxins, which can poison neurons and other cells to which they are delivered. Examples of such clostridial toxins include the neurotoxins produced by *C. tetani* (TeNT) and by *C. botulinum* (BoNT) serotypes A-G, as well as those produced by *C. baratii* and *C. butyricum*.

Among the clostridial neurotoxins are some of the most potent toxins known. By way of example, botulinum neurotoxins have median lethal dose ($LD_{50}$) values for mice ranging from 0.5 to 5 ng/kg, depending on the serotype. Both tetanus and botulinum toxins act by inhibiting the function of affected neurons, specifically the release of neurotransmitters. While botulinum toxin acts at the neuromuscular junction and inhibits cholinergic transmission in the peripheral nervous system, tetanus toxin acts in the central nervous system.

In nature, clostridial neurotoxins are synthesised as a single-chain polypeptide that is modified post-translationally by a proteolytic cleavage event to form two polypeptide chains joined together by a disulphide bond. Cleavage occurs at a specific cleavage site, often referred to as the activation site that is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises an N-terminal translocation component ($H_N$ domain) and a C-terminal targeting component ($H_C$ domain). The cleavage site is located between the L-chain and the translocation domain components. Following binding of the $H_C$ domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Non-cytotoxic proteases act by proteolytically cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle fusion, and thus to secretion of molecules via vesicle transport from a cell. The protease function is a zinc-dependent endopeptidase activity and exhibits a high substrate specificity for SNARE proteins. Accordingly, once delivered to a desired target cell, the non-cytotoxic protease is capable of inhibiting cellular secretion from the target cell. The L-chain proteases of clostridial neurotoxins are non-cytotoxic proteases that cleave SNARE proteins.

In view of the ubiquitous nature of SNARE proteins, clostridial neurotoxins such as botulinum toxin have been successfully employed in a wide range of therapies.

By way of example, we refer to William J. Lipham, Cosmetic and Clinical Applications of Botulinum Toxin (Slack, Inc., 2004), which describes the use of clostridial neurotoxins, such as botulinum neurotoxins (BoNTs), BoNT/A, BoNT/B, BoNT/$C_1$, BoNT/D, BoNT/E, BoNT/F and BoNT/G, and tetanus neurotoxin (TeNT), to inhibit neuronal transmission in a number of therapeutic and cosmetic or aesthetic applications—for example, marketed botulinum toxin products are currently approved as therapeutics for indications including focal spasticity, upper limb spasticity, lower limb spasticity, cervical dystonia, blepharospasm, hemifacial spasm, hyperhidrosis of the axillae, chronic migraine, neurogenic detrusor overactivity, glabellar lines, and severe lateral canthal lines. In addition, clostridial neurotoxin therapies are described for treating neuromuscular disorders (see U.S. Pat. No. 6,872,397); for treating uterine disorders (see US 2004/0175399); for treating ulcers and gastroesophageal reflux disease (see US 2004/0086531); for treating dystonia (see U.S. Pat. No. 6,319,505); for treating eye disorders (see US 2004/0234532); for treating blepharospasm (see US 2004/0151740); for treating strabismus (see US 2004/0126396); for treating pain (see U.S. Pat. Nos. 6,869,610, 6,641,820, 6,464,986, and 6,113,915); for treating fibromyalgia (see U.S. Pat. No. 6,623,742, US 2004/0062776); for treating lower back pain (see US 2004/0037852); for treating muscle injuries (see U.S. Pat. No. 6,423,319); for treating sinus headache (see U.S. Pat. No. 6,838,434); for treating tension headache (see U.S. Pat. No. 6,776,992); for treating headache (see U.S. Pat. No. 6,458,365); for reduction of migraine headache pain (see U.S. Pat. No. 5,714,469); for treating cardiovascular diseases (see U.S. Pat. No. 6,767,544); for treating neurological disorders such as Parkinson's disease (see U.S. Pat. Nos. 6,620,415, 6,306,403); for treating neuropsychiatric disorders (see US 2004/0180061, US 2003/0211121); for treating endocrine disorders (see U.S. Pat. No. 6,827,931); for treating thyroid disorders (see U.S. Pat. No. 6,740,321); for treating cholinergic influenced sweat gland disorders (see U.S. Pat. No. 6,683,049); for treating diabetes (see U.S. Pat. Nos. 6,337,075, 6,416,765); for treating a pancreatic disorder (see U.S. Pat. Nos. 6,261,572, 6,143,306); for treating cancers such as bone tumours (see U.S. Pat. Nos. 6,565,870, 6,368,605, 6,139,845, US 2005/0031648); for treating otic disorders (see U.S. Pat. Nos. 6,358,926, 6,265,379); for treating autonomic disorders such as gastrointestinal muscle disorders and other smooth muscle dysfunction (see U.S. Pat. No. 5,437,291); for treatment of skin lesions associated with cutaneous cell-proliferative disorders (see U.S. Pat. No. 5,670,484); for management of neurogenic inflammatory disorders (see U.S. Pat. No. 6,063,768); for reducing hair loss and stimulating hair growth (see U.S. Pat. No. 6,299,893); for treating downturned mouth (see U.S. Pat. No. 6,358,917); for reducing appetite (see US 2004/40253274); for dental therapies and procedures (see US 2004/0115139);

for treating neuromuscular disorders and conditions (see US 2002/0010138); for treating various disorders and conditions and associated pain (see US 2004/0013692); for treating conditions resulting from mucus hypersecretion such as asthma and COPD (see WO 00/10598); and for treating non-neuronal conditions such as inflammation, endocrine conditions, exocrine conditions, immunological conditions, cardiovascular conditions, bone conditions (see WO 01/21213). All of the above publications are hereby incorporated by reference in their entirety.

The use of non-cytotoxic proteases such as clostridial neurotoxins (e.g. BoNTs and TeNT) in therapeutic and cosmetic treatments of humans and other mammals is anticipated to expand to an ever-widening range of diseases and ailments that can benefit from the properties of these toxins.

To avoid systemic neurological effects, many clostridial neurotoxin therapies utilise direct administration of the clostridial neurotoxin therapeutic to a given target site (such as a target tissue). A problem when administering clostridial neurotoxin-based therapeutics in this fashion is the spread of toxin away from the administration site and into surrounding tissue or systemic circulation. The diffusion of toxin away from the target tissue is believed to be responsible for undesirable side effects that in extreme cases may be life threatening. This can be a particular concern when using clostridial neurotoxin therapeutics (such as BoNT therapeutics) at high doses, concentrations and injection volumes. Adverse effects associated with this problem that have been reported for commercial BoNT/A therapeutics include asthenia, generalised muscle weakness, diplopia, ptosis, dysphagia, dysphonia, dysarthria, urinary incontinence, and breathing difficulties. Swallowing and breathing difficulties can be life threatening and there have been reported deaths related to the spread of toxin effects. These problems have been addressed and solved in WO2015/004461 A1 (incorporated herein by reference) which provided engineered clostridial neurotoxins comprising at least one amino acid modification which increases the isoelectric point (pI) of the engineered clostridial neurotoxin.

Methods of purifying clostridial neurotoxins are provided in the art. WO2006/096163 A1 (which is incorporated herein by reference) teaches chromatographic processes and systems for purifying botulinum neurotoxin type A complexed with stabilising non-toxic proteins. WO2006/096163 A1 teaches a plurality of chromatographic processes, including the use of a cation exchange column as a finishing column (i.e. a column used when botulinum neurotoxin type A complex has already been subjected to one or more previous columns and is in a substantially pure state). It is taught in WO2006/096163 A1 to use very low pH values (e.g. pH 4.0) when binding and conducting cation exchange chromatography with botulinum neurotoxin type A complex.

However, there still exists a need for optimised and enhanced techniques for purifying clostridial neurotoxins (especially non-complexed clostridial neurotoxins), which provide an improved process and/or improved yields, preferably facilitating purification of clostridial neurotoxins in fewer (and/or optionally more efficient) steps.

SUMMARY OF THE INVENTION

According to a first aspect the present invention provides a method for purifying a clostridial neurotoxin comprising contacting a cation exchange resin with a composition comprising a clostridial neurotoxin, wherein the contacting step is performed at at least pH 7.3, wherein said step of contacting a cation exchange resin with a composition comprising said clostridial neurotoxin occurs prior to conversion of said clostridial neurotoxin from a single chain form into a dichain form.

In a second aspect there is provided a purification intermediate comprising a clostridial neurotoxin associated with a cation exchange resin, wherein the purification intermediate has a pH value of at least pH 7.3, and wherein said clostridial neurotoxin is in a single chain form In a third aspect there is provided a clostridial neurotoxin which has been separated from a cation exchange resin, wherein the purification intermediate has a pH value of at least pH 7.3, and wherein said clostridial neurotoxin is in a single chain form.

In a fourth aspect the invention provides the use of a buffer having a pH value that is −1 pH unit or higher than the calculated pI of a clostridial neurotoxin for contacting a composition comprising the clostridial neurotoxin with a cation exchange resin for increased binding and/or yield of the clostridial neurotoxin, when compared to using a pH more than −1 pH units lower than the calculated pI of said clostridial neurotoxin under identical conditions, and wherein said clostridial neurotoxin is in a single chain form.

In a fifth aspect there is provided a clostridial neurotoxin obtainable by the method or use of any one of the preceding claims and/or isolated from a purification intermediate of the invention.

BRIEF DESCRIPTION OF THE DRAWINGS

Embodiments of the invention will now be described, by way of example only, with reference to accompanying drawings, in which:

FIG. 3 shows the cationic BoNT/A1 (e.g. a BoNT/A1 having an increased isoelectric point when compared to native BoNT/A1) nucleotide sequence (SEQ ID No. 1).

FIG. 4 shows the cationic rBoNT/A1 polypeptide sequence (SEQ ID No. 2).

FIG. 5 shows the rBoNT/A1 nucleotide sequence (SEQ ID No. 3).

FIG. 6 shows the rBoNT/A1 polypeptide sequence (SEQ ID No. 4).

FIG. 7 shows a cationic BoNT/A, "CatH$_N$_v1", nucleotide sequence (SEQ ID No. 5).

FIG. 8 shows a cationic BoNT/A, "CatH$_N$_v1", polypeptide sequence (SEQ ID No. 6).

FIG. 9 shows a cationic BoNT/A, "CatH$_N$_v2", nucleotide sequence (SEQ ID No. 7).

FIG. 10 shows a cationic BoNT/A, "CatH$_N$_v2", polypeptide sequence (SEQ ID No. 8).

FIG. 11 shows a cationic BoNT/A, "CatH$_N$_v3", nucleotide sequence (SEQ ID No. 9).

FIG. 12 shows a cationic BoNT/A, "CatH$_N$_v3", polypeptide sequence (SEQ ID No. 10).

FIG. 13 shows a cationic BoNT/E light chain, "CatLC", nucleotide sequence (SEQ ID No. 11).

FIG. 14 shows a cationic BoNT/E light chain, "CatLC", polypeptide sequence (SEQ ID No. 12).

FIG. 15 shows a BoNT/A1 nucleotide sequence (SEQ ID No. 13).

FIG. 16 shows a BoNT/A1 polypeptide sequence (SEQ ID No. 14).

FIG. 17 shows a cationic BoNT/A1, "Cat-A", nucleotide sequence (SEQ ID No. 15).

FIG. 18 shows a cationic BoNT/A1, "Cat-A", polypeptide sequence (SEQ ID No. 16).

FIG. 19 shows a cationic BoNT/A1, "Cat-B", nucleotide sequence (SEQ ID No. 17).

FIG. 20 shows a cationic BoNT/A1, "Cat-B", polypeptide sequence (SEQ ID No. 18).

FIG. 21 shows a cationic BoNT/A1, "Cat-C", nucleotide sequence (SEQ ID No. 19).

FIG. 22 shows a cationic BoNT/A1, "Cat-C", polypeptide sequence (SEQ ID No. 20).

FIG. 23 shows a cationic BoNT/A1, "Cat-D", nucleotide sequence (SEQ ID No. 21).

FIG. 24 shows a cationic BoNT/A1, "Cat-D", polypeptide sequence (SEQ ID No. 22).

DETAILED DESCRIPTION

Figure 1:
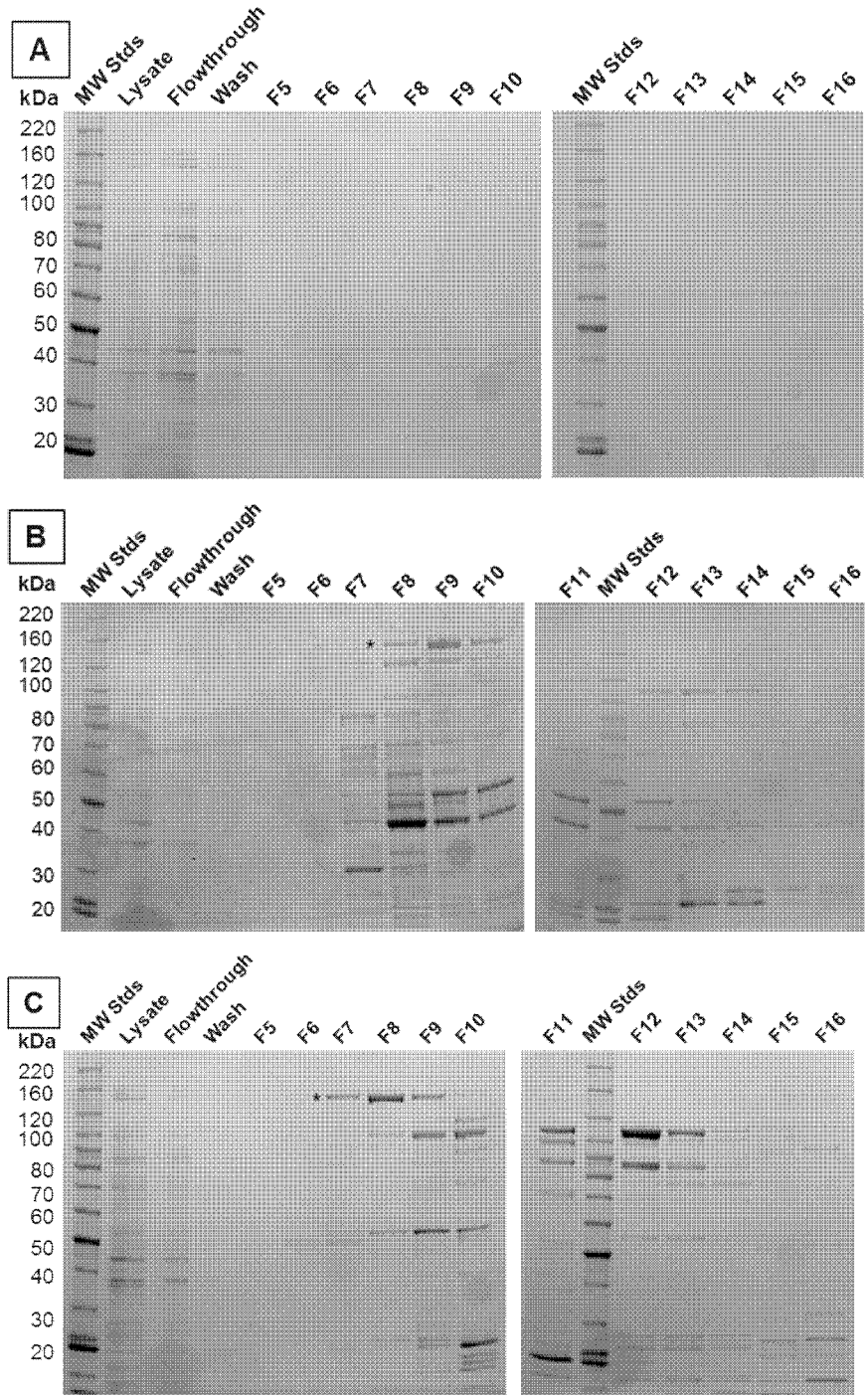
FIG. 1 shows rBoNT/A1 capture on cation exchange resins at different pH. E. coli lysates of endonegative rBoNT/A1 were buffer exchanged to pH 6.0 (panels A and B), pH 7.5 (panels C and D), or pH 8.0 (panels E and F). Lysates were loaded onto Hi-Trap SP-HP, washed, and eluted with either a pH (panel A) or NaCl (panels B-F) gradient. Fractions F5-F16 were analysed by SDS-PAGE, and BoNT/A is indicated with an asterisk (*) on each panel.
Figure 1:
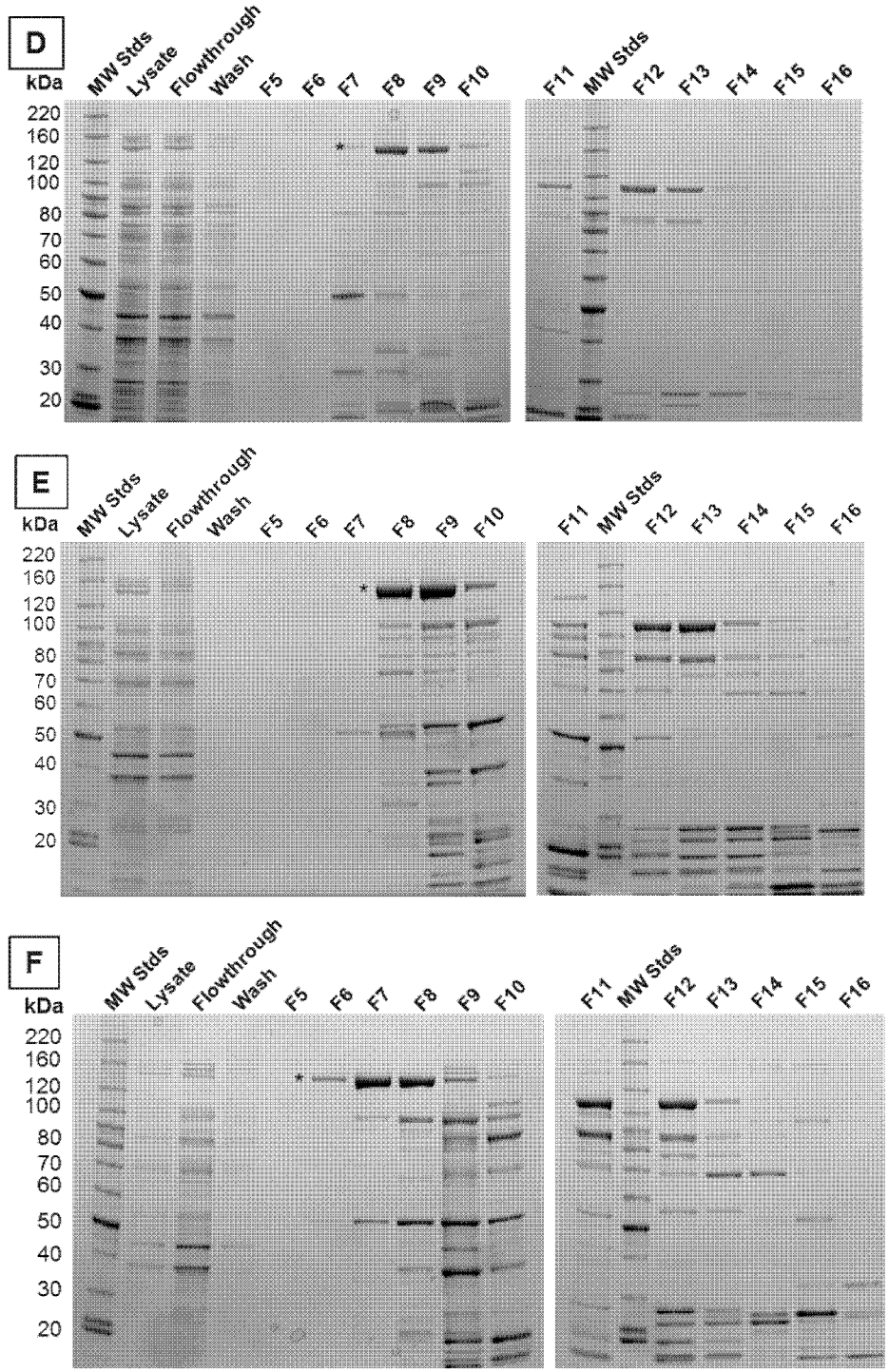

A seminal finding of the present invention is that clostridial neurotoxins associate with cation exchange residues at at least pH 7.3. This is highly unexpected and contrary to the prevailing wisdom in the art, which teaches using pH values during cation exchange chromatography that are well below the pI of the protein being purified.

The inventors have also surprisingly found that use of a buffer having a pH value that is −1 pH unit or higher than the calculated isoelectric point (pI) of said clostridial neurotoxin increases binding and/or yield when compared to a similar use under different pH conditions.

Therefore, in one embodiment there is provided a method for purifying a clostridial neurotoxin comprising contacting a cation exchange resin with a composition comprising a clostridial neurotoxin, wherein the contacting step is performed at at least pH 7.3, wherein said step of contacting a cation exchange resin with a composition comprising said clostridial neurotoxin occurs prior to conversion of said clostridial neurotoxin from a single chain form into a dichain form.

In one embodiment the contacting step may be performed at at least about pH 7.3. Suitably the contacting step may be performed at at least about pH 7.4 or at least pH 7.5.

Suitably, the contacting step may be performed at at least about pH 7.6 or at least about pH 7.7.

Suitably, the contacting step may be performed at at least about pH 7.8 or at least about pH 7.9.

Suitably, the contacting step may be performed at at least about pH 8.0.

In another embodiment the contacting step may be performed at at least about pH 7.3 to about pH 9.5. Suitably, the contacting step may be performed at a pH value of between about pH 7.5 to about pH 9.0, or between about pH 7.5 to about pH 8.5.

Suitably, the contacting step may be performed at a pH value of about pH 7.5.

Suitably, the contacting step may be performed at a pH value of about pH 8.0.

The term "purifying" as used herein means removing one or more non-clostridial neurotoxin contaminants which might be present in a composition comprising a clostridial neurotoxin, preferably with the aim of obtaining a clostridial neurotoxin that is free from said non-clostridial neurotoxin contaminants. In other words, the term "purifying" is intended to refer to a degree of purification rather than to absolute purification, unless otherwise stated. Therefore the term "purifying" may refer to removing at least 5% (suitably at least 10% or 20%) of non-clostridial neurotoxin contaminants. Suitably "purifying" may refer to removing at least 30%, 40%, 50%, 60%, 70%, 80%, 90% or 95% of contaminants.

In another embodiment there is provided the use of a buffer having a pH value that is −1 pH unit or higher than the calculated pI of a clostridial neurotoxin for contacting a composition comprising the clostridial neurotoxin with a cation exchange resin for increased binding and/or yield of the clostridial neurotoxin, when compared to using a pH value that is more than −1 pH units lower than the calculated pI of said clostridial neurotoxin under identical conditions, and wherein said clostridial neurotoxin is in a single chain form.

The term "more than −1 pH units or higher than the calculated pI of a clostridial neurotoxin" as used herein means a pH higher than −1 pH units below the calculated pI of the clostridial neurotoxin. For example, this term would encompass −0.5, +0.5, +1 pH units, etc. As an example, if a clostridial neurotoxin has a pI of 8.0, then a pH value that is more than −1 pH units or higher means a pH of more than pH 7.0, e.g. pH 8.0, pH 9.0, etc.

The term "more than −1 pH units lower than the calculated pI of said clostridial neurotoxin" as used herein means a pH lower than −1 pH units below the calculated pI of the clostridial neurotoxin. For example, this term would encompass −2 pH units, etc. As an example, if a clostridial neurotoxin has a pI of 8.0, then a pH value that is more than −1 pH units lower means a pH of less than pH 7.0, e.g. pH 6.0, pH 5.0, etc.

The cation exchange resin for use in the present invention may be any kind of cation exchange resin capable of associating with a clostridial neurotoxin. In one embodiment the cation exchange resin may be a strong cation exchange resin, a weak cation exchange resin or combinations thereof.

Suitably the cation exchange resin may be a strong cation exchange resin.

Non-limiting examples of strong cation exchangers include: SP SEPHAROSE® HP, SP SEPHAROSE® FF (both available from GE Healthcare, UK), MUSTANG® S, S CERAMIC, HYPERD® F, ACRODISC® with MUSTANG® S, ACROPREP® with MUSTANG® S and/or ACROSEP® with S 35 CERAMIC HYPERD® F (all of which (unless otherwise indicated) are commercially available from Pall Corporation, 25 Harbor Park Drive, Port Washington, N.Y. 11050, USA).

In a preferred embodiment the cation exchange resin may be a strong cation exchange resin comprising sulfonic acid.

In one embodiment the cation exchange resin may be a SP SEPHAROSE® HP resin and/or SP SEPHAROSE® FF resin (all commercially available from GE Healthcare, UK).

Non-limiting examples of weak cation exchangers include: CM CERAMIC HYPERD® F, ACROSEP® with CM CERAMIC and/or HYPERD® F (all of which are commercially available 10 from Pall Corporation, 25 Harbor Park Drive, Port Washington, N.Y. 11050, USA).

In one embodiment the weak cation exchange resin may be a resin comprising carboxymethyl.

In one embodiment a mixed mode resin may be used. Mixed mode resins may use charged ligands that interact with a target protein via ionic interactions and may be enhanced with one or more functional group(s) (e.g., resulting in interaction by hydrogen bonding, hydrophobic, and van der Waals interactions). Therefore in one embodiment a mixed mode resin may function as an ion exchange resin and a hydrophobic interaction resin. Suitably a mixed mode resin may function as a cation exchange resin (suitably weak cation exchange resin) and a hydrophobic interaction resin.

Non-limiting examples of mixed mode resins include the CAPTO® multimodal range of chromatography columns (commercially available from GE Healthcare, UK).

In nature, clostridial neurotoxins are synthesised as a single-chain polypeptide that is modified post-translationally by a proteolytic cleavage event to form two polypeptide chains joined together by a disulphide bond. Cleavage occurs at a specific cleavage site, often referred to as the activation site that is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises an N-terminal translocation component ($H_N$ domain) and a C-terminal targeting component ($H_C$ domain). The cleavage site is located between the L-chain and the translocation domain components. Following binding of the $H_C$ domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Many different types of clostridial neurotoxins are suitable for use in the present invention. Thus, in the context of the present invention, the term "clostridial neurotoxin" embraces toxins produced by *C. botulinum* (botulinum neurotoxin serotypes A, B, $C_1$, D, E, F and G), *C. tetani* (tetanus neurotoxin), *C. butyricum* (botulinum neurotoxin serotype E), and *C. baratii* (botulinum neurotoxin serotype F), as well as modified clostridial neurotoxins or derivatives derived from any of the foregoing. The term "clostridial neurotoxin" may also embrace naturally occurring botulinum neurotoxin hybrids, mosaics and chimeras.

The term "mosaic" as used in this context refers to a naturally occurring clostridial neurotoxin that comprises at least one functional domain from another type of clostridial neurotoxins (e.g. a clostridial neurotoxin of a different serotype), said clostridial neurotoxin not usually comprising said at least one functional domain.

Therefore in one embodiment a clostridial neurotoxin of, or for use in the present invention may be obtainable from one or more *Clostridia* selected from the group consisting of: *Clostridium botulinum Clostridium tetani, Clostridium baratti* and *C. butyricum*.

Botulinum neurotoxin (BoNT) is produced by *C. botulinum* in the form of a large protein complex, consisting of BoNT itself complexed to a number of accessory proteins. There are at present eight different classes of botulinum neurotoxin, namely: botulinum neurotoxin serotypes A, B, $C_1$, D, E, F, G, and H, all of which share similar structures and modes of action. Different BoNT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

BoNTs are absorbed in the gastrointestinal tract, and, after entering the general circulation, bind to the presynaptic membrane of cholinergic nerve terminals and prevent the release of their neurotransmitter acetylcholine. BoNT/B, BoNT/D, BoNT/F and BoNT/G cleave synaptobrevin/vesicle-associated membrane protein (VAMP); BoNT/$C_1$, BoNT/A and BoNT/E cleave the synaptosomal-associated protein of 25 kDa (SNAP-25); and BoNT/$C_1$ cleaves syntaxin.

Tetanus toxin is produced in a single serotype by *C. tetani*. *C. butyricum* produces BoNT/E, while *C. baratii* produces BoNT/F.

In one embodiment the clostridial neurotoxin may be a TeNT. A reference TeNT sequence has the UniProtKB Accession Number P04958.

Suitably the clostridial neurotoxin of, or for use in, the present invention may be a botulinum neurotoxin (BoNT), preferably one or more BoNT(s) selected from the group consisting of: BoNT/A, BoNT/B, BoNT/$C_1$, BoNT/D, BoNT/E, BoNT/F and BoNT/G.

In one embodiment the clostridial neurotoxin may be BoNT/A. A reference BoNT/A sequence has the UniProtKB Accession Number P10845.

In another embodiment the clostridial neurotoxin may be BoNT/B. A reference BoNT/B sequence has the UniProtKB Accession Number P10844.

In another embodiment the clostridial neurotoxin may be BoNT/C. A reference BoNT/$C_1$ sequence has the UniProtKB Accession Number P18640.

In another embodiment the clostridial neurotoxin may be BoNT/D. A reference BoNT/D sequence has the UniProtKB Accession Number P19321.

In another embodiment the clostridial neurotoxin may be BoNT/E. A reference BoNT/E sequence has the UniProtKB Accession Number Q00496.

In another embodiment the clostridial neurotoxin may be BoNT/F. A reference BoNT/F sequence has the UniProtKB Accession Number YP_001390123.

In another embodiment the clostridial neurotoxin may be BoNT/G. A reference BoNT/G sequence has the UniProtKB Accession Number Q60393.

The term "clostridial neurotoxin" is also intended to embrace modified clostridial neurotoxins and derivatives thereof, including but not limited to those described below. A modified clostridial neurotoxin or derivative may contain one or more amino acids that has been modified as compared to the native (unmodified) form of the clostridial neurotoxin, or may contain one or more inserted amino acids that are not present in the native (unmodified) form of the clostridial neurotoxin, or may have one or more amino acids deleted when compared to the native (unmodified) form of the clostridial neurotoxin. By way of example, a modified clostridial neurotoxin may have modified amino acid sequences in one or more domains relative to the native (unmodified) clostridial neurotoxin sequence. Such modifications may modify functional aspects of the neurotoxin, for example biological activity or persistence.

A modified clostridial neurotoxin may be a modified clostridial neurotoxin taught in WO2015/004461 A1 (e.g. a cationic BoNT).

In another embodiment a clostridial neurotoxin of, or for use in, the present invention may be a cationic BoNT/A.

In another embodiment a clostridial neurotoxin of, or for use in, the present invention may be a cationic BoNT/B.

In another embodiment a clostridial neurotoxin of, or for use in, the present invention may be a cationic BoNT/C.

In another embodiment a clostridial neurotoxin of, or for use in, the present invention may be a cationic BoNT/D.

In another embodiment a clostridial neurotoxin of, or for use in, the present invention may be a cationic BoNT/E.

In another embodiment a clostridial neurotoxin of, or for use in, the present invention may be a cationic BoNT/F.

In another embodiment a clostridial neurotoxin of, or for use in, the present invention may be a cationic BoNT/G.

A cationic BoNT is a BoNT that has a higher isoelectric point than its native BoNT counterpart.

Modified clostridial neurotoxins may have one or more modifications in the amino acid sequence of the heavy chain (such as a modified $H_C$ domain), wherein said modified heavy chain binds to target nerve cells with a higher or lower affinity than the native (unmodified) clostridial neurotoxin. Such modifications in the $H_C$ domain can include modifying residues in the ganglioside binding site of the $H_C$ domain or in the protein (SV2 or synaptotagmin) binding site that alter binding to the ganglioside receptor and/or the protein receptor of the target nerve cell. Examples of such modified clostridial neurotoxins are described in WO 2006/027207 and WO 2006/114308, both of which are hereby incorporated by reference in their entirety.

A modified clostridial neurotoxin may have one or more modifications in the amino acid sequence of the light chain, for example modifications in the substrate binding or catalytic domain which may alter or modify the SNARE protein specificity of the modified LC. Examples of such modified clostridial neurotoxins are described in WO 2010/120766 and US 2011/0318385, both of which are hereby incorporated by reference in their entirety.

A modified clostridial neurotoxin may comprise one or more modifications that increases or decreases the biological activity and/or the biological persistence of the modified clostridial neurotoxin. For example, a modified clostridial neurotoxin may comprise a leucine- or tyrosine-based motif, wherein said motif increases or decreases the biological activity and/or the biological persistence of the modified clostridial neurotoxin. Suitable leucine-based motifs include xDxxxLL, xExxxLL, xExxxlL, and xExxxLM (wherein x is any amino acid). Suitable tyrosine-based motifs include Y-x-x-Hy (wherein Hy is a hydrophobic amino acid). Examples of modified clostridial neurotoxins comprising leucine- and tyrosine-based motifs are described in WO 2002/08268, which is hereby incorporated by reference in its entirety.

The term "clostridial neurotoxin" is intended to embrace hybrid and chimeric clostridial neurotoxins. A hybrid or chimeric clostridial neurotoxin comprises at least a portion of a light chain from one clostridial neurotoxin or subtype thereof, and at least a portion of a heavy chain from another clostridial neurotoxin or clostridial neurotoxin subtype.

In one embodiment the hybrid or chimeric clostridial neurotoxin may contain the entire light chain from one clostridial neurotoxin subtype and the heavy chain from another clostridial neurotoxin subtype. In another embodiment, a chimeric clostridial neurotoxin may contain a portion (e.g. the binding domain) of the heavy chain of one clostridial neurotoxin subtype, with another portion of the heavy chain being from another clostridial neurotoxin subtype. Similarly or alternatively, the therapeutic element may comprise light chain portions from different clostridial neurotoxins. Such hybrid or chimeric clostridial neurotoxins are useful, for example, as a means of delivering the therapeutic benefits of such clostridial neurotoxins to patients who are immunologically resistant to a given clostridial neurotoxin subtype, to patients who may have a lower than average concentration of receptors to a given clostridial neurotoxin heavy chain binding domain, or to patients who may have a protease-resistant variant of the membrane or vesicle toxin substrate (e.g., SNAP-25, VAMP and syntaxin). Hybrid and chimeric clostridial neurotoxins are described in U.S. Pat. No. 8,071,110 and in GB1607901.4 (which is not yet published), which publications are hereby incorporated by reference in their entirety. Thus, in one embodiment, the clostridial neurotoxin for purification according to a method or use of the present invention may be an engineered clostridial neurotoxin, suitably it may be an engineered hybrid clostridial neurotoxin, or an engineered chimeric clostridial neurotoxin.

The term "clostridial neurotoxin" is intended to embrace re-targeted clostridial neurotoxins. In a re-targeted clostridial neurotoxin, the clostridial neurotoxin is modified to include an exogenous ligand known as a Targeting Moiety (TM). The TM is selected to provide binding specificity for a desired target cell, and as part of the re-targeting process the native binding portion of the clostridial neurotoxin (e.g. the $H_C$ domain, or the $H_{CC}$ domain) may be removed. Re-targeting technology is described, for example, in: EP-B-0689459; WO 1994/021300; EP-B-0939818; U.S. Pat. Nos. 6,461,617; 7,192,596; WO 1998/007864; EP-B-0826051; U.S. Pat. Nos. 5,989,545; 6,395,513; 6,962,703; WO 1996/033273; EP-B-0996468; U.S. Pat. No. 7,052,702; WO 1999/017806; EP-B-1107794; U.S. Pat. No. 6,632,440; WO 2000/010598; WO 2001/21213; WO 2006/059093; WO 2000/62814; WO 2000/04926; WO 1993/15766; WO 2000/61192; and WO 1999/58571; all of which are hereby incorporated by reference in their entirety. Thus, in one embodiment, the engineered clostridial neurotoxin for use in the present invention may be an engineered re-targeted clostridial neurotoxin.

The present invention also embraces clostridial neurotoxins (or uses thereof) that have a non-native protease cleavage site. In such clostridial neurotoxins, the native protease cleavage site (also known as the activation site, as described above) is modified or replaced with a protease cleavage site that is not native to that clostridial neurotoxin (i.e. an exogenous cleavage site). Such a site will require an exogenous protease for cleavage, which allows for improved control over the timing and location of cleavage events. Non-native protease cleavage sites that may be employed in clostridial neurotoxins include:

Enterokinase (DDDDK↓; SEQ ID NO: 23)
Factor Xa (IEGR↓; SEQ ID NO: 24/IDGR↓; SEQ ID NO: 25)
TEV (Tobacco Etch virus) (ENLYFQ↓G: SEQ ID NO: 26)
Thrombin (LVPR↓GS: SEQ ID NO: 27)
PreScission (LEVLFQ↓GP; SEQ ID NO: 28).

```
Enterokinase          (DDDDK↓; SEQ ID NO: 23)

Factor Xa             (IEGR↓; SEQ ID NO: 24 / IDGR↓; SEQ ID NO: 25)

TEV(Tobacco Etch virus) (ENLYFQ↓G; SEQ ID NO: 26)

Thrombin              (LVPR↓GS; SEQ ID NO: 27)

PreScission           (LEVLFQ↓GP; SEQ ID NO: 28).
```

Additional protease cleavage sites include recognition sequences that are cleaved by a non-cytotoxic protease, for example by the light chain of a clostridial neurotoxin. These include the SNARE (e.g. SNAP-25, syntaxin, VAMP) protein recognition sequences that are cleaved by non-cytotoxic proteases such as the light chain of a clostridial neurotoxin. Clostridial neurotoxins comprising non-native protease cleavage sites are described in U.S. Pat. No. 7,132,259, EP 1206554-B2 and US 2007/0166332, all of which are hereby incorporated by reference in their entirety. Also embraced by the term protease cleavage site is an intein, which is a self-cleaving sequence. The self-splicing reaction is controllable, for example by varying the concentration of reducing agent present.

The present invention also embraces the use of clostridial neurotoxins comprising a "destructive cleavage site". In said clostridial neurotoxins, a non-native protease cleavage site is incorporated into the clostridial neurotoxin, at a location chosen such that cleavage at said site will decrease the activity of, or inactivate, the clostridial neurotoxin. The destructive protease cleavage site can be susceptible to cleavage by a local protease, in the event that the clostridial neurotoxin, following administration, migrates to a non-target location. Suitable non-native protease cleavage sites include those described above. Clostridial neurotoxins comprising a destructive cleavage site are described in WO 2010/094905 and WO 2002/044199, both of which are hereby incorporated by reference in their entirety.

The clostridial neurotoxins of or for use in the present invention may be PEGylated—this may help to increase stability, for example duration of action of the light chain component. PEGylation is particularly preferred when the light chain comprises a BoNT/A, B or $C_1$ protease. PEGylation preferably includes the addition of PEG to the N-terminus of the light chain component. By way of example, the N-terminus of a light chain may be extended with one or more amino acid (e.g. cysteine) residues, which may be the same or different. One or more of said amino acid residues may have its own PEG molecule attached (e.g. covalently attached) thereto. An example of this technology is described in WO2007/104567, which is hereby incorporated by reference in its entirety.

In a preferred embodiment the clostridial neurotoxin of the present invention or for use in the present invention may be free from the complexing proteins that are present in a naturally occurring clostridial neurotoxin complex.

The clostridial neurotoxin of, or for use in, the present invention may be obtainable by expressing a nucleic acid comprising SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21 or a nucleic acid having at least 65% or 70% sequence identity thereto.

Suitably, the clostridial neurotoxin of, or for use in, the present invention may be obtainable by expressing a nucleic acid comprising SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21 or a nucleic acid having at least 75% or 80% sequence identity thereto.

Suitably, the clostridial neurotoxin of, or for use in, the present invention may be obtainable by expressing a nucleic acid comprising SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21 or a nucleic acid having at least 85% or 90% sequence identity thereto.

Suitably, the clostridial neurotoxin of, or for use in, the present invention may be obtainable by expressing a nucleic acid comprising SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21 or a nucleic acid having at least 95% or 99% sequence identity thereto.

In one embodiment a clostridial neurotoxin of, or for use in, the present invention may comprise a polypeptide sequence shown as SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22 or a polypeptide sequence having at least 65% or 70% sequence identity thereto.

Suitably, a clostridial neurotoxin of, or for use in, the present invention may comprise a polypeptide sequence shown as SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22 or a polypeptide sequence having at least 75% or 80% sequence identity thereto.

Suitably, a clostridial neurotoxin of, or for use in, the present invention may comprise a polypeptide sequence shown as SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22 or a polypeptide sequence having at least 85% or 90% sequence identity thereto.

Suitably, a clostridial neurotoxin of, or for use in, the present invention may comprise a polypeptide sequence shown as SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22 or a polypeptide sequence having at least 95% or 99% sequence identity thereto.

In one embodiment a clostridial neurotoxin of, or for use in, the present invention may be obtainable by expressing a nucleic acid comprising SEQ ID No. 3, SEQ ID No. 13 or a nucleic acid having at least 65% or 70% sequence identity thereto.

Suitably, a clostridial neurotoxin of, or for use in, the present invention may be obtainable by expressing a nucleic acid comprising SEQ ID No. 3, SEQ ID No. 13 or a nucleic acid having at least 75% or 80% sequence identity thereto.

Suitably, a clostridial neurotoxin of, or for use in, the present invention may be obtainable by expressing a nucleic acid comprising SEQ ID No. 3, SEQ ID No. 13 or a nucleic acid having at least 85% or 90% sequence identity thereto.

Suitably, a clostridial neurotoxin of, or for use in, the present invention may be obtainable by expressing a nucleic acid comprising SEQ ID No. 3, SEQ ID No. 13 or a nucleic acid having at least 95% or 99% sequence identity thereto.

In one embodiment a clostridial neurotoxin of, or for use in, the present invention may comprise a polypeptide sequence shown as SEQ ID No. 4, SEQ ID No. 14 or a polypeptide sequence having at least 65% or 70% sequence identity thereto.

Suitably, a clostridial neurotoxin of, or for use in, the present invention may comprise a polypeptide sequence shown as SEQ ID No. 4, SEQ ID No. 14 or a polypeptide sequence having at least 75% or 80% sequence identity thereto.

Suitably, a clostridial neurotoxin of, or for use in, the present invention may comprise a polypeptide sequence shown as SEQ ID No. 4, SEQ ID No. 14 or a polypeptide sequence having at least 85% or 90% sequence identity thereto.

Suitably, a clostridial neurotoxin of, or for use in, the present invention may comprise a polypeptide sequence shown as SEQ ID No. 4, SEQ ID No. 14 or a polypeptide sequence having at least 95% or 99% sequence identity thereto.

In another embodiment a clostridial neurotoxin of, or for use in, the present invention may be a cationic clostridial neurotoxin obtainable by expressing a nucleic acid comprising SEQ ID No. 1, SEQ ID No. 5, SEQ ID No. 7, SEQ ID No. 9, SEQ ID No. 11, SEQ ID No. 15, SEQ ID No. 17, SEQ ID No. 19, SEQ ID No. 21, or a nucleic acid having at least 65% or 70% sequence identity thereto.

Suitably, a clostridial neurotoxin of, or for use in, the present invention may be a cationic clostridial neurotoxin obtainable by expressing a nucleic acid comprising SEQ ID No. 1, SEQ ID No. 5, SEQ ID No. 7, SEQ ID No. 9, SEQ ID No. 11, SEQ ID No. 15, SEQ ID No. 17, SEQ ID No. 19, SEQ ID No. 21, or a nucleic acid having at least 75% or 80% sequence identity thereto.

Suitably, a clostridial neurotoxin of, or for use in, the present invention may be a cationic clostridial neurotoxin obtainable by expressing a nucleic acid comprising SEQ ID No. 1, SEQ ID No. 5, SEQ ID No. 7, SEQ ID No. 9, SEQ ID No. 11, SEQ ID No. 15, SEQ ID No. 17, SEQ ID No. 19, SEQ ID No. 21, or a nucleic acid having at least 85% or 90% sequence identity thereto.

Suitably, a clostridial neurotoxin of, or for use in, the present invention may be a cationic clostridial neurotoxin obtainable by expressing a nucleic acid comprising SEQ ID No. 1, SEQ ID No. 5, SEQ ID No. 7, SEQ ID No. 9, SEQ ID No. 11, SEQ ID No. 15, SEQ ID No. 17, SEQ ID No. 19, SEQ ID No. 21, or a nucleic acid having at least 95% or 99% sequence identity thereto.

In another embodiment a clostridial neurotoxin of, or for use in, the present invention may be a cationic clostridial neurotoxin comprising a polypeptide sequence shown as SEQ ID No. 2, SEQ ID No. 6, SEQ ID No. 8, SEQ ID No. 10, SEQ ID No. 12, SEQ ID No. 16, SEQ ID No. 18, SEQ ID No. 20, SEQ ID No. 22, or a nucleic acid having at least 65% or 70% sequence identity thereto.

Suitably, a clostridial neurotoxin of, or for use in, the present invention may be a cationic clostridial neurotoxin comprising a polypeptide sequence shown as SEQ ID No. 2, SEQ ID No. 6, SEQ ID No. 8, SEQ ID No. 10, SEQ ID No. 12, SEQ ID No. 16, SEQ ID No. 18, SEQ ID No. 20, SEQ ID No. 22, or a nucleic acid having at least 75% or 80% sequence identity thereto.

Suitably, a clostridial neurotoxin of, or for use in, the present invention may be a cationic clostridial neurotoxin comprising a polypeptide sequence shown as SEQ ID No. 2, SEQ ID No. 6, SEQ ID No. 8, SEQ ID No. 10, SEQ ID No. 12, SEQ ID No. 16, SEQ ID No. 18, SEQ ID No. 20, SEQ ID No. 22, or a nucleic acid having at least 85% or 90% sequence identity thereto.

Suitably, a clostridial neurotoxin of, or for use in, the present invention may be a cationic clostridial neurotoxin comprising a polypeptide sequence shown as SEQ ID No. 2, SEQ ID No. 6, SEQ ID No. 8, SEQ ID No. 10, SEQ ID No. 12, SEQ ID No. 16, SEQ ID No. 18, SEQ ID No. 20, SEQ ID No. 22, or a nucleic acid having at least 95% or 99% sequence identity thereto.

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

The term "composition comprising a clostridial neurotoxin" refers to any such composition in any state of preparation.

In one embodiment a composition comprising a clostridial neurotoxin may have a pH value that is at least about pH 7.3. Suitably, a composition comprising a clostridial neurotoxin may have a pH value that is at least about pH 7.4 or pH 7.5.

Suitably, a composition comprising a clostridial neurotoxin may have a pH value that is at least about pH 7.6 or at least about pH 7.7.

Suitably, a composition comprising a clostridial neurotoxin may have a pH value that is at least about pH 7.8 or at least about pH 7.9.

Suitably, a composition comprising a clostridial neurotoxin may have a pH value that is at least about pH 8.0.

In another embodiment a composition comprising a clostridial neurotoxin may have a pH between about pH 7.3 to about pH 9.5. Suitably, a composition comprising a clostridial neurotoxin may have a pH between about pH 7.5 to about pH 9.0, or between about pH 7.5 to about pH 8.5.

Suitably, a composition comprising a clostridial neurotoxin may have a pH value of about pH 7.5.

Suitably, a composition comprising a clostridial neurotoxin may have a pH value of about pH 8.0.

In some embodiments the composition comprising a clostridial neurotoxin may have a pH value that is −1 pH unit or higher than the calculated isoelectric point of the clostridial neurotoxin comprised therein.

Suitably, the composition comprising a clostridial neurotoxin may have a pH value that is −0.5 pH unit or higher than the calculated isoelectric point of the clostridial neurotoxin comprised therein.

Suitably, the composition comprising a clostridial neurotoxin may have a pH value that is at least the calculated isoelectric point of the clostridial neurotoxin comprised therein.

Suitably, the composition comprising a clostridial neurotoxin may have a pH value that is at least about 0.2 pI units or at least about 0.5 pH units above the calculated isoelectric point of the clostridial neurotoxin comprised therein.

In one embodiment the composition comprising a clostridial neurotoxin may have a pH value that is between about −1 pH units below the calculated isoelectric point of the clostridial neurotoxin comprised therein to about 2 pH units above the calculated isoelectric point.

Suitably, the composition comprising a clostridial neurotoxin may have a pH value that is between about −0.5 pH units below the calculated isoelectric point of the clostridial neurotoxin comprised therein to about 1.5 pH units above the calculated isoelectric point.

Suitably, the composition comprising a clostridial neurotoxin may have a pH value that is between about the calculated isoelectric point of the clostridial neurotoxin comprised therein to about 2 pH units above the calculated isoelectric point.

Suitably, the composition comprising a clostridial neurotoxin may have a pH value that is between about 0.2 pH units above the calculated isoelectric point of the clostridial neurotoxin comprised therein to about 1.5 pH units above the calculated isoelectric point.

Preferably, the composition comprising a clostridial neurotoxin may have a pH value that is between about 0.5 pH units above the calculated isoelectric point of the clostridial neurotoxin comprised therein to about 1.5 pH units above the calculated isoelectric point.

In some embodiments the "composition comprising a clostridial neurotoxin" may be a cell-free extract and/or a cell lysate. The term "cell-free extract" means that the extract comprises less than about 5% of cells, more preferably less than about 1% or 0.1% of cells per total volume of extract.

A cell-free extract and/or a cell lysate may be obtainable from a host cell expressing a nucleotide sequence encoding a clostridial neurotoxin, for example one or more of the nucleotide sequences herein. In one embodiment a host cell may be an *Escherichia coli* host cell.

The cell lysate may be obtained following lysis of a cell paste. A cell paste may be lysed using any method known in the art. For example cell lysis may be achieved using sonication, suitably in the presence of at least one nuclease (e.g. BENZONASE® commercially available from Sigma-Aldrich).

Following preparation of a cell lysate, said cell lysate may be buffer exchanged. This may be carried out using any suitable methodology known to one skilled in the art. For example, this may be carried out using a desalting column or dialysis with an appropriate dialysis membrane and buffer. An example of a suitable desalting column may include an ECONO-PAC® 10DG desalting column (available commercially from Bio-Rad).

In other embodiments the "composition comprising a clostridial neurotoxin" may be a composition obtainable (e.g. obtained) from one or more prior purification step(s) (i.e. a purification step carried out prior to obtaining the composition). The prior purification step may be any purification step known in the art, preferably a purification step known to be suitable for purifying a clostridial neurotoxin. The prior purification step may be one or more selected from the group consisting of: a chromatographic purification step, a precipitation-based purification step (e.g. an ammonium sulphate precipitation) and a crystallisation purification step.

In some embodiment the method and/or use according to the invention may comprise a first purification step (e.g. a first chromatographic step) of contacting a cation exchange resin with a composition comprising a clostridial neurotoxin.

In other embodiments the method and/or use may comprise one or more purification steps. The one or more purification steps may be carried out before or after contacting a cation exchange residue with a composition comprising a clostridial neurotoxin. Suitably, the one or more purification steps may be carried out after contacting a cation exchange residue with a composition comprising a clostridial neurotoxin.

The one or more purification step(s) may be selected from the group consisting of: a chromatographic purification step and a precipitation-based purification step (e.g. an ammonium sulphate precipitation).

The term "chromatographic purification step" as used herein may refer to one or more selected from the group consisting of: hydrophobic interaction chromatography, ion exchange chromatography (e.g. cation exchange or anion exchange chromatography), mixed mode chromatography, hydrophobic charge-induction chromatography, gel filtration chromatography and affinity chromatography.

In one embodiment a chromatographic purification step may comprise the use of mixed mode chromatography, suitably the use of a hydroxyapatite resin. Suitably a hydroxyapatite resin may be a hydroxyapatite I and/or a hydroxyapatite II resin. Such resins are commercially available (e.g. from GE Healthcare, UK).

In another embodiment a chromatographic purification step may be cation exchange chromatography. Cation exchange chromatography may involve the use of a strong cation exchange resin and/or a weak cation exchange resin.

Suitably, a strong cation exchange resin may be a resin comprising sulfonic acid.

Suitably a weak cation exchange resin may be a resin comprising carboxymethyl.

In another embodiment a chromatographic purification step may be anion exchange chromatography. Anion exchange chromatography may involve the use of a strong anion exchange resin and/or a weak anion exchange resin.

Examples of a strong anion exchange resins include those comprising a quaternary ammonium, such as MUSTANG® Q, Q CERAMIC HYPERD® F, ACRODISC® with MUSTANG® Q, ACROPREP® with MUSTANG® Q, ACROSEP® with Q CERAMIC HYPERD® F, Q and S HYPERCEL® and/or HYPERCEL® STAR AX (all of which are commercially available from Pall Corporation, 25 Harbor Park Drive, Port Washington, N.Y. 11050, USA).

Examples of a weak anion exchange resins include those comprising carboxymethyl, such as CM CERAMIC HYPERD® F, ACROSEP® with CM CERAMIC and/or HYPERD® F (all of which are commercially available from Pall Corporation, 25 Harbor Park Drive, Port Washington, N.Y. 11050, USA).

In embodiments where the chromatographic purification step is a gel filtration step, suitably the resin may be a SUPERDEX® 200 resin (commercially available from GE Healthcare UK). In embodiments where the chromatographic purification step is a hydrophobic interaction step, suitably the resin may be a Phenyl FF resin, an Octyl FF resin and/or a Butyl FF resin (commercially available from GE Healthcare UK).

In embodiments where the chromatographic purification step is an affinity chromatography step, suitably the resin may be selected from: glutathione resin, streptavidin resin, biotin resin, chelated metal resin, dextrin SEPHAROSE® resin and IgG resin (commercially available from GE Healthcare UK).

In some embodiments the chromatographic purification step may be an antibody affinity chromatography step.

In some embodiments the method or use may comprise a step of converting the botulinum neurotoxin from a single chain form into a dichain form (activation step). Activating a clostridial neurotoxin is suitably carried out after contacting the clostridial neurotoxin with a cation exchange resin. More preferably, the activating step may be carried out after a clostridial neurotoxin has been separated from a cation exchange resin.

A clostridial neurotoxin may be activated by contacting (and optionally incubating) the clostridial neurotoxin with a suitable protease at conditions under which the suitable protease may cleave a polypeptide sequence of a clostridial neurotoxin.

In one embodiment a suitable protease may be an endoprotease capable of cleaving a clostridial neurotoxin polypeptide sequence such that it becomes activated.

In one embodiment an endoprotease for use in accordance with the invention may be a Lys-C protease. A suitable Lys-C protease may be one taught in and/or WO2014/079495 or WO2014/080206 both of which are incorporated herein by reference.

Lys-C protease may be obtainable from any suitable source and is commercially available from Life Technologies Ltd, UK.

In a more preferred embodiment the method and/or use of the invention may alternatively and/or additionally comprise hydrophobic interaction chromatography.

Therefore in a preferred embodiment there is provided a method and/or use of the invention further comprising (or further consisting of) activation of a clostridial neurotoxin using Lys-C and hydrophobic interaction chromatography.

Preferably, the hydrophobic interaction chromatography may comprise the use of one or more selected from the group consisting of: a butyl SEPHAROSE® resin, a phenyl SEPHAROSE® resin and an octyl SEPHAROSE® resin.

The present invention comprises contacting a cation exchange resin with a composition comprising a clostridial neurotoxin.

The term "contacting" when referring to the step of contacting of a cation exchange resin with a composition comprising a clostridial neurotoxin is intended to encompass any known method for facilitating the association of a cation exchange resin with a clostridial neurotoxin. For example the contacting step may be carried out by incubating a cation exchange resin with a composition comprising a clostridial neurotoxin under suitable conditions for a suitable time. Suitable incubation conditions may include the presence of agitation or appropriate temperatures selected for enhancing protein stability and/or maintenance of activity.

In one embodiment the contacting step may be carried out by applying a composition comprising a clostridial neurotoxin to a column comprising a cation exchange resin. Suitably, contact may be carried out by using an automated or semi-automated process, for example by using a system designed for automated liquid chromatography (e.g. fast protein liquid chromatography).

In another embodiment a composition comprising a clostridial neurotoxin may be admixed with a cation exchange resin. Suitably said admixture may be incubated at an appropriate temperature and/or time to facilitate binding. In some embodiments the admixture may be agitated. In other embodiments a purification column may be prepared from the admixture and subjected to conventional liquid chromatography techniques (e.g. comprising washing and/or elution).

In one embodiment the "association" may suitably be a charge-based interaction or association. Suitably the "association" may be an interaction capable of withstanding exposing the cation exchange resin associated with a clostridial neurotoxin to one or more wash buffers. The term "wash buffer" refers to one or more buffers prepared by the person skilled in the art for use in disrupting binding of unwanted contaminant proteins (suitably proteins that are not clostridial neurotoxins) to the cation exchange resin. Typically, a wash buffer may be prepared such that it is sufficiently stringent to disrupt binding of unwanted contaminant proteins (suitably proteins that are not clostridial neurotoxins) to the cation exchange resin without significantly disrupting binding of the clostridial neurotoxin to the cation exchange resin.

A buffer having a pH of at least about pH 7.3 may be used in the present invention. Suitably a buffer having a pH of at least about pH 7.5 may be used in the present invention.

Solutions of the correct pH are known to the person skilled in the art and may be prepared with any suitable buffer. In one embodiment the buffer may comprise: Bis-Tris (propane), Bis-Tris (methane), Tris, HEPES or citrate phosphate. Suitably the buffer may comprise Bis-Tris (propane). The skilled person may select any suitable molarity of buffer. Suitably the molarity may be at about 50 mM.

In one embodiment a buffer for use in the present invention may have a pH value that is at least about pH 7.3 (suitably at least about pH 7.4 or pH 7.5).

Suitably, a buffer for use in the present invention may have a pH value that is at least about pH 7.6 or at least about pH 7.7.

Suitably, a buffer for use in the present invention may have a pH value that is at least about pH 7.8 or at least about pH 7.9.

Suitably, a buffer for use in the present invention may have a pH value that is at least about pH 8.0.

In another embodiment a buffer for use in the present invention may have a pH between about pH 7.3 to about pH 9.5. Suitably, a buffer for use in the present invention may have a pH between about pH 7.5 to about pH 9.0, or between about pH 7.5 to about pH 8.5.

Suitably, a buffer for use in the present invention may have a pH value of about pH 7.5.

Suitably, a buffer for use in the present invention may have a pH value of about pH 8.0.

The use of the invention comprises the use of a buffer having a pH value that is −1 pH unit or higher than the calculated isoelectric point of the clostridial neurotoxin (e.g. the clostridial neurotoxin that is the subject of said use).

The pH value referred to may be the pH value measured when a cation exchange resin is contacted with a composition comprising a clostridial neurotoxin, for example the pH value of the solution comprising an admixture of a cation exchanger and a composition comprising a clostridial neurotoxin.

The present invention may involve the use of a buffer having a pH value of −1 pH unit or higher that the calculated pI of a clostridial neurotoxin.

Solutions of the correct pH are known to the person skilled in the art and may be prepared with any suitable buffer. In one embodiment the buffer may comprise: Bis-Tris (propane), Bis-Tris (methane), Tris, HEPES or citrate phosphate. Suitably the buffer may comprise Bis-Tris (propane). The skilled person may select any suitable molarity of buffer. Suitably the molarity may be at about 50 mM.

Suitably, the pH value for use in the present invention may be a pH value that is −0.5 pH unit or higher than the calculated isoelectric point of the clostridial neurotoxin.

In one embodiment, the pH value for use in the present invention may be at least the calculated isoelectric point of the clostridial neurotoxin.

Suitably, the pH value may be at least about 0.2 pI units or at least about 0.5 pH units above the calculated isoelectric point of the clostridial neurotoxin.

In one embodiment the pH value may be between about −1 pH units below the calculated isoelectric point of the clostridial neurotoxin to about 2 pH units above the calculated isoelectric point.

Suitably, the pH value may be between about −0.5 pH units below the calculated isoelectric point of the clostridial neurotoxin to about 1.5 pH units above the calculated isoelectric point.

Suitably, the pH value may be between about the calculated isoelectric point of the clostridial neurotoxin to about 2 pH units above the calculated isoelectric point.

Suitably, the pH value may be between about 0.2 pH units above the calculated isoelectric point of the clostridial neurotoxin to about 1.5 pH units above the calculated isoelectric point.

Preferably, the pH value may be between about 0.5 pH units above the calculated isoelectric point of the clostridial neurotoxin to about 1.5 pH units above the calculated isoelectric point.

In one embodiment a buffer for use in the present invention may have a pH value of at least about pH 5.0, suitably at least about pH 6.0.

In another embodiment a buffer for use in the present invention may have a pH value of at least about pH 6.5, at least about pH 7.0 or at least about pH 7.5.

Preferably, a buffer for use in the present invention may have a pH value of at least about pH 8.0.

In one embodiment a buffer for use in the present invention may have a pH value of between about pH 5.0 to about pH 9.5, suitably between about pH 6.0 to about pH 9.5.

Suitably a buffer for use in the present invention may have a pH value of between about pH 5.0 to about pH 9.0, suitably between about pH 6.0 to about pH 9.0.

In another embodiment, a buffer for use in the present invention may have a pH value of between about pH 6.5 to about pH 8.5, suitably between about pH 7.0 to about pH 8.0.

In one embodiment, a buffer for use in the present invention may have a pH value of about pH 6.0, suitably about pH 6.5 or about pH 7.0.

In another embodiment, a buffer for use in the present invention may have a pH value of about pH 7.5.

Preferably a buffer for use in the present invention may have a pH value of about pH 8.0.

The isoelectric point (pI) is a specific property of a given protein. As is well known in the art, proteins are made from a specific sequence of amino acids (also referred to when in a protein as amino acid residues). Each amino acid of the standard set of twenty has a different side chain (or R group), meaning that each amino acid residue in a protein displays different chemical properties such as charge and hydrophobicity. These properties may be influenced by the surrounding chemical environment, such as the temperature and pH. The overall chemical characteristics of a protein will depend on the sum of these various factors.

Certain amino acid residues (detailed below) possess ionisable side chains that may display an electric charge depending on the surrounding pH. Whether such a side chain is charged or not at a given pH depends on the pKa of the relevant ionisable moiety, wherein pKa is the negative logarithm of the acid dissociation constant (Ka) for a specified proton from a conjugate base.

For example, acidic residues such as aspartic acid and glutamic acid have side chain carboxylic acid groups with pKa values of approximately 4.1 (precise pKa values may depend on temperature, ionic strength and the microenvironment of the ionisable group). Thus, these side chains exhibit a negative charge at a pH of 7.4 (often referred to as "physiological pH"). At low pH values, these side chains will become protonated and lose their charge.

Conversely, basic residues such as lysine and arginine have nitrogen-containing side chain groups with pKa values of approximately 10-12. These side chains therefore exhibit a positive charge at a pH of 7.4. These side chains will become de-protonated and lose their charge at high pH values.

The overall (net) charge of a protein molecule therefore depends on the number of acidic and basic residues present in the protein (and their degree of surface exposure) and on the surrounding pH. Changing the surrounding pH changes the overall charge on the protein. Accordingly, for every protein there is a given pH at which the number of positive and negative charges is equal and the protein displays no overall net charge. This point is known as the isoelectric point (pI). The isoelectric point is a standard concept in protein biochemistry with which the skilled person would be familiar.

The isoelectric point (pI) is therefore defined as the pH value at which a protein displays a net charge of zero. An increase in pI means that a higher pH value is required for the protein to display a net charge of zero. Thus, an increase in pI represents an increase in the net positive charge of a protein at a given pH. Conversely, a decrease in pI means that a lower pH value is required for the protein to display a net charge of zero. Thus, a decrease in pI represents a decrease in the net positive charge of a protein at a given pH.

Methods of determining the pI of a protein are known in the art and would be familiar to a skilled person. By way of example, the pI of a protein can be calculated from the average pKa values of each amino acid present in the protein ("calculated pI"). Such calculations can be performed using computer programs known in the art; preferred example computer programs for calculating pI values include Protein Calculator from the Scripps Research Institute and Compute pI/MW Tool from ExPASy. Comparisons of pI values between different molecules should be made using the same calculation technique/program.

In a particularly preferred embodiment the "calculated pI" may refer to a pI calculated using the Scripps Protein Calculator v3.4, which is an online tool available at www.scripps.edu/~cdputnam/protcalc (the contents of which is incorporated herein by reference).

Where appropriate, the calculated pI of a protein can be confirmed experimentally using the technique of isoelectric focusing ("observed pI"). This technique uses electrophoresis to separate proteins according to their pI. Isoelectric focusing is typically performed using a gel that has an immobilised pH gradient. When an electric field is applied, the protein migrates through the pH gradient until it reaches the pH at which it has zero net charge, this point being the pI of the protein. Results provided by isoelectric focusing are typically relatively low-resolution in nature, and thus the present inventors believe that results provided by calculated pI (as described above) are more appropriate to use.

Throughout the present specification, "pI" means "calculated pI" unless otherwise stated.

The pI of a protein may be increased or decreased by altering the number of basic and/or acidic groups displayed on its surface. This can be achieved by modifying one or more amino acids of the protein. For example, an increase in pI may be provided by reducing the number of acidic residues, or by increasing the number of basic residues. Such amino acid modifications are discussed in more detail below.

By way of example, the calculated pI of BoNT/A (SEQ ID No. 14) is 6.4. The calculated pI is also provided for cationic BoNTs: Cat-A, Cat-B and Cat-C which are taught in WO2015/004461; as well as for Cat $H_N$_V1, Cat $H_N$_v2 and Cat $H_N$_v3.

Determination of the pH for use in the present invention is achieved with reference to the pI of the clostridial toxin being purified. For example, if the object of the purification is cationic rBoNT/A (SEQ ID No. 2), which has an calculated pI of 7.4, the pH value for use in the invention is pH 6.4 or above. Likewise if "Cat-A" (SEQ ID No. 16) which has a pI of 7.3, the pH value for use in the invention is about pH 6.3 or above.

TABLE 1

Calculated pI values for a number of clostridial neurotoxins.

| Clostridial Neurotoxin | Calculated pI |
|---|---|
| Cationic rBoNT/A (SEQ ID No. 2) | 7.4 |
| rBoNT/A (endonegative BoNT/A) (SEQ ID No. 4) | 6.5 |
| Cat $H_N$_v1 (SEQ ID No. 6) | 7.4 |
| Cat $H_N$_v2 (SEQ ID No. 8) | 7.3 |
| Cat $H_N$_v3 (SEQ ID No. 10) | 7.1 |
| Engineered "Cat-A" [Cat5v2(K1064H/N886K)] (SEQ ID No. 16) | 7.3 |
| Engineered "Cat-B" [Cat5v2(K1064/N954K)] (SEQ ID No. 18) | 7.3 |
| Engineered "Cat-C" [Cat5v2(K1064H/N1025K)] (SEQ ID No. 20) | 7.3 |

The 20 standard amino acids found in proteins are as shown in Table 2.

TABLE 2

Amino acids.

| AMINO ACID | | | SIDE CHAIN |
|---|---|---|---|
| Aspartic acid | Asp | D | Charged (acidic) |
| Glutamic acid | Glu | E | Charged (acidic) |
| Arginine | Arg | R | Charged (basic) |
| Lysine | Lys | K | Charged (basic) |
| Histidine | His | H | Uncharged (polar) |
| Asparagine | Asn | N | Uncharged (polar) |
| Glutamine | Gln | Q | Uncharged (polar) |
| Serine | Ser | S | Uncharged (polar) |
| Threonine | Thr | T | Uncharged (polar) |
| Tyrosine | Tyr | Y | Uncharged (polar) |
| Methionine | Met | M | Uncharged (polar) |
| Tryptophan | Trp | W | Uncharged (polar) |
| Cysteine | Cys | C | Uncharged (polar) |
| Alanine | Ala | A | Uncharged (hydrophobic) |
| Glycine | Gly | G | Uncharged (hydrophobic) |
| Valine | Val | V | Uncharged (hydrophobic) |
| Leucine | Leu | L | Uncharged (hydrophobic) |
| Isoleucine | Ile | I | Uncharged (hydrophobic) |
| Proline | Pro | P | Uncharged (hydrophobic) |
| Phenylalanine | Phe | F | Uncharged (hydrophobic) |

The following amino acids are considered charged amino acids: aspartic acid (negative), glutamic acid (negative), arginine (positive), and lysine (positive).

At a pH of 7.4, the side chains of aspartic acid (pKa 3.1) and glutamic acid (pKa 4.1) have a negative charge, while the side chains of arginine (pKa 12.5) and lysine (pKa 10.8) have a positive charge. Aspartic acid and glutamic acid are referred to as acidic amino acid residues. Arginine and lysine are referred to as basic amino acid residues.

The following amino acids are considered uncharged, polar (meaning they can participate in hydrogen bonding) amino acids: asparagine, glutamine, histidine, serine, threonine, tyrosine, cysteine, methionine, and tryptophan.

The following amino acids are considered uncharged, hydrophobic amino acids: alanine, valine, leucine, isoleucine, phenylalanine, proline, and glycine.

The method and/or use according to the present invention suitably results in an increased binding and/or yield of a clostridial neurotoxin. Suitably, the "increased binding and/or yield" may be determined by comparison of binding and/or yield obtained using a method and/or use of the invention with a similar method and/or use utilising a pH value different to that of the invention but which is otherwise identical.

The term "binding" as used in this context herein refers to association of a clostridial neurotoxin with a cation exchange resin. The concentration of bound clostridial neurotoxin may be determined by comparing the concentration of clostridial neurotoxin in a starting composition before contacting with a cation exchange resin and the concentration (if any) of clostridial neurotoxin remaining in a solution that has been contacted with a cation exchange resin. In some embodiments the concentration of clostridial neurotoxin in a starting composition may be compared with the concentration of clostridial neurotoxin in a flow-through fraction that represents proteins in a composition that do not associate with a cation exchange resin.

The methods and/or uses of the present invention may achieve a binding of at least about 50% of total clostridial neurotoxin comprised in a composition. Suitably the method and/or use may achieve a binding of at least about 60% or 70% of total clostridial neurotoxin comprised in a composition.

Suitably the method and/or use may achieve a binding of at least about 80% or 90% of total clostridial neurotoxin comprised in a composition. Preferably a binding of at least about 95%, 97% or 99%.

The term "yield" as used herein refers to the amount (e.g. concentration) of clostridial neurotoxin obtained after carrying out a method and/or use of the invention. In some embodiments the "yield" may be calculated by comparing the amount (e.g. concentration) of clostridial neurotoxin in a starting composition with the amount (e.g. concentration) of clostridial neurotoxin present in a fraction eluted from a cation exchange resin.

The method and/or use of the present invention may further comprise separating a clostridial neurotoxin from a cation exchange residue. This may herein be referred to as "elution". The separation may be achieved by the use of an appropriate elution buffer. Typically for ion exchange chromatography (e.g. cation exchange chromatography) a buffer is designed comprising an appropriate concentration of an appropriate salt which displaces a bound protein from the ion exchange resin (e.g. cation exchange resin).

In some embodiments a clostridial neurotoxin associated with a cation exchange resin may be exposed to an elution buffer. Suitably any solution may then be separated from the cation exchange resin. For example, when using a column one or more fractions may be collected.

Therefore in one embodiment there is provided a clostridial neurotoxin comprised in an elution buffer.

In another embodiment there is provided a purification intermediate comprised in an elution buffer.

In a yet further embodiment there is provided a clostridial neurotoxin obtainable by a method and/or use of the invention comprised in an elution buffer.

In one embodiment a gradient concentration of elution buffer may be applied to a cation exchange resin associated with a clostridial neurotoxin. The gradient may be prepared by admixing an elution buffer having a desired salt concentration (e.g. a salt concentration that is higher than the concentration from which a clostridial neurotoxin elutes from a cation exchange resin) with one or more additional buffer(s) having a different (e.g. lower) salt concentration.

In some embodiments a clostridial neurotoxin separated from a cation exchange resin may be in a substantially pure state.

The term "pure state" as used herein is meant to refer to a state in which a clostridial neurotoxin is free from non-clostridial neurotoxin contaminants (e.g. protein contaminants).

The term "substantially pure" as used herein means that in a given composition a clostridial neurotoxin is mostly free from non-clostridial neurotoxin contaminants (e.g. protein contaminants) and accounts for at least about 85%, 90% or 95% of the total protein concentration. Suitably the clostridial neurotoxin may account for at least about 97%, 99% or 99.9% of the total protein concentration.

Therefore the present invention provides a clostridial neurotoxin obtainable (e.g. obtained) by a method or use of the present invention. Suitably the clostridial neurotoxin may be a substantially pure clostridial neurotoxin.

In one embodiment the invention provides a purification intermediate comprising a clostridial neurotoxin associated with a cation exchange resin, wherein the purification intermediate has a pH value of at least pH 7.3.

In another embodiment the invention provides a purification intermediate comprising a clostridial neurotoxin which has been separated from a cation exchange resin, wherein the purification intermediate has a pH value of at least pH 7.3.

In one embodiment a purification intermediate may have a pH value that is at least about pH 7.3 (suitably at least pH 7.4 or pH 7.5).

Suitably, a purification intermediate may have a pH value that is at least about pH 7.6 or at least about pH 7.7.

Suitably, a purification intermediate may have a pH value that is at least about pH 7.8 or at least about pH 7.9.

Suitably, a purification intermediate may have a pH value that is at least about pH 8.0.

In another embodiment a purification intermediate may have a pH between about pH 7.5 to about pH 9.5. Suitably, a purification intermediate may have a pH between about pH 7.5 to about pH 9.0, or between about pH 7.5 to about pH 8.5.

Suitably, a purification intermediate may have a pH value of about pH 7.5.

Suitably, a purification intermediate may have a pH value of about pH 8.0.

The term "purification intermediate" as used herein is intended to refer to a clostridial neurotoxin which has been subjected or is in the process of being subjected to at least one purification step but which has not been subjected to all of the purification steps intended by the skilled worker. In some embodiments the purification intermediate may be in a substantially pure state.

In one embodiment a clostridial neurotoxin may be obtainable (e.g. obtained) from a purification intermediate of the invention. Suitably the clostridial neurotoxin may be in a substantially pure state.

A purification intermediate and/or a clostridial neurotoxin according to the present invention may be distinguished from a purification intermediate and/or a clostridial neurotoxin obtainable by an alternative method by at least the pH value of the buffer in which said purification intermediate and/or clostridial neurotoxin is comprised.

In other words, a buffer in which a purification intermediate and/or a clostridial neurotoxin according to the present invention may have a pH value of at least about pH 7.3.

Suitably the buffer may have a pH value that is at least pH 7.3 and further comprise a salt concentration that is consistent with a cation exchange elution buffer.

The elution buffer may comprise one or more of: NaCl, KCl, $CaCl_2$, $MgCl_2$ and $(NH_4)_2SO_4$.

In one embodiment such a buffer may have a pH value that is at least about pH 7.3 and may comprise at least about 50 mM NaCl or at least about 100 mM NaCl.

In another embodiment such a buffer may have a pH value that is at least about pH 7.3 and may comprise at least about 200 mM NaCl or at least about 300 mM NaCl (suitably at least about 400 mM NaCl or at least about 500 mM NaCl).

In one embodiment such a buffer may have a pH value that is at least about pH 7.3 and may comprise at least about 50 mM KCl or at least about 100 mM KCl.

In another embodiment such a buffer may have a pH value that is at least about pH 7.3 and may comprise at least about 200 mM KCl or at least about 300 mM KCl (suitably at least about 400 mM KCl or at least about 500 mM KCl).

In one embodiment such a buffer may have a pH value that is at least about pH 7.3 and may comprise at least about 50 mM $CaCl_2$ or at least about 100 mM $CaCl_2$.

In another embodiment such a buffer may have a pH value that is at least about pH 7.3 and may comprise at least about 200 mM $CaCl_2$ or at least about 300 mM $CaCl_2$ (suitably at least about 400 mM $CaCl_2$ or at least about 500 mM $CaCl_2$).

In one embodiment such a buffer may have a pH value that is at least about pH 7.3 and may comprise at least about 50 mM $MgCl_2$ or at least about 100 mM $MgCl_2$.

In another embodiment such a buffer may have a pH value that is at least about pH 7.3 and may comprise at least about 200 mM $MgCl_2$ or at least about 300 mM $MgCl_2$ (suitably at least about 400 mM $MgCl_2$ or at least about 500 mM $MgCl_2$).

In one embodiment such a buffer may have a pH value that is at least about pH 7.3 and may comprise at least about 50 mM $(NH_4)_2SO_4$ or at least about 100 mM $(NH_4)_2SO_4$.

In another embodiment such a buffer may have a pH value that is at least about pH 7.3 and may comprise at least about 200 mM $(NH_4)_2SO_4$ or at least about 300 mM $(NH_4)_2SO_4$ (suitably at least about 400 mM $(NH_4)_2SO_4$ or at least about 500 mM $(NH_4)_2SO_4$).

A buffer for use in the present invention may preferably further comprise 50 mM Bis-Tris Propane pH 8.0.

When eluting from a cation exchange residue in accordance with the present invention a buffer comprising 50 mM Bis-Tris Propane pH 8.0 may be used in combination with an elution gradient of about 0 to about 500 mM of salt. Suitably the salt may be selected from the group consisting of: NaCl, KCl, $CaCl_2$, $MgCl_2$ and $(NH_4)_2SO_4$) (preferably NaCl).

A buffer having a pH value that is −1 pH unit or higher than the calculated pI of a clostridial neurotoxin for use in a use of the invention may be an elution buffer. The elution buffer may comprise one or more of: NaCl, KCl, $CaCl_2$, $MgCl_2$ and $(NH_4)_2SO_4$.

In one embodiment such a buffer may have a pH value that is at least −1 pH unit or higher than the calculated pI of the clostridial neurotoxin and may comprise at least about 50 mM NaCl or at least about 100 mM NaCl.

In another embodiment such a buffer may have a pH value that is at least −1 pH unit or higher than the calculated pI of the clostridial neurotoxin and may comprise at least about 200 mM NaCl or at least about 300 mM NaCl (suitably at least about 400 mM NaCl or at least about 500 mM NaCl).

In one embodiment such a buffer may have a pH value that is at least −1 pH unit or higher than the calculated pI of the clostridial neurotoxin and may comprise at least about 50 mM KCl or at least about 100 mM KCl.

In another embodiment such a buffer may have a pH value that is at least −1 pH unit or higher than the calculated pI of the clostridial neurotoxin and may comprise at least about 200 mM KCl or at least about 300 mM KCl (suitably at least about 400 mM KCl or at least about 500 mM KCl).

In one embodiment such a buffer may have a pH value that is at least −1 pH unit or higher than the calculated pI of the clostridial neurotoxin and may comprise at least about 50 mM $CaCl_2$ or at least about 100 mM $CaCl_2$.

In another embodiment such a buffer may have a pH value that is at least −1 pH unit or higher than the calculated pI of the clostridial neurotoxin and may comprise at least about 200 mM $CaCl_2$ or at least about 300 mM $CaCl_2$ (suitably at least about 400 mM $CaCl_2$ or at least about 500 mM $CaCl_2$).

In one embodiment such a buffer may have a pH value that is at least −1 pH unit or higher than the calculated pI of the clostridial neurotoxin and may comprise at least about 50 mM $MgCl_2$ or at least about 100 mM $MgCl_2$.

In another embodiment such a buffer may have a pH value that is at least −1 pH unit or higher than the calculated pI of the clostridial neurotoxin and may comprise at least about 200 mM $MgCl_2$ or at least about 300 mM $MgCl_2$ (suitably at least about 400 mM $MgCl_2$ or at least about 500 mM $MgCl_2$).

In one embodiment such a buffer may have a pH value that is at least −1 pH unit or higher than the calculated pI of the clostridial neurotoxin and may comprise at least about 50 mM $(NH_4)_2SO_4$ or at least about 100 mM $(NH_4)_2SO_4$.

In another embodiment such a buffer may have a pH value that is at least −1 pH unit or higher than the calculated pI of the clostridial neurotoxin and may comprise at least about 200 mM $(NH_4)_2SO_4$ or at least about 300 mM $(NH_4)_2SO_4$ (suitably at least about 400 mM $(NH_4)_2SO_4$ or at least about 500 mM $(NH_4)_2SO_4$).

A buffer for use in the present invention may preferably further comprise 50 mM Bis-Tris Propane pH 8.0.

When eluting from a cation exchange residue in accordance with the present invention a buffer comprising 50 mM Bis-Tris Propane pH 8.0 may be used in combination with an elution gradient of about 0 to about 500 mM of salt. Suitably the salt may be selected from the group consisting of: NaCl, KCl, $CaCl_2$, $MgCl_2$ and $(NH_4)_2SO_4$ (preferably NaCl).

Sequence Homology

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position—Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics:1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment Scores for Determining Sequence Identity

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

The percent identity is then calculated as:

$$\frac{\text{Total number of identical matches}}{[\text{length of the longer sequence plus the number of gaps introduced into the longer sequence in order to align the two sequences}]} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions
Basic: arginine
  lysine
  histidine
Acidic: glutamic acid
  aspartic acid
Polar: glutamine
  asparagine
Hydrophobic: leucine
  isoleucine
  valine
Aromatic: phenylalanine
  tryptophan
  tyrosine
Small: glycine
  alanine
  serine
  threonine
  methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine.

Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an E. coli S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in Xenopus oocytes by microinjection of mutated mRNA and chemically aminoacylated suppressor tRNAs (Turcatti et al., J. Biol. Chem. 271:19991-8, 1996). Within a third method, E. coli cells are cultured in the absence of a natural amino acid that is to be replaced (e.g., phenylalanine) and in the presence of the desired non-naturally occurring amino acid (s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

ADVANTAGES

In accordance with the foregoing embodiments, it is a seminal finding by the present inventors that a clostridial neurotoxin is capable of interacting with a cation exchange resin at a pH value of at least pH 7.3. This is unexpected because (without wishing to be bound by theory) such a clostridial neurotoxin is at a pH value higher than its calculated pI and is believed to have an overall negative charge. Thus, it is highly surprising that it would be capable of interacting (especially with such a high binding efficiency) with a cation exchange resin, which is known to associate with positively-charged proteins.

A further advantage of the present invention is that the same pH can be maintained throughout the purification process. In other words the need for time-consuming buffer changes (in similar methods where a pH value of less than pH 7.3 is used) is reduced and/or eliminated, thus improving efficiency and/or throughput. Additionally or alternatively maintaining the same pH throughout the purification process advantageously means that the physical manipulation of a composition comprising a clostridial neurotoxin and/or purification intermediate and/or clostridial neurotoxin is reduced.

Uses comprising contacting a cation exchange resin with a composition comprising a clostridial neurotoxin, wherein the contacting occurs at a pH of −1 pH unit or higher than the calculated isoelectric point of said clostridial neurotoxin result in a number of improved properties. For example, such uses achieve increased binding and/or yield of a clostridial neurotoxin when compared to a similar use where the contacting does not occur at a pH value that is −1 pH unit or higher than the calculated isoelectric point of said clostridial neurotoxin.

Without wishing to be bound by theory, it is believed that by contacting a clostridial neurotoxin and cation exchange column under the pH conditions indicated, that increased binding of clostridial neurotoxin to a cation exchange column prevents contaminants (e.g. protein contaminants) present in the composition binding and thus co-eluting with the clostridial toxin.

Enhanced binding of a clostridial neurotoxin to a cation exchange resin also improves the efficiency of purification, resulting in increased yields and/or reduced costs associated with each purification. In other words a less wasteful and/or more economic purification process is provided.

The methods and/or uses of the invention advantageously mean that fewer purification steps need to be employed to obtain a clostridial neurotoxin of a grade suitable for use in therapy and/or medicine.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a clostridial neurotoxin" includes a plurality of such candidate agents and reference to "the clostridial neurotoxin" includes reference to one or more clostridial neurotoxins and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The invention will now be described, by way of example only, with reference to the following Figures and Examples.

EXAMPLES

Example 1—Culturing of Host and Expression of Soluble rBoNT/A Proteins

A single colony of BL21 (DE3) cells, transformed with an expression vector containing an rBoNT/A DNA sequence (SEQ ID No. 1 or 3), was used to inoculate 100 mL of modified Terrific Broth (mrTB) supplemented with 30 µg/mL kanamycin. This method would be equally applicable when using a MICROBANK® bead or glycerol stock (10-100 μL) to inoculate the flask. The culture was incubated for 16 h at 37° C. with 250 RPM shaking.

Following incubation, a total of 10 mL of the 100 mL culture was used to inoculate 1 L of mTB supplemented with 0.2% glucosamine and 30 μg/mL kanamycin. The culture was incubated at 37° C. with 250 RPM until an $OD_{600}$ of 0.5 was reached. At this point, the incubation temperature was dropped to 16° C. After 1 h, expression of the target protein was induced with 1 mM IPTG followed by incubation at 16° C. for 20 h with 225 RPM shaking. Following incubation, the cells were harvested by centrifugation at 4000×g for 20 min at 4° C. and then stored at −20° C.

Example 2—Extraction of rBoNT/A Proteins from Host Cells

Cell pastes were thawed at room temperature and resuspended in 3 mL of 50 mM Bis-Tris pH 6.0, 50 mM NaCl buffer per gram of cells, 10 μL BENZONASE® Nuclease was then added to the cell suspension. Cells were lysed, at 0-4° C., by sonication at 100 W (10 cycles of 30 s on and 45 s off). The lysates were centrifuged at 4000×g for 1 h at 4° C. to afford the soluble rBoNT/A (SEQ ID No. 2 or 4) in the clarified supernatant.

Example 3—Capture of Target rBoNT/A Protein

The properties of the rBoNT/A proteins were determined from the primary protein sequence using the Scripps Protein Calculator v3.4 from the Scripps Research Institute (Table 3).

TABLE 3

| Predicted properties of rBoNT/A | |
|---|---|
| Clostridial Neurotoxin | Calculated pI |
| rBoNT/A (endonegative BoNT/A) (SEQ ID No. 4) | 6.5 |
| Cationic rBoNT/A (SEQ ID No. 2) | 7.4 |

Based on the calculated pI values, it was predicted that rBoNT/A (SEQ ID No. 4) and cationic rBoNT/A (SEQ ID No. 2) would bind to a cation exchange (CEX) resin at a buffer pH<6.5 and <7.4, respectively.

Example 4—Desalting of the Clarified Lysate into Test Buffers

The clarified lysates containing soluble rBoNT/A (SEQ ID No. 2 and 4) were divided into equal portions and buffer exchanged into the loading buffers listed in Table 4 using an Econo-Pac 10DG desalting column.

TABLE 4

| Loading buffers used for CEX buffer scouting. | |
|---|---|
| Condition # | Loading buffer |
| 1 | Citrate phosphate buffer, pH 6.0 |
| 2 | 50 mM Bis-Tris methane, pH 6.0 |
| 3 | 50 mM HEPES, pH 7.5 |
| 4 | 50 mM Bis-Tris methane, pH 7.5 |
| 5 | 50 mM Tris, pH 8.0 |
| 6 | 50 mM Bis-Tris propane, pH 8.0 |

The buffer exchanged, clarified lysates were stored at 4° C. prior to loading onto a HITRAP® SP HP column.

Example 5—Buffer Screening for CEX Chromatography Capture Step of rBoNT/A (SEQ ID No. 4) Using Fast Protein Liquid Chromatography (FPLC)

The buffer exchanged lysates containing soluble rBoNT/A (SEQ ID No. 4) were loaded onto a HITRAP® SP HP column. The % binding and % purity of eluted target protein was determined by SDS-PAGE and densitometry. Elution of bound protein was achieved by employing either a pH or NaCl linear gradient (Table 5).

TABLE 5

| Loading buffers and elution gradient used for CEX buffer scouting. | | |
|---|---|---|
| Condition # | Loading Buffer | Elution Gradient |
| 1 | Citrate phosphate buffer, pH 6.0 | pH 6.0 to pH 7.5 |
| 2 | 50 mM Bis-Tris methane, pH 6.0 | 0 to 1M NaCl |
| 3 | 50 mM HEPES, pH 7.5 | 0 to 1M NaCl |
| 4 | 50 mM Bis-Tris methane, pH 7.5 | 0 to 1M NaCl |
| 5 | 50 mM Tris, pH 8.0 | 0 to 1M NaCl |
| 6 | 50 mM Bis-Tris propane, pH 8.0 | 0 to 1M NaCl |

FIG. 1 (panels A-F) shows COOMASSIE® stained SDS-PAGE gels of the rBoNT/A (SEQ ID No. 4) elution profiles following binding to, and elution from the SP HP SEPHAROSE® resin using the conditions in Table 5. Analysis of the SDS-PAGE gels allowed for estimation of the % purity of the eluted target protein (Table 6).

TABLE 6

| Analysis of rBoNT/A (SEQ ID No. 4) binding to SP HP SEPHAROSE ® resin | | |
|---|---|---|
| Condition # | Loading Buffer | % Purity of eluted target protein[†] |
| 1 | Citrate phosphate buffer, pH 6.0 | n.d |
| 2 | 50 mM Bis-Tris methane, pH 6.0 | 70% |
| 3 | 50 mM HEPES, pH 7.5 | 35% |
| 4 | 50 mM Bis-Tris methane, pH 7.5 | 25% |
| 5 | 50 mM Tris, pH 8.0 | 60% |
| 6 | 50 mM Bis-Tris propane, pH 8.0 | 40% |

[†]Densitometric analysis of SDS-PAGE gels.

Visual assessment of the SDS-PAGE gels (FIG. 1) shows a greater recover of target protein after elution with conditions 3-6, which suggests greater initial binding of the target protein to the resin.

Example 6—Buffer Screening for CEX Chromatography Capture Step of Cationic rBoNT/A (SEQ ID No. 2) Using Fast Protein Liquid Chromatography (FPLC)

The buffer exchanged lysates containing soluble cationic rBoNT/A (SEQ ID No. 2) were loaded onto a HITRAP® SP HP column. The binding and % purity of the elated target protein was determined by SDS-PAGE analysis. Elution of bound protein was achieved by employing either a pH or NaCl linear gradient (Table 5).

Figure 2:
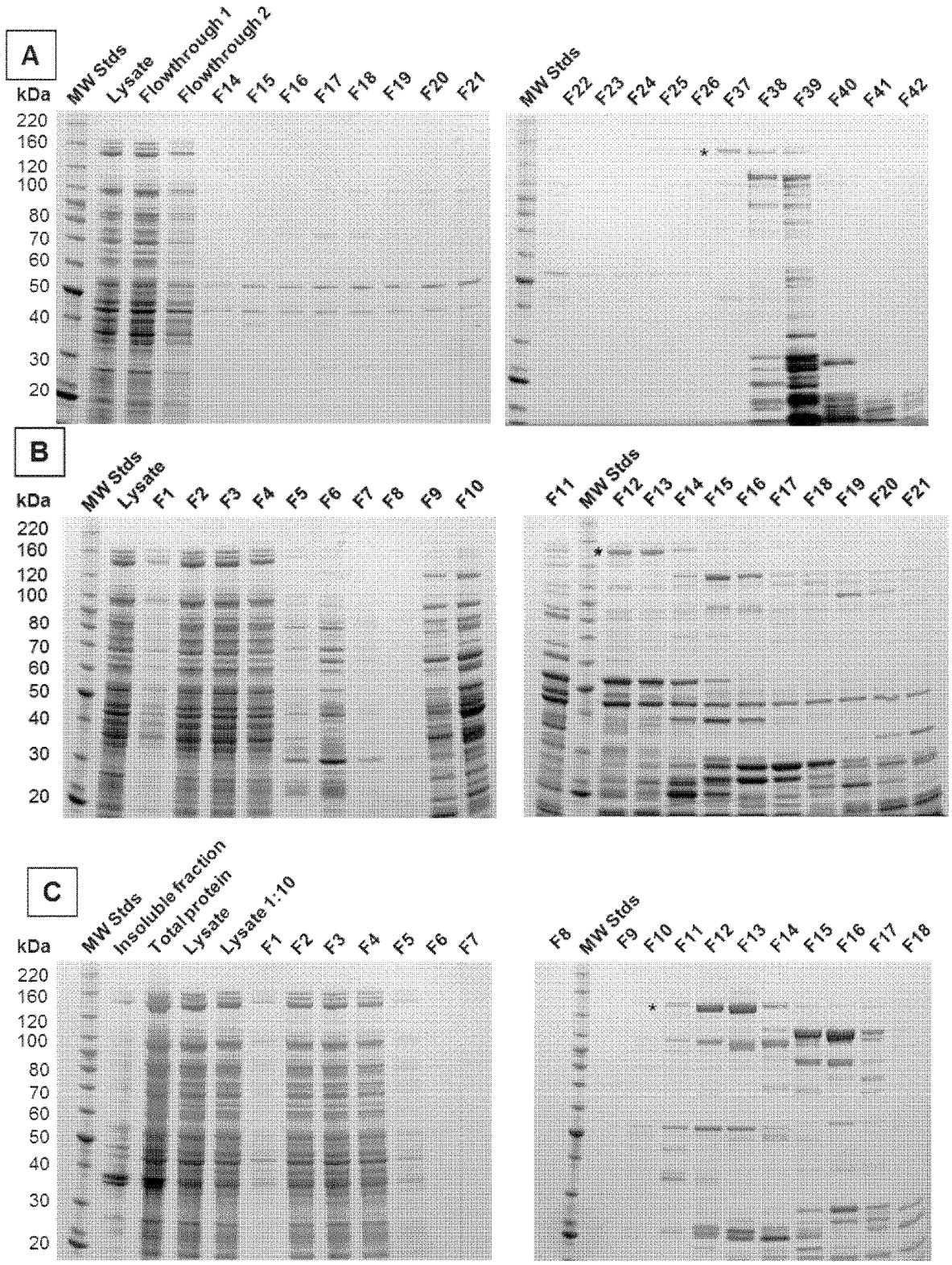
FIG. 2 shows cationic rBoNT/A1 capture on cation exchange resins at different pH. E. coli lysates of endonegative cationic rBoNT/A1 were buffer exchanged to pH 6.0 (panels A and B), pH 7.5 (panels C and D), or pH 8.0 (panels E and F). Lysates were loaded onto Hi-Trap SP-HP, washed, and eluted with either a pH (panel A) or NaCl (panels B-F) gradient. Relevant fractions were analysed by SDS-PAGE, and BoNT/A is indicated with an asterisk (*) on each panel.
Figure 2:
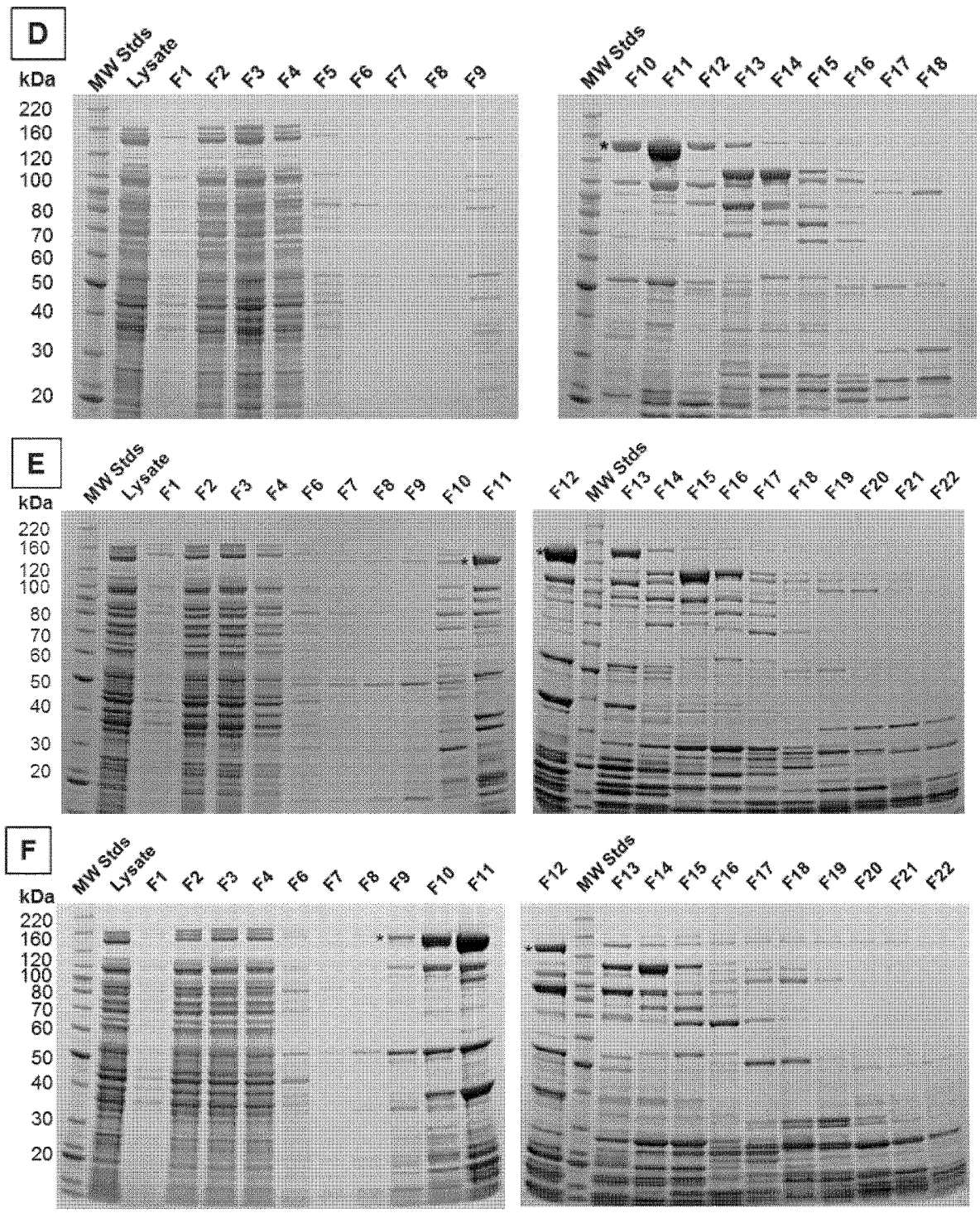

FIG. 2 (panels A-F) shows COOMASSIE® stained SDS-PAGE gels of the cationic rBoNT/A (SEQ ID No. 2) elution profiles following binding to, and elution from the SP HP SEPHAROSE® resin using the conditions in Table 5.

Analysis of the SDS-PAGE gels allowed for estimation of the % purity and % binding of the target protein to the SP HP SEPHAROSE® resin (Table 7).

TABLE 7

Analysis of cationic rBoNT/A (SEQ ID No. 2) binding to SP HP SEPHAROSE ® resin

| Buffer | Loading Buffer | % Binding to SP HP SEPHAROSE ® resin* | % Purity of eluted target protein† |
|---|---|---|---|
| 1 | Citrate phosphate buffer, pH 6.0 | v poor <10% | 50% |
| 2 | 50 mM Bis-Tris methane, pH 6.0 | Ok ~30% | 10% |
| 3 | 50 mM HEPES, pH 7.5 | Good ~60% | 35% |
| 4 | 50 mM Bis-Tris methane, pH 7.5 | Good ~60% | 40% |
| 5 | 50 mM Tris, pH 8.0 | Good ~60% | 25% |
| 6 | 50 mM Bis-Tris propane, pH 8.0 | Good ~60% | 35% |

*Visual assessment and estimation of % binding

†Densitometric analysis of SDS-PAGE gels.

Assessment of the SDS-PAGE gels (FIG. 2) shows greater % binding and similar % purity of the target protein at pH 7.5-8.0 compared to pH 6.0. This equates to an overall increase in target protein recovery.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method of producing the active di-chain form of a clostridial neurotoxin, the method comprising:
   (a) contacting a cation exchange resin with a composition comprising a single-chain clostridial neurotoxin, wherein the contacting step is performed at a pH of from 7.3 to 9.5;
   (b) separating the clostridial neurotoxin from the cation exchange resin and
   (c) contacting the separated clostridial neurotoxin with a protease that cleaves the polypeptide sequence of the clostridial neurotoxin under conditions suitable for the cleavage, thereby activating it to produce the active di-chain form of the clostridial neurotoxin,
wherein the step (a) occurs before the step (b).

2. The method of claim 1, wherein the separated clostridial neurotoxin is in a substantially pure state.

3. The method of claim 1, wherein the contacting step is performed at a pH of from 7.5 to 9.0.

4. The method of claim 1, wherein the contacting step is performed at a pH of from 7.5 to 8.5.

5. The method of claim 1, wherein the contacting step is performed at a pH of from 7.3 to 8.0.

6. The method of claim 1, wherein the contacting step is performed in a buffer having a pH that is −1 pH unit or higher than the calculated pI of the clostridial neurotoxin.

7. The method of claim 6, wherein the buffer has a pH value that is equal to or higher than the calculated pI of said clostridial neurotoxin.

8. The method of claim 6, wherein the buffer has a pH of between 0.2 and 1.5 pH units higher than the calculated pI of said clostridial neurotoxin.

9. The method of claim 6, wherein the buffer has a pH of between 0.2 and 1.0 pH units higher than the calculated pI of said clostridial neurotoxin.

10. The method of claim 1, further comprising contacting the composition comprising the single-chain clostridial neurotoxin with one or more additional resins.

11. The method of claim 1, wherein at least 35% of the total clostridial neurotoxin comprised in the composition associates with the cation exchange resin.

12. The method of claim 1, wherein the clostridial neurotoxin is a *Clostridium botulinum* neurotoxin, a *Clostridium tetani* neurotoxin, a *Clostridium baratii* neurotoxin, or a *C. butyricum* neurotoxin.

13. The method of claim 1, wherein the clostridial neurotoxin is a botulinum neurotoxin (BoNT).

14. The method of claim 13, wherein the BoNT is a cationic BoNT.

15. The method of claim 1, wherein the protease is an endoprotease.

16. The method of claim 15, wherein the endoprotease is Lys-C.

* * * * *

SEQUENCE LISTING

<160> NUMBER OF SEQ ID NOS: 28

<210> SEQ ID NO 1
<211> LENGTH: 3888
<212> TYPE: DNA
<213> ORGANISM: Artificial Sequence
<220> FEATURE:
<223> OTHER INFORMATION: nucleotide encoding synthetic cationic BoNT/A1

<400> SEQUENCE: 1
atgccattcg tcaacaagca attcaactac aaagacccag tcaacggcgt cgacatcgca 60
tacatcaaga ttccgaacgc cggtcaaatg cagccggtta aggcttttaa gatccacaac 120
aagatttggg ttatcccgga gcgtgacacc ttcacgaacc cggaagaagg cgatctgaac 180
ccgccaccgg aagcgaagca agtccctgtc agctactacg attcgacgta cctgagcacg 240
gataacgaaa aagataacta cctgaaaggt gtgaccaagc tgttcgaacg tatctacagc 300
acggatctgg gtcgcatgct gctgactagc attgttcgcg gtatcccgtt ctggggtggt 360
agcacgattg acaccgaact gaaggttatc gacactaact gcattaacgt tattcaaccg 420
gatggtagct atcgtagcga agagctgaat ctggtcatca ttggcccgag cgcagacatt 480
atccaattcg agtgcaagag ctttggtcac gaggttctga atctgacccg caatggctat 540
ggtagcaccc agtacattcg tttttcgccg gattttacct tcggctttga agagagcctg 600
gaggttgata ccaatccgtt gctgggtgcg ggcaaattcg ctaccgatcc ggctgtcacg 660
ctggcccatc aactgatcta cgcaggccac cgcctgtacg gcattgccat caacccaaac 720
cgtgtgttca aggttaatac gaatgcatac tacgagatga gcggcctgga agtcagcttc 780
gaagaactgc gcaccttcgg tggccatgac gctaaattca ttgacagctt gcaagagaat 840
gagttccgtc tgtactacta taacaaattc aaagacattg caagcacgtt gaacaaggcc 900
aaaagcatcg ttggtactac cgcgtcgttg cagtatatga agaatgtgtt taaagagaag 960
tacctgctgt ccgaggatac ctccggcaag tttagcgttg ataagctgaa gtttgacaaa 1020
ctgtacaaga tgctgaccga gatttacacc gaggacaact ttgtgaaatt cttcaaagtg 1080
ttgaatcgta aaacctatct gaattttgac aaagcggttt tcaagattaa catcgtgccg 1140
aaggtgaact acaccatcta tgacggtttt aacctgcgta acaccaacct ggcggcgaac 1200
tttaacggtc agaatacgga aatcaacaac atgaatttca cgaagttgaa gaacttcacg 1260

```
ggtctgttcg agttctataa gctgctgtgc gtgcgcggta tcatcaccag caaaaccaaa      1320
agcctggaca aaggctacaa caaggcgctg aatgacctgt gcattaaggt aaacaattgg      1380
gatctgttct tttcgccatc cgaagataat tttaccaacg acctgaacaa gggtgaagaa      1440
atcaccagcg atacgaatat tgaagcagcg aagagaata tcagcctgga tctgatccag       1500
cagtactatc tgacctttaa cttcgacaat gaaccggaga acattagcat tgagaatctg      1560
agcagcgaca ttatcggtca gctggaactg atgccgaata tcgaacgttt cccgaacggc      1620
aaaaagtacg agctggacaa gtacactatg ttccattacc tgcgtgcaca ggagtttgaa      1680
cacggtaaaa gccgtatcgc gctgaccaac agcgttaacg aggccctgct gaacccgagc      1740
cgtgtctata ccttcttcag cagcgactat gttaagaaag tgaacaaagc cactgaggcc      1800
gcgatgttcc tgggctgggt ggaacagctg gtatatgact tcacggacga gacgagcgaa      1860
gtgagcacta ccgacaaaat tgctgatatt accatcatta tcccgtatat tggtccggca      1920
ctgaacattg gcaacatgct gtacaaagac gattttgtgg gtgccctgat cttctccggt      1980
gccgtgattc tgctggagtt cattccggag attgcgatcc cggtgttggg taccttcgcg      2040
ctggtgtcct acatcgcgaa taaggttctg acggttcaga ccatcgataa cgcgctgtcg      2100
aaacgtaatg aaaaatggga cgaggtttac aaatacattg ttacgaattg gctggcgaaa      2160
gtcaataccc agatcgacct gatccgtaag aaaatgaaag aggcgctgga gaatcaggcg      2220
gaggccacca aagcaattat caactaccaa tacaaccagt acacggaaga agagaagaat      2280
aacattaact tcaatatcga tgatttgagc agcaagctga atgaatctat caacaaagcg      2340
atgatcaata tcaacaagtt tttgaatcag tgtagcgttt cgtacctgat gaatagcatg      2400
attccgtatg gcgtcaaacg tctggaggac ttcgacgcca gcctgaaaga tgcgttgctg      2460
aaatacattt acgacaatcg tggtacgctg attggccaag ttgaccgctt gaaagacaaa      2520
gttaacaata ccctgagcac cgacatccca tttcaactga gcaagtatgt tgataatcaa      2580
cgtctgttga gcactttcac cgagtatatc aaaaacatca tcaatactag cattctgaac      2640
ctgcgttacg agagcaagca tctgattgat ctgagccgtt atgctagcaa gatcaacatc      2700
ggtagcaagg tcaattttga cccgatcgat aagaaccaga tccagctgtt taatctggaa      2760
tcgagcaaaa ttgaggttat cctgaaaaag gccattgtct acaactccat gtacgagaat      2820
ttctccacca gcttctggat tcgcatcccg aaatacttca acaagattag cctgaacaac      2880
gagtatacta tcatcaactg tatggagaac aacagcggtt ggaaggtgtc tctgaactat      2940
ggtgagatca tttggacctt gcaggacacc aaagagatca agcagcgcgt cgtgttcaag      3000
tactctcaaa tgatcaacat ttccgattac attaatcgtt ggatcttcgt gaccattacg      3060
aataaccgtc tgaataagag caagatttac atcaatggtc gcttgatcga tcagaaaccg      3120
attagcaacc tgggtaatat ccacgcaagc aacaagatta tgttcaaatt ggacggttgc      3180
cgcgataccc atcgttatat ctggatcaag tatttcaacc tgtttgataa agaactgaat      3240
gagaaggaga tcaaagattt gtatgacaac caatctaaca gcggcatttt gaaggacttc      3300
tggggcgatt atctgcaata cgataagccg tactatatgc tgaacctgta tgatccgaac      3360
aaatatgtgg atgtcaataa tgtgggtatt cgtggttaca tgtatttgaa gggtccgcgt      3420
ggcagcgtta tgacgaccaa catttacctg aactctagcc tgtaccgtgg tacgaaattc      3480
atcattaaga aatatgccag cggcaacaaa gataacattg tgcgtaataa cgatcgtgtc      3540
tacatcaacg tggtcgtgaa gaataaagag taccgtctgg cgaccaacgc ttcgcaggcg      3600
```

-continued

```
ggtgttgaga aaattctgag cgcgttggag atccctgatg tcggtaatct gagccaagtc    3660
gtggttatga agagcaagaa cgacaagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg                 3888
```

<210> SEQ ID NO 2
<211> LENGTH: 1296
<212> TYPE: PRT
<213> ORGANISM: Artificial Sequence
<220> FEATURE:
<223> OTHER INFORMATION: synthetic cationic BoNT/A1

<400> SEQUENCE: 2

```
Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Gln
    210                 215                 220

Leu Ile Tyr Ala Gly His Arg Leu Tyr Gly Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320
```

-continued

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Met Phe Leu Gly Trp Val Glu
            595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

```
Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
    755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Lys His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
            915                 920                 925

Lys Lys Ala Ile Val Tyr Asn Ser Met Tyr Glu Asn Phe Ser Thr Ser
930                 935                 940

Phe Trp Ile Arg Ile Pro Lys Tyr Phe Asn Lys Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Lys Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg
    1010                1015                1020

Leu Asn Lys Ser Lys Ile Tyr Ile Asn Gly Arg Leu Ile Asp Gln
    1025                1030                1035

Lys Pro Ile Ser Asn Leu Gly Asn Ile His Ala Ser Asn Lys Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
```

|  | 1145 | | | 1150 | | | | 1155 | | |
|---|---|---|---|---|---|---|---|---|---|---|

Lys Phe Ile Ile Lys Lys Tyr Ala Ser Gly Asn Lys Asp Asn Ile
    1160                       1165                         1170

Val Arg Asn Asn Asp Arg Val Tyr Ile Asn Val Val Lys Asn
    1175                     1180                       1185

Lys Glu Tyr Arg Leu Ala Thr Asn Ala Ser Gln Ala Gly Val Glu
    1190                     1195                         1200

Lys Ile Leu Ser Ala Leu Glu Ile Pro Asp Val Gly Asn Leu Ser
    1205                     1210                       1215

Gln Val Val Met Lys Ser Lys Asn Asp Lys Gly Ile Thr Asn
    1220                     1225                       1230

Lys Cys Lys Met Asn Leu Gln Asp Asn Asn Gly Asn Asp Ile Gly
    1235                     1240                       1245

Phe Ile Gly Phe His Gln Phe Asn Asn Ile Ala Lys Leu Val Ala
    1250                     1255                       1260

Ser Asn Trp Tyr Asn Arg Gln Ile Glu Arg Ser Ser Arg Thr Leu
    1265                     1270                       1275

Gly Cys Ser Trp Glu Phe Ile Pro Val Asp Asp Gly Trp Gly Glu
    1280                     1285                       1290

Arg Pro Leu
    1295

```
<210> SEQ ID NO 3
<211> LENGTH: 3888
<212> TYPE: DNA
<213> ORGANISM: Artificial Sequence
<220> FEATURE:
<223> OTHER INFORMATION: nucleotide encoding recombinant BoNT/A1
      (rBoNT/A1)

<400> SEQUENCE: 3
atgccattcg tcaacaagca attcaactac aaagacccag tcaacggcgt cgacatcgca      60
tacatcaaga ttccgaacgc cggtcaaatg cagccggtta aggcttttaa gatccacaac     120
aagatttggg ttatcccgga gcgtgacacc ttcacgaacc cggaagaagg cgatctgaac     180
ccgccaccgg aagcgaagca agtccctgtc agctactacg attcgacgta cctgagcacg     240
gataacgaaa agataactta cctgaaaggt gtgaccaagc tgttcgaacg tatctacagc     300
acggatctgg gtcgcatgct gctgactagc attgttcgcg gtatcccgtt ctggggtggt     360
agcacgattg acaccgaact gaaggttatc gacactaact gcattaacgt tattcaaccg     420
gatggtagct atcgtagcga agagctgaat ctggtcatca ttggcccgag cgcagacatt     480
atccaattcg agtgcaagag cttggtcac gaggttctga atctgacccg caatggctat     540
ggtagcaccc agtacattcg tttttcgccg gattttacct tcggctttga agagagcctg     600
gaggttgata ccaatccgtt gctgggtgcg ggcaaattcg ctaccgatcc ggctgtcacg     660
ctggcccatc aactgatcta cgcaggccac cgcctgtacg gcattgccat caacccaaac     720
cgtgtgttca aggttaatac gaatgcatac tacgagatga cggcctggga agtcagcttc     780
gaagaactgc gcaccttcgg tggccatgac gctaaattca ttgacagctt gcaagagaat     840
gagttccgtc tgtactacta taacaaattc aaagacattg caagcacgtt gaacaaggcc     900
aaaagcatcg ttggtactac cgcgtcgttg cagtatatga agaatgtgtt taagagaag     960 tacctgctgt ccgaggatac ctccggcaag tttagcgttg ataagctgaa gtttgacaaa    1020
ctgtacaaga tgctgaccga gatttacacc gaggacaact tgtgaaatt cttcaaagtg    1080
```

```
ttgaatcgta aaacctatct gaattttgac aaagcggttt tcaagattaa catcgtgccg    1140
aaggtgaact acaccatcta tgacggtttt aacctgcgta acaccaacct ggcggcgaac    1200
tttaacggtc agaatacgga aatcaacaac atgaatttca cgaagttgaa gaacttcacg    1260
ggtctgttcg agttctataa gctgctgtgc gtgcgcggta tcatcaccag caaaaccaaa    1320
agcctggaca aaggctacaa caaggcgctg aatgacctgt gcattaaggt aaacaattgg    1380
gatctgttct tttcgccatc cgaagataat tttaccaacg acctgaacaa gggtgaagaa    1440
atcaccagcg atacgaatat tgaagcagcg gaagagaata tcagcctgga tctgatccag    1500
cagtactatc tgacctttaa cttcgacaat gaaccggaga acattagcat tgagaatctg    1560
agcagcgaca ttatcggtca gctggaactg atgccgaata tcgaacgttt cccgaacggc    1620
aaaaagtacg agctggacaa gtacactatg ttccattacc tgcgtgcaca ggagtttgaa    1680
cacggtaaaa gccgtatcgc gctgaccaac agcgttaacg aggccctgct gaacccgagc    1740
cgtgtctata ccttcttcag cagcgactat gttaagaaag tgaacaaagc cactgaggcc    1800
gcgatgttcc tgggctgggt ggaacagctg gtatatgact tcacggacga gacgagcgaa    1860
gtgagcacta ccgacaaaat tgctgatatt accatcatta tcccgtatat tggtccggca    1920
ctgaacattg caacatgct gtacaaagac gattttgtgg gtgccctgat cttctccggt    1980
gccgtgattc tgctggagtt cattccggag attgcgatcc cggtgttggg taccttcgcg    2040
ctggtgtcct acatcgcgaa taaggttctg acgttcaga ccatcgataa cgcgctgtcg    2100
aaacgtaatg aaaaatggga cgaggtttac aaatacattg ttacgaattg gctggcgaaa    2160
gtcaataccc agatcgacct gatccgtaag aaaatgaaag aggcgctgga gaatcaggcg    2220
gaggccacca aagcaattat caactaccaa tacaaccagt acacggaaga agagaagaat    2280
aacattaact tcaatatcga tgatttgagc agcaagctga tgaatctat caacaaagcg    2340 atgatcaata tcaacaagtt tttgaatcag tgtagcgttt cgtacctgat gaatagcatg    2400
attccgtatg gcgtcaaacg tctggaggac ttcgacgcca gcctgaaaga tgcgttgctg    2460
aaatacattt acgacaatcg tggtacgctg attggccaag ttgaccgctt gaaagacaaa    2520
gttaacaata ccctgagcac cgacatccca tttcaactga gcaagtatgt tgataatcaa    2580
cgtctgttga gcactttcac cgagtatatc aaaaacatca tcaatactag cattctgaac    2640
ctgcgttacg agagcaatca tctgattgat ctgagccgtt atgcaagcaa gatcaacatc    2700
ggtagcaagg tcaattttga cccgatcgat aagaaccaga tccagctgtt taatctggaa    2760
tcgagcaaaa ttgaggttat cctgaaaaac gccattgtct acaactccat gtacgagaat    2820
ttctccacca gcttctggat tcgcatcccg aaatacttca acagcattag cctgaacaac    2880
gagtatacta tcatcaactg tatggagaac aacagcggtt ggaaggtgtc tctgaactat    2940
ggtgagatca tttggaccttt gcaggacacc caagagatca agcagcgcgt cgtgttcaag    3000
tactctcaaa tgatcaacat ttccgattac attaatcgtt ggatcttcgt gaccattacg    3060
aataaccgtc tgaataacag caagatttac atcaatggtc gcttgatcga tcagaaaccg    3120
attagcaacc tgggtaatat ccacgcaagc aacaacatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
```

-continued

```
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
ggtgttgaga aaattctgag cgcgttggag atccctgatg tcggtaatct gagccaagtc    3660
gtggttatga agagcaagaa cgaccagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg                 3888
```

<210> SEQ ID NO 4
<211> LENGTH: 1296
<212> TYPE: PRT
<213> ORGANISM: Artificial Sequence
<220> FEATURE:
<223> OTHER INFORMATION: recombinant BoNT/A1 (rBoNT/A1)

<400> SEQUENCE: 4

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190
```

```
Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Gln
210                 215                 220

Leu Ile Tyr Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
            595                 600                 605
```

-continued

```
Gln Leu Val Tyr Asp Phe Thr Asp Glu Thr Ser Glu Val Ser Thr Thr
610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
                850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
                995                 1000                1005

Asp Tyr Ile Asn Arg Trp Ile Phe Val Thr Ile Thr Asn Asn Arg
        1010                1015                1020

Leu Asn Asn Ser Lys Ile Tyr Ile Asn Gly Arg Leu Ile Asp Gln
```

-continued

| | | 1025 | | | 1030 | | | | 1035 | | |
|---|---|---|---|---|---|---|---|---|---|---|---|

Lys Pro Ile Ser Asn Leu Gly Asn Ile His Ala Ser Asn Asn Ile
    1040                        1045                        1050

Met Phe Lys Leu Asp Gly Cys Arg Asp Thr His Arg Tyr Ile Trp
    1055                        1060                        1065

Ile Lys Tyr Phe Asn Leu Phe Asp Lys Glu Leu Asn Glu Lys Glu
    1070                        1075                        1080

Ile Lys Asp Leu Tyr Asp Asn Gln Ser Asn Ser Gly Ile Leu Lys
    1085                        1090                        1095

Asp Phe Trp Gly Asp Tyr Leu Gln Tyr Asp Lys Pro Tyr Tyr Met
    1100                        1105                        1110

Leu Asn Leu Tyr Asp Pro Asn Lys Tyr Val Asp Val Asn Asn Val
    1115                        1120                        1125

Gly Ile Arg Gly Tyr Met Tyr Leu Lys Gly Pro Arg Gly Ser Val
    1130                        1135                        1140

Met Thr Thr Asn Ile Tyr Leu Asn Ser Ser Leu Tyr Arg Gly Thr
    1145                        1150                        1155

Lys Phe Ile Ile Lys Lys Tyr Ala Ser Gly Asn Lys Asp Asn Ile
    1160                        1165                        1170

Val Arg Asn Asn Asp Arg Val Tyr Ile Asn Val Val Val Lys Asn
    1175                        1180                        1185

Lys Glu Tyr Arg Leu Ala Thr Asn Ala Ser Gln Ala Gly Val Glu
    1190                        1195                        1200

Lys Ile Leu Ser Ala Leu Glu Ile Pro Asp Val Gly Asn Leu Ser
    1205                        1210                        1215

Gln Val Val Val Met Lys Ser Lys Asn Asp Gln Gly Ile Thr Asn
    1220                        1225                        1230

Lys Cys Lys Met Asn Leu Gln Asp Asn Asn Gly Asn Asp Ile Gly
    1235                        1240                        1245

Phe Ile Gly Phe His Gln Phe Asn Asn Ile Ala Lys Leu Val Ala
    1250                        1255                        1260

Ser Asn Trp Tyr Asn Arg Gln Ile Glu Arg Ser Ser Arg Thr Leu
    1265                        1270                        1275

Gly Cys Ser Trp Glu Phe Ile Pro Val Asp Asp Gly Trp Gly Glu
    1280                        1285                        1290

Arg Pro Leu
    1295

<210> SEQ ID NO 5
<211> LENGTH: 3888
<212> TYPE: DNA
<213> ORGANISM: Artificial Sequence
<220> FEATURE:
<223> OTHER INFORMATION: nucleotide encoding synthetic cationic BoNT/A
      (CatHN_v1)

<400> SEQUENCE: 5

```
atgccattcg tcaacaagca attcaactac aaagacccag tcaacggcgt cgacatcgca      60
tacatcaaga ttccgaacgc cggtcaaatg cagccggtta aggcttttaa gatccacaac     120
aagatttggg ttatcccgga gcgtgacacc ttcacgaacc cggaagaagg cgatctgaac     180
ccgccaccgg aagcgaagca agtccctgtc agctactacg attcgacgta cctgagcacg     240
gataacgaaa agataacta cctgaaaggt gtgaccaagc tgttcgaacg tatctacagc     300
acggatctgg gtcgcatgct gctgactagc attgttcgcg gtatcccgtt ctggggtggt     360
```

```
agcacgattg acaccgaact gaaggttatc gacactaact gcattaacgt tattcaaccg    420
gatggtagct atcgtagcga agagctgaat ctggtcatca ttggcccgag cgcagacatt    480
atccaattcg agtgcaagag ctttggtcac gaggttctga atctgacccg caatggctat    540
ggtagcaccc agtacattcg tttttcgccg gattttacct tcggctttga agagagcctg    600
gaggttgata ccaatccgtt gctgggtgcg ggcaaattcg ctaccgatcc ggctgtcacg    660
ctggcccatg aactgatcca cgcaggccac cgcctgtacg gcattgccat caacccaaac    720
cgtgtgttca aggttaatac gaatgcatac tacgagatga gcggcctgga agtcagcttc    780
gaagaactgc gcaccttcgg tggccatgac gctaaattca ttgacagctt gcaagagaat    840
gagttccgtc tgtactacta aacaaattc aaagacattg caagcacgtt gaacaaggcc    900
aaaagcatcg ttggtactac cgcgtcgttg cagtatatga agaatgtgtt taaagagaag    960
tacctgctgt ccgaggatac ctccggcaag tttagcgttg ataagctgaa gtttgacaaa   1020
ctgtacaaga tgctgaccga gatttacacc gaggacaact ttgtgaaatt cttcaaagtg   1080
ttgaatcgta aaacctatct gaattttgac aaagcggttt tcaagattaa catcgtgccg   1140
aaggtgaact acaccatcta tgacggtttt aacctgcgta acaccaacct ggcggcgaac   1200
tttaacggtc agaatacgga aatcaacaac atgaatttca cgaagttgaa gaacttcacg   1260
ggtctgttcg agttctataa gctgctgtgc gtgcgcggta tcatcaccag caaaaccaaa   1320
agcctggaca aaggctacaa caaggcgctg aatgacctgt gcattaaggt aaacaattgg   1380
gatctgttct tttcgccatc cgaagataat tttaccaacg acctgaacaa gggtgaagaa   1440
atcaccagcg atacgaatat tgaagcagcg gaagagaata tcagcctgga tctgatccag   1500
cagtactatc tgacctttaa cttcgacaat gaaccggaga acattagcat tgagaatctg   1560
agcagcgaca ttatcggtca gctggaactg atgccgaata tcgaacgttt cccgaacggc   1620
aaaaagtacg agctggacaa gtacactatg ttccattacc tgcgtgcaca ggagttttgaa   1680
cacggtaaac gtcgtatcgc gctgaccaac agcgttaacg aggccctgct gaacccgagc   1740
cgtgtctata ccttcttcag cagcgactat gttaagaaag tgaacaaagc cactgaggcc   1800
gcgatgttcc tgggctgggt ggaacagctg gtatatgact tcacggacga gacgagcgaa   1860
gtgagcacta ccgacaaaat tgctgatatt accatcatta tcccgtatat tggtccggca   1920
ctgaacattg caacatgcg ttacaaacgt cgttttgtgg gtgccctgat cttctccggt   1980
gccgtgattc tgctggagtt cattccggag attgcgatcc cggtgttggg taccttcgcg   2040
ctggtgtcct catcgcgaa taaggttctg acggttcaga ccatcgataa cgcgctgtcg   2100
aaacgtaatg aaaaatggga cgaggtttac aaatacattg ttacgaattg gctggcgaaa   2160
gtcaatccc agatcgacct gatccgtaag aaaatgaaag aggcgctgga gaatcaggcg   2220
gaggccacca agcaattat caactaccaa tacaaccagt acacggaaga agagaagaat   2280
aacattaact tcaatatcga tgatttgagc agcaagctga atgaatctat caacaaagcg   2340
atgatcaata tcaacaagtt tttgaatcag tgtagcgttt cgtacctgat gaatagcatg   2400
attccgtatg gcgtcaaacg tctggaggac ttcgacgcca gcctgaaaga tgcgttgctg   2460
aaatacattt acgacaatcg tggtacgctg attggccaag ttgaccgctt gaaagacaaa   2520
gttaacaata ccctgagccg tgaccgtcca tttcaactga gcaagtatgt tgataatcaa   2580
cgtctgttga gcacttttcac cgagtatatc aaaaacatca tcaatactag cattctgaac   2640
ctgcgttacg agagcaatca tctgattgat ctgagccgtt atgcaagcaa gatcaacatc   2700
ggtagcaagg tcaatttga cccgatcgat aagaaccaga tccagctgtt taatctggaa   2760
```

```
tcgagcaaaa ttgaggttat cctgaaaaac gccattgtct acaactccat gtacgagaat    2820
ttctccacca gcttctggat tcgcatcccg aaatacttca acagcattag cctgaacaac    2880
gagtatacta tcatcaactg tatggagaac aacagcggtt ggaaggtgtc tctgaactat    2940
ggtgagatca tttggacctt gcaggacacc caagagatca agcagcgcgt cgtgttcaag    3000
tactctcaaa tgatcaacat ttccgattac attaatcgtt ggatcttcgt gaccattacg    3060
aataaccgtc tgaataacag caagatttac atcaatggtc gcttgatcga tcagaaaccg    3120
attagcaacc tgggtaatat ccacgcaagc aacaacatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
ggtgttgaga aaattctgag cgcgttggag atccctgatg tcggtaatct gagccaagtc    3660
gtggttatga gagcaagaa cgaccagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg                3888
```

<210> SEQ ID NO 6
<211> LENGTH: 1296
<212> TYPE: PRT
<213> ORGANISM: Artificial Sequence
<220> FEATURE:
<223> OTHER INFORMATION: synthetic cationic BoNT/A (CatHN_v1)

<400> SEQUENCE: 6

```
Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160
```

```
Ile Gln Phe Glu Cys Lys Ser Phe Gly His Glu Val Leu Asn Leu Thr
            165                 170                 175

Arg Asn Gly Tyr Gly Ser Thr Gln Tyr Ile Arg Phe Ser Pro Asp Phe
        180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
        290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
        450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Arg Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
```

-continued

```
                580              585              590
Lys Val Asn Lys Ala Thr Glu Ala Met Phe Leu Gly Trp Val Glu
            595              600              605
Gln Leu Val Tyr Asp Phe Thr Asp Glu Thr Ser Glu Val Ser Thr Thr
        610              615              620
Asp Lys Ile Ala Asp Ile Thr Ile Ile Pro Tyr Ile Gly Pro Ala
625              630              635              640
Leu Asn Ile Gly Asn Met Arg Tyr Lys Arg Arg Phe Val Gly Ala Leu
            645              650              655
Ile Phe Ser Gly Ala Val Ile Leu Leu Glu Phe Ile Pro Glu Ile Ala
            660              665              670
Ile Pro Val Leu Gly Thr Phe Ala Leu Val Ser Tyr Ile Ala Asn Lys
            675              680              685
Val Leu Thr Val Gln Thr Ile Asp Asn Ala Leu Ser Lys Arg Asn Glu
            690              695              700
Lys Trp Asp Glu Val Tyr Lys Tyr Ile Val Thr Asn Trp Leu Ala Lys
705              710              715              720
Val Asn Thr Gln Ile Asp Leu Ile Arg Lys Lys Met Lys Glu Ala Leu
            725              730              735
Glu Asn Gln Ala Glu Ala Thr Lys Ala Ile Ile Asn Tyr Gln Tyr Asn
            740              745              750
Gln Tyr Thr Glu Glu Lys Asn Asn Ile Asn Phe Asn Ile Asp Asp
            755              760              765
Leu Ser Ser Lys Leu Asn Glu Ser Ile Asn Lys Ala Met Ile Asn Ile
            770              775              780
Asn Lys Phe Leu Asn Gln Cys Ser Val Ser Tyr Leu Met Asn Ser Met
785              790              795              800
Ile Pro Tyr Gly Val Lys Arg Leu Glu Asp Phe Asp Ala Ser Leu Lys
            805              810              815
Asp Ala Leu Leu Lys Tyr Ile Tyr Asp Asn Arg Gly Thr Leu Ile Gly
            820              825              830
Gln Val Asp Arg Leu Lys Asp Lys Val Asn Asn Thr Leu Ser Arg Asp
            835              840              845
Arg Pro Phe Gln Leu Ser Lys Tyr Val Asp Asn Gln Arg Leu Leu Ser
850              855              860
Thr Phe Thr Glu Tyr Ile Lys Asn Ile Ile Asn Thr Ser Ile Leu Asn
865              870              875              880
Leu Arg Tyr Glu Ser Asn His Leu Ile Asp Leu Ser Arg Tyr Ala Ser
            885              890              895
Lys Ile Asn Ile Gly Ser Lys Val Asn Phe Asp Pro Ile Asp Lys Asn
            900              905              910
Gln Ile Gln Leu Phe Asn Leu Glu Ser Ser Lys Ile Glu Val Ile Leu
            915              920              925
Lys Asn Ala Ile Val Tyr Asn Ser Met Tyr Glu Asn Phe Ser Thr Ser
            930              935              940
Phe Trp Ile Arg Ile Pro Lys Tyr Phe Asn Ser Ile Ser Leu Asn Asn
945              950              955              960
Glu Tyr Thr Ile Ile Asn Cys Met Glu Asn Asn Ser Gly Trp Lys Val
            965              970              975
Ser Leu Asn Tyr Gly Glu Ile Ile Trp Thr Leu Gln Asp Thr Gln Glu
            980              985              990
Ile Lys Gln Arg Val Val Phe Lys  Tyr Ser Gln Met Ile  Asn Ile Ser
            995              1000             1005
```

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 7
<211> LENGTH: 3888
<212> TYPE: DNA
<213> ORGANISM: Artificial Sequence
<220> FEATURE:
<223> OTHER INFORMATION: nucleotide encoding synthetic cationic BoNT/A
      (CatHN_v2)

<400> SEQUENCE: 7
atgccattcg tcaacaagca attcaactac aaagacccag tcaacggcgt cgacatcgca      60
tacatcaaga ttccgaacgc cggtcaaatg cagccggtta aggcttttaa gatccacaac     120
aagatttggg ttatcccgga gcgtgacacc ttcacgaacc cggaagaagg cgatctgaac     180
ccgccaccgg aagcgaagca agtccctgtc agctactacg attcgacgta cctgagcacg     240

```
gataacgaaa aagataacta cctgaaaggt gtgaccaagc tgttcgaacg tatctacagc    300
acggatctgg gtcgcatgct gctgactagc attgttcgcg gtatcccgtt ctggggtggt    360
agcacgattg acaccgaact gaaggttatc gacactaact gcattaacgt tattcaaccg    420
gatggtagct atcgtagcga agagctgaat ctggtcatca ttggcccgag cgcagacatt    480
atccaattcg agtgcaagag ctttggtcac gaggttctga atctgacccg caatggctat    540
ggtagcaccc agtacattcg ttttcgccg gattttacct tcggctttga agagagcctg     600
gaggttgata ccaatccgtt gctgggtgcg ggcaaattcg ctaccgatcc ggctgtcacg    660
ctggcccatg aactgatcca cgcaggccac cgcctgtacg gcattgccat caacccaaac    720
cgtgtgttca aggttaatac gaatgcatac tacgagatga gcggcctgga agtcagcttc    780
gaagaactgc gcaccttcgg tggccatgac gctaaattca ttgacagctt gcaagagaat    840
gagttccgtc tgtactacta taacaaattc aaagacattg caagcacgtt gaacaaggcc    900
aaaagcatcg ttggtactac cgcgtcgttg cagtatatga agaatgtgtt taaagagaag    960
tacctgctgt ccgaggatac ctccggcaag tttagcgttg ataagctgaa gtttgacaaa   1020
ctgtacaaga tgctgaccga gatttacacc gaggacaact ttgtgaaatt cttcaaagtg   1080
ttgaatcgta aacctatctc gaattttgac aaagcggttt tcaagattaa catcgtgccg   1140
aaggtgaact acaccatcta tgacggtttt aacctgcgta acaccaacct ggcggcgaac   1200
tttaacggtc agaatacgga aatcaacaac atgaatttca cgaagttgaa gaacttcacg   1260
ggtctgttcg agttctataa gctgctgtgc gtgcgcggta tcatcaccag caaaaccaaa   1320
agcctggaca aaggctacaa caaggcgctg aatgacctgt gcattaaggt aaacaattgg   1380
gatctgttct tttcgccatc cgaagataat tttaccaacg acctgaagaa gggtgaagaa   1440
atcaccagcg atacgaatat tgaagcagcg gaagagaata tcagcctgga tctgatccag   1500
cagtactatc tgacctttaa cttcgacaat gaaccggaga acattagcat tgagaatctg   1560
agcagcgaca ttatcggtca gctggaactg atgccgaata tcgaacgttt cccgaacggc   1620
aaaaagtacg agctggacaa gtacactatg ttccattacc tgcgtgcaca ggagtttgaa   1680
cacggtaaaa gccgtatcgc gctgaccaac agcgttaacg aggccctgct gaacccgagc   1740
cgtgtctata ccttcttcag cagcgactat gttaagaaag tgaacaaagc cactaaggcc   1800
gcgatgttcc tgggctgggt ggaacagctg gtatatgact tcacggacga gacgagcgaa   1860
gtgagcacta ccgacaaaat tgctgatatt accatcatta tcccgtatat tggtccggca   1920
ctgaacattg caacatgct gtacaaagac gattttgtgg gtgccctgat cttctccggt    1980
gccgtgattc tgctggagtt cattccggag attgcgatcc cggtgttggg taccttcgcg   2040
ctggtgtcct acatcgcgaa gaaggttctg acggttcaga ccatcgataa cgcgctgtcg   2100
aaacgtaatg aaaaatggga cgaggtttac aaatacattg ttacgaattg gctggcgaaa   2160
gtcaataccc agatcgacct gatccgtaag aaaatgaaag aggcgctgga gaatcaggcg   2220
gaggccacca agcaattat caactaccaa tacaaccagt acacggaaga agagaagaat    2280
aagattaagt caatatcga tgattgagc agcaagctga tgaatctat caacaaagcg    2340 atgatcaata tcaacaagtt tttgaatcag tgtagcgttt cgtacctgat gaatagcatg   2400
attccgtatg gcgtcaaacg tctggaggac ttcgacgcca gcctgaaaga tgcgttgctg   2460
aaatacattt acgacaatcg tggtacgctg aagggccaag ttgaccgctt gaaagacaaa   2520
gttaacaata ccctgagcac cgacatccca tttcaactga gcaagtatgt tgataatcaa   2580
```

```
cgtctgttga gcactttcac cgagtatatc aaaaacatca tcaatactag cattctgaac    2640
ctgcgttacg agagcaatca tctgattgat ctgagccgtt atgcaagcaa gatcaacatc    2700
ggtagcaagg tcaattttga cccgatcgat aagaaccaga tccagctgtt taatctggaa    2760
tcgagcaaaa ttgaggttat cctgaaaaac gccattgtct acaactccat gtacgagaat    2820
ttctccacca gcttctggat tcgcatcccg aaatacttca acagcattag cctgaacaac    2880
gagtatacta tcatcaactg tatggagaac aacagcggtt ggaaggtgtc tctgaactat    2940
ggtgagatca tttggacctt gcaggacacc caagagatca agcagcgcgt cgtgttcaag    3000
tactctcaaa tgatcaacat ttccgattac attaatcgtt ggatcttcgt gaccattacg    3060
aataaccgtc tgaataacag caagatttac atcaatggtc gcttgatcga tcagaaaccg    3120
attagcaacc tggtaatat ccacgcaagc aacaacatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
ggtgttgaga aaattctgag cgcgttggag atccctgatg tcggtaatct gagccaagtc    3660
gtggttatga gagcaagaa cgaccagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg             3888
```

<210> SEQ ID NO 8
<211> LENGTH: 1296
<212> TYPE: PRT
<213> ORGANISM: Artificial Sequence
<220> FEATURE:
<223> OTHER INFORMATION: synthetic cationic BoNT/A (CatHN_v2)

<400> SEQUENCE: 8

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
```

```
              130                 135                 140
Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
                195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Lys Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560
```

```
His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Lys Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Lys Lys
        675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Lys Ile Lys Phe Asn Ile Asp Asp
        755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Lys Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
        850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
        930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975
```

```
Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                1000                1005

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 9
<211> LENGTH: 3888
<212> TYPE: DNA
<213> ORGANISM: Artificial Sequence
<220> FEATURE:
<223> OTHER INFORMATION: nucleotide encoding synthetic cationic BoNT/A
      (CatHN_v3)

<400> SEQUENCE: 9
atgccattcg tcaacaagca attcaactac aaagacccag tcaacggcgt cgacatcgca    60
```

```
tacatcaaga ttccgaacgc cggtcaaatg cagccggtta aggcttttaa gatccacaac    120
aagatttggg ttatcccgga gcgtgacacc ttcacgaacc cggaagaagg cgatctgaac    180
ccgccaccgg aagcgaagca agtccctgtc agctactacg attcgacgta cctgagcacg    240
gataacgaaa aagataacta cctgaaaggt gtgaccaagc tgttcgaacg tatctacagc    300
acggatctgg gtcgcatgct gctgactagc attgttcgcg gtatcccgtt ctggggtggt    360
agcacgattg acaccgaact gaaggttatc gacactaact gcattaacgt tattcaaccg    420
gatggtagct atcgtagcga agagctgaat ctggtcatca ttggcccgag cgcagacatt    480
atccaattcg agtgcaagag cttttggtcac gaggttctga atctgacccg caatggctat    540
ggtagcaccc agtacattcg tttttcgccg gattttacct tcggctttga agagagcctg    600
gaggttgata ccaatccgtt gctgggtgcg ggcaaattcg ctaccgatcc ggctgtcacg    660
ctggcccatg aactgatcca cgcaggccac cgcctgtacg gcattgccat caacccaaac    720
cgtgtgttca aggttaatac gaatgcatac tacgagatga gcggcctgga agtcagcttc    780
gaagaactgc gcaccttcgg tggccatgac gctaaattca ttgacagctt gcaagagaat    840
gagttccgtc tgtactacta taacaaattc aaagacattg caagcacgtt gaacaaggcc    900
aaaagcatcg ttggtactac cgcgtcgttg cagtatatga agaatgtgtt taagagaag    960 tacctgctgt ccgaggatac ctccggcaag tttagcgttg ataagctgaa gtttgacaaa   1020
ctgtacaaga tgctgaccga gatttacacc gaggacaact ttgtgaaatt cttcaaagtg   1080
ttgaatcgta aacctatct gaattttgac aaagcggttt tcaagattaa catcgtgccg   1140
aaggtgaact acaccatcta tgacggtttt aacctgcgta acaccaacct ggcggcgaac   1200
tttaacggtc agaatacgga aatcaacaac atgaatttca cgaagttgaa gaacttcacg   1260
ggtctgttcg agttctataa gctgctgtgc gtgcgcggta tcatcaccag caaaaccaaa   1320
agcctggaca aaggctacaa caaggcgctg aatgacctgt gcattaaggt aaacaattgg   1380
gatctgttct tttcgccatc cgaagataat tttaccaacg acctgaacaa gggtgaagaa   1440
atcaccagcg atacgaatat tgaagcagcg gaagagaata tcagcctgga tctgatccag   1500
cagtactatc tgacctttaa cttcgacaat gaaccggaga acattagcat tgagaatctg   1560
agcagcgaca ttatcggtca gctggaactg atgccgaata tcgaacgttt cccgaacggc   1620
aaaaagtacg agctggacaa gtacactatg ttccattacc tgcgtgcaca ggagtttgaa   1680
cacggtaaaa gccgtatcgc gctgaccaac agcgttaacg aggccctgct gaaaccgagc   1740
cgtgtctata ccttcttcag cagcgactat gttaagaaag tgaacaaagc cactgaggcc   1800
gcgatgttcc tgggctgggt ggaacagctg gtatatgact tcacggacga gacgagcgaa   1860
gtgagcacta ccgacaaaat tgctgatatt accatcatta tcccgtatat tggtccggca   1920
ctgaacattg gcaacatgct gtacaaagac gattttgtgg gtgccctgat cttctccggt   1980
gccgtgattc tgctggagtt cattccggag attgcgatcc cgaagttggg taccttcgcg   2040
ctggtgtcct acaaggcgaa taaggttctg acggttcaga ccatcgataa cgcgctgtcg   2100
aaacgtaatg aaaaatggga cgaggtttac aaatacattg ttacgaattg gctggcgaaa   2160
gtcaataccc agatcgacct gatccgtaag aaaatgaaag aggcgctgga gaatcaggcg   2220
gaggccacca agcaattat caactaccaa tacaaccagt acaaggaaaa agagaagaat   2280
aacattaact tcaatatcga tgatttgagc agcaagctga atgaatctat caacaaagcg   2340
atgatcaata tcaacaagtt tttgaatcag tgtagcgttt cgtacctgat gaatagcatg   2400
attccgtatg gcgtcaaacg tctggaggac ttcgacgcca gcctgaaaga tgcgttgctg   2460
```

```
aaatacattt acgacaatcg tggtacgctg attggccaag ttgaccgctt gaaagacaaa    2520
gttaacaata ccctgagcac cgacatccca tttcaactga gcaagtatgt tgataatcaa    2580
cgtctgttga gcactttcac cgagtatatc aaaaacatca tcaatactag cattctgaac    2640
ctgcgttacg agagcaatca tctgattgat ctgagccgtt atgcaagcaa gatcaacatc    2700
ggtagcaagg tcaattttga cccgatcgat aagaaccaga tccagctgtt taatctggaa    2760
tcgagcaaaa ttgaggttat cctgaaaaac gccattgtct acaactccat gtacgagaat    2820
ttctccacca gcttctggat tcgcatcccg aaatacttca acagcattag cctgaacaac    2880
gagtatacta tcatcaactg tatggagaac acagcggtt ggaaggtgtc tctgaactat     2940
ggtgagatca tttggacctt gcaggacacc caagagatca agcagcgcgt cgtgttcaag    3000
tactctcaaa tgatcaacat ttccgattac attaatcgtt ggatcttcgt gaccattacg    3060
aataaccgtc tgaataacag caagatttac atcaatggtc gcttgatcga tcagaaaccg    3120
attagcaacc tgggtaatat ccacgcaagc aacaacatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
ggtgttgaga aaattctgag cgcgttggag atccctgatg tcggtaatct gagccaagtc    3660
gtggttatga agagcaagaa cgaccagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg              3888
```

<210> SEQ ID NO 10
<211> LENGTH: 1296
<212> TYPE: PRT
<213> ORGANISM: Artificial Sequence
<220> FEATURE:
<223> OTHER INFORMATION: synthetic cationic BoNT/A (CatHN_v3)

<400> SEQUENCE: 10

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110
```

```
Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525
```

-continued

```
Glu Leu Met Pro Asn Ile Glu Arg Phe Pro Asn Gly Lys Lys Tyr Glu
    530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Lys Pro Ser Arg Val Tyr Thr Phe Phe Ser Ser Asp Tyr Val Lys
            580                 585                 590
Lys Val Asn Lys Ala Thr Glu Ala Met Phe Leu Gly Trp Val Glu
        595                 600                 605
Gln Leu Val Tyr Asp Phe Thr Asp Glu Thr Ser Glu Val Ser Thr Thr
    610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Lys Leu Gly Thr Phe Ala Leu Val Ser Tyr Lys Ala Asn Lys
        675                 680                 685
Val Leu Thr Val Gln Thr Ile Asp Asn Ala Leu Ser Lys Arg Asn Glu
    690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                725                 730                 735
Glu Asn Gln Ala Glu Ala Thr Lys Ala Ile Ile Asn Tyr Gln Tyr Asn
            740                 745                 750
Gln Tyr Lys Glu Lys Glu Lys Asn Asn Ile Asn Phe Asn Ile Asp Asp
        755                 760                 765
Leu Ser Ser Lys Leu Asn Glu Ser Ile Asn Lys Ala Met Ile Asn Ile
    770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
                805                 810                 815
Asp Ala Leu Leu Lys Tyr Ile Tyr Asp Asn Arg Gly Thr Leu Ile Gly
            820                 825                 830
Gln Val Asp Arg Leu Lys Asp Lys Val Asn Asn Thr Leu Ser Thr Asp
        835                 840                 845
Ile Pro Phe Gln Leu Ser Lys Tyr Val Asp Asn Gln Arg Leu Leu Ser
    850                 855                 860
Thr Phe Thr Glu Tyr Ile Lys Asn Ile Ile Asn Thr Ser Ile Leu Asn
865                 870                 875                 880
Leu Arg Tyr Glu Ser Asn His Leu Ile Asp Leu Ser Arg Tyr Ala Ser
                885                 890                 895
Lys Ile Asn Ile Gly Ser Lys Val Asn Phe Asp Pro Ile Asp Lys Asn
            900                 905                 910
Gln Ile Gln Leu Phe Asn Leu Glu Ser Ser Lys Ile Glu Val Ile Leu
        915                 920                 925
Lys Asn Ala Ile Val Tyr Asn Ser Met Tyr Glu Asn Phe Ser Thr Ser
    930                 935                 940
Phe Trp Ile Arg Ile Pro Lys Tyr Phe Asn Ser Ile Ser Leu Asn Asn
```

Glu Tyr Thr Ile Ile Asn Cys Met Glu Asn Asn Ser Gly Trp Lys Val
945                 950                 955                 960

Ser Leu Asn Tyr Gly Glu Ile Ile Trp Thr Leu Gln Asp Thr Gln Glu
        965                 970                 975

Ile Lys Gln Arg Val Val Phe Lys Tyr Ser Gln Met Ile Asn Ile Ser
    980                 985                 990

Asp Tyr Ile Asn Arg Trp Ile Phe Val Thr Ile Thr Asn Asn Arg
995                 1000                1005

Leu Asn Asn Ser Lys Ile Tyr Ile Asn Gly Arg Leu Ile Asp Gln
    1010                1015                1020

Lys Pro Ile Ser Asn Leu Gly Asn Ile His Ala Ser Asn Asn Ile
    1025                1030                1035

Met Phe Lys Leu Asp Gly Cys Arg Asp Thr His Arg Tyr Ile Trp
    1040                1045                1050

Ile Lys Tyr Phe Asn Leu Phe Asp Lys Glu Leu Asn Glu Lys Glu
    1055                1060                1065

Ile Lys Asp Leu Tyr Asp Asn Gln Ser Asn Ser Gly Ile Leu Lys
    1070                1075                1080

Asp Phe Trp Gly Asp Tyr Leu Gln Tyr Asp Lys Pro Tyr Tyr Met
    1085                1090                1095

Leu Asn Leu Tyr Asp Pro Asn Lys Tyr Val Asp Val Asn Asn Val
    1100                1105                1110

Gly Ile Arg Gly Tyr Met Tyr Leu Lys Gly Pro Arg Gly Ser Val
    1115                1120                1125

Met Thr Thr Asn Ile Tyr Leu Asn Ser Ser Leu Tyr Arg Gly Thr
    1130                1135                1140

Lys Phe Ile Ile Lys Lys Tyr Ala Ser Gly Asn Lys Asp Asn Ile
    1145                1150                1155

Val Arg Asn Asn Asp Arg Val Tyr Ile Asn Val Val Val Lys Asn
    1160                1165                1170

Lys Glu Tyr Arg Leu Ala Thr Asn Ala Ser Gln Ala Gly Val Glu
    1175                1180                1185

Lys Ile Leu Ser Ala Leu Glu Ile Pro Asp Val Gly Asn Leu Ser
    1190                1195                1200

Gln Val Val Val Met Lys Ser Lys Asn Asp Gln Gly Ile Thr Asn
    1205                1210                1215

Lys Cys Lys Met Asn Leu Gln Asp Asn Asn Gly Asn Asp Ile Gly
    1220                1225                1230

Phe Ile Gly Phe His Gln Phe Asn Asn Ile Ala Lys Leu Val Ala
    1235                1240                1245

Ser Asn Trp Tyr Asn Arg Gln Ile Glu Arg Ser Ser Arg Thr Leu
    1250                1255                1260

Gly Cys Ser Trp Glu Phe Ile Pro Val Asp Asp Gly Trp Gly Glu
    1265                1270                1275

Arg Pro Leu
    1280

<210> SEQ ID NO 11
<211> LENGTH: 2460
<212> TYPE: DNA
<213> ORGANISM: Artificial Sequence
<220> FEATURE:
<223> OTHER INFORMATION: nucleotide encoding synthetic cationic BoNT/E
      light chain (CatLC)

<400> SEQUENCE: 11

```
atgaaaatcg aagaaggtaa actggtaatc tggattaacg gcgataaagg ctataacggt    60
ctcgctgaag tcggtaagaa attcgagaaa gataccggaa ttaaagtcac cgttgagcat   120
ccggataaac tggaagagaa attcccacag gttgcggcaa ctggcgatgg ccctgacatt   180
atcttctggg cacacgaccg ctttggtggc tacgctcaat ctggcctgtt ggctgaaatc   240
accccggaca aagcgttcca ggacaagctg tatccgttta cctgggatgc cgtacgttac   300
aacggcaagc tgattgctta cccgatcgct gttgaagcgt tatcgctgat ttataacaaa   360
gatctgctgc cgaacccgcc aaaaacctgg gaagagatcc cggcgctgga taagaactg    420
aaagcgaaag gtaagagcgc gctgatgttc aacctgcaag aaccgtactt cacctggccg   480
ctgattgctg ctgacggggg ttatgcgttc aagtatgaaa acggcaagta cgacattaaa   540
gacgtgggcg tggataacgc tggcgcgaaa gcgggtctga ccttcctggt tgacctgatt   600
aaaaacaaac acatgaatgc agacaccgat tactccatcg cagaagctgc ctttaataaa   660
ggcgaaacag cgatgaccat caacggcccg tgggcatggt ccaacatcga caccagcaaa   720
gtgaattatg tgtaacggt actgccgacc ttcaagggtc aaccatccaa accgttcgtt    780
ggcgtgctga gcgcaggtat taacgccgcc agtccgaaca aagagctggc aaaagagttc   840
ctcgaaaact atctgctgac tgatgaaggt ctggaagcgg ttaataaaga caaaccgctg   900
ggtgccgtag cgctgaagtc ttacgaggaa gagttggcga agatccacg tattgccgcc    960
actatgaaaa cgcccagaa aggtgaaatc atgccgaaca tcccgcagat gtccgctttc   1020
tggtatgccg tgcgtactgc ggtgatcaac gccgccagcg gtcgtcagac tgtcgatgaa   1080
gccctgaaag acgcgcagac taattcgagc tcgaacaaca caacaataa caataacaac   1140
aacctcggga tcgagggaag gatttcagaa ttcggatcca tgccaaaaat caacagcttt   1200
aattacaatg accctgtaaa cgatcgtacc atcctataca taaagccggg tgggtgtcaa   1260
gagttctaca atctttcaa tattatgaag aatatatgga ttatacctga gcgtaacgtt    1320
attggtacga caccgcaaga ttttcatcca cctacttcgt tgaagaacgg tgactcttcc   1380
tattacgacc ccaattatct ccagtcggat gaagagaagg acagattcct taaaatagta   1440
accaaaatct ttaacaggat taataacaat ctatccggag gtattttgct tgaagagctt   1500
agtaaagcta atccttacct aggtaacgat aatacaccag acaacaagtt tcatataggc   1560
gatgcatccg ccgtggaaat caaatttagc aagggatcac agcatattct cttgcccaac   1620
gttattataa tgggggcgga accagattta tttgaaacaa attcgagtaa tattagcctg   1680
agaaataact atatgccgtc aaaccatggg ttcggtagca tagcgatcgt tacttttcct   1740
cccgaataca gttttcgctt caatgataat agtataaatg agtttatcca agaccccgca   1800
ctcacgctta tgcacgaact catacactct ttacacggcc tgtatggcgc taaggggata   1860
accactacgt gtatcattac tcagcaaaag aaccccattga taacgaacag gaagggcatt   1920
aacatcgagg aatttcttac atttggaggc aacgatctga acattataac tgtcgcacag   1980
tacaatgaca tctataccaa cttactaaat gattatagaa aaatcgcttc taagttatcc   2040
aaggttcaag tctcaaaccc tcaactgaat ccgtataagg acatattcca agagaaatat   2100
ggattagaca aagacgcgtc aggaatctat tcggtaaaca ttaacaaatt cgacgatatt   2160
ttgaagaaac tttacagctt cacggagttc gacttggcca ccaaattcca ggtcaaatgc   2220
cgagagacat acatcggaca gtataagtat ttcaagctgt cgaatctcct gaatgattcc   2280
```

```
atatacaaca ttagtgaggg ttacaatata aataacctaa aggtgaattt ccgaggccaa    2340
aacgccaacc taaatccgcg catcattaaa cccatcacag gacgggggtt agtgaagaaa    2400
ataatccggt ttgcggtcga caagcttgcg gccgcactcg agcaccacca ccaccaccac    2460

<210> SEQ ID NO 12
<211> LENGTH: 820
<212> TYPE: PRT
<213> ORGANISM: Artificial Sequence
<220> FEATURE:
<223> OTHER INFORMATION: synthetic cationic BoNT/E light chain (CatLC)

<400> SEQUENCE: 12

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335
```

```
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Asn
            355                 360                 365
Ser Ser Ser Asn Asn Asn Asn Asn Asn Asn Asn Asn Leu Gly Ile
        370                 375                 380
Glu Gly Arg Ile Ser Glu Phe Gly Ser Met Pro Lys Ile Asn Ser Phe
385                 390                 395                 400
Asn Tyr Asn Asp Pro Val Asn Asp Arg Thr Ile Leu Tyr Ile Lys Pro
                405                 410                 415
Gly Gly Cys Gln Glu Phe Tyr Lys Ser Phe Asn Ile Met Lys Asn Ile
            420                 425                 430
Trp Ile Ile Pro Glu Arg Asn Val Ile Gly Thr Thr Pro Gln Asp Phe
        435                 440                 445
His Pro Pro Thr Ser Leu Lys Asn Gly Asp Ser Ser Tyr Tyr Asp Pro
        450                 455                 460
Asn Tyr Leu Gln Ser Asp Glu Glu Lys Asp Arg Phe Leu Lys Ile Val
465                 470                 475                 480
Thr Lys Ile Phe Asn Arg Ile Asn Asn Asn Leu Ser Gly Gly Ile Leu
                485                 490                 495
Leu Glu Glu Leu Ser Lys Ala Asn Pro Tyr Leu Gly Asn Asp Asn Thr
            500                 505                 510
Pro Asp Asn Lys Phe His Ile Gly Asp Ala Ser Ala Val Glu Ile Lys
        515                 520                 525
Phe Ser Lys Gly Ser Gln His Ile Leu Leu Pro Asn Val Ile Ile Met
    530                 535                 540
Gly Ala Glu Pro Asp Leu Phe Glu Thr Asn Ser Ser Asn Ile Ser Leu
545                 550                 555                 560
Arg Asn Asn Tyr Met Pro Ser Asn His Gly Phe Gly Ser Ile Ala Ile
                565                 570                 575
Val Thr Phe Ser Pro Glu Tyr Ser Phe Arg Phe Asn Asp Asn Ser Ile
            580                 585                 590
Asn Glu Phe Ile Gln Asp Pro Ala Leu Thr Leu Met His Glu Leu Ile
        595                 600                 605
His Ser Leu His Gly Leu Tyr Gly Ala Lys Gly Ile Thr Thr Thr Cys
    610                 615                 620
Ile Ile Thr Gln Gln Lys Asn Pro Leu Ile Thr Asn Arg Lys Gly Ile
625                 630                 635                 640
Asn Ile Glu Glu Phe Leu Thr Phe Gly Gly Asn Asp Leu Asn Ile Ile
                645                 650                 655
Thr Val Ala Gln Tyr Asn Asp Ile Tyr Thr Asn Leu Leu Asn Asp Tyr
            660                 665                 670
Arg Lys Ile Ala Ser Lys Leu Ser Lys Val Gln Val Ser Asn Pro Gln
        675                 680                 685
Leu Asn Pro Tyr Lys Asp Ile Phe Gln Glu Lys Tyr Gly Leu Asp Lys
    690                 695                 700
Asp Ala Ser Gly Ile Tyr Ser Val Asn Ile Asn Lys Phe Asp Asp Ile
705                 710                 715                 720
Leu Lys Lys Leu Tyr Ser Phe Thr Glu Phe Asp Leu Ala Thr Lys Phe
                725                 730                 735
Gln Val Lys Cys Arg Glu Thr Tyr Ile Gly Gln Tyr Lys Tyr Phe Lys
            740                 745                 750
Leu Ser Asn Leu Leu Asn Asp Ser Ile Tyr Asn Ile Ser Glu Gly Tyr
```

```
                755                 760                 765
Asn Ile Asn Asn Leu Lys Val Asn Phe Arg Gly Gln Asn Ala Asn Leu
        770                 775                 780

Asn Pro Arg Ile Ile Lys Pro Ile Thr Gly Arg Gly Leu Val Lys Lys
785                 790                 795                 800

Ile Ile Arg Phe Ala Val Asp Lys Leu Ala Ala Leu Glu His His
                805                 810                 815

His His His His
        820

<210> SEQ ID NO 13
<211> LENGTH: 3888
<212> TYPE: DNA
<213> ORGANISM: Artificial Sequence
<220> FEATURE:
<223> OTHER INFORMATION: nucleotide encoding BoNT/A1

<400> SEQUENCE: 13
```

| | | | |
|---|---|---|---|
| atgccattcg tcaacaagca attcaactac aaagacccag tcaacggcgt cgacatcgca | 60 |
| tacatcaaga ttccgaacgc cggtcaaatg cagccggtta aggcttttaa gatccacaac | 120 |
| aagatttggg ttatcccgga gcgtgacacc ttcacgaacc cggaagaagg cgatctgaac | 180 |
| ccgccaccgg aagcgaagca agtccctgtc agctactacg attcgacgta cctgagcacg | 240 |
| gataacgaaa agataactac cctgaaaggt gtgaccaagc tgttcgaacg tatctacagc | 300 |
| acggatctgg gtcgcatgct gctgactagc attgttcgcg gtatcccgtt ctggggtggt | 360 |
| agcacgattg acaccgaact gaaggttatc gacactaact gcattaacgt tattcaaccg | 420 |
| gatggtagct atcgtagcga agagctgaat ctggtcatca ttggcccgag cgcagacatt | 480 |
| atccaattcg agtgcaagag ctttggtcac gaggttctga atctgacccg caatggctat | 540 |
| ggtagcaccc agtacattcg ttttttcgccg gattttacct tcggctttga agagagcctg | 600 |
| gaggttgata ccaatccgtt gctgggtgcg ggcaaattcg ctaccgatcc ggctgtcacg | 660 |
| ctggcccatg aactgatcca cgcaggccac cgcctgtacg gcattgccat caacccaaac | 720 |
| cgtgtgttca aggttaatac gaatgcatac tacgagatga cggcctggaa gtcagcttc | 780 |
| gaagaactgc gcaccttcgg tggccatgac gctaaattca ttgacagctt gcaagagaat | 840 |
| gagttccgtc tgtactacta taacaaattc aaagacattg caagcacgtt gaacaaggcc | 900 |
| aaaagcatcg ttggtactac cgcgtcgttg cagtatatga agaatgtgtt taaagagaag | 960 |
| tacctgctgt ccgaggatac ctccggcaag tttagcgttg ataagctgaa gtttgacaaa | 1020 |
| ctgtacaaga tgctgaccga gatttacacc gaggacaact tgtgaaaatt cttcaaagtg | 1080 |
| ttgaatcgta aaacctatct gaattttgac aaagcggttt tcaagattaa catcgtgccg | 1140 |
| aaggtgaact acaccatcta tgacggtttt aacctgcgta caccaacctg gcggcgaac | 1200 |
| tttaacggtc agaatacgga aatcaacaac atgaatttca cgaagttgaa gaacttcacg | 1260 |
| ggtctgttcg agttctataa gctgctgtgc gtgcgcggta tcatcaccag caaaaccaaa | 1320 |
| agcctggaca aaggctacaa caaggcgctg aatgacctgt gcattaaggt aaacaattgg | 1380 |
| gatctgttct tttcgccatc cgaagataat tttaccaacg acctgaacaa gggtgaagaa | 1440 |
| atcaccagcg atacgaatat tgaagcagcg aagagaata tcagcctgga tctgatccag | 1500 |
| cagtactatc tgaccttaa cttcgacaat gaaccggaga acattagcat tgagaatctg | 1560 |
| agcagcgaca ttatcggtca gctggaactg atgccgaata tcgaacgttt cccgaacggc | 1620 |
| aaaaagtacg agctggacaa gtacactatg ttccattacc tgcgtgcaca ggagtttgaa | 1680 |

```
cacggtaaaa gccgtatcgc gctgaccaac agcgttaacg aggccctgct gaacccgagc   1740
cgtgtctata ccttcttcag cagcgactat gttaagaaag tgaacaaagc cactgaggcc   1800
gcgatgttcc tgggctgggt ggaacagctg gtatatgact tcacggacga gacgagcgaa   1860
gtgagcacta ccgacaaaat tgctgatatt accatcatta tcccgtatat tggtccggca   1920
ctgaacattg caacatgct gtacaaagac gattttgtgg gtgccctgat cttctccggt   1980
gccgtgattc tgctggagtt cattccggag attgcgatcc cggtgttggg taccttcgcg   2040
ctggtgtcct acatcgcgaa taaggttctg acggttcaga ccatcgataa cgcgctgtcg   2100
aaacgtaatg aaaaatggga cgaggtttac aaatacattg ttacgaattg gctggcgaaa   2160
gtcaataccc agatcgacct gatccgtaag aaaatgaaag aggcgctgga gaatcaggcg   2220
gaggccacca aagcaattat caactaccaa tacaaccagt acacggaaga agagaagaat   2280
aacattaact tcaatatcga tgatttgagc agcaagctga atgaatctat caacaaagcg   2340
atgatcaata tcaacaagtt tttgaatcag tgtagcgttt cgtacctgat gaatagcatg   2400
attccgtatg gcgtcaaacg tctggaggac ttcgacgcca gcctgaaaga tgcgttgctg   2460
aaatacattt acgacaatcg tggtacgctg attggccaag ttgaccgctt gaaagacaaa   2520
gttaacaata ccctgagcac cgacatccca tttcaactga gcaagtatgt tgataatcaa   2580
cgtctgttga gcactttcac cgagtatatc aaaaacatca tcaatactag cattctgaac   2640
ctgcgttacg agagcaatca tctgattgat ctgagccgtt atgcaagcaa gatcaacatc   2700
ggtagcaagg tcaattttga cccgatcgat aagaaccaga tccagctgtt taatctggaa   2760
tcgagcaaaa ttgaggttat cctgaaaaac gccattgtct acaactccat gtacgagaat   2820
ttctccacca gcttctggat tcgcatcccg aaatacttca acagcattag cctgaacaac   2880
gagtatacta tcatcaactg tatggagaac aacagcggtt ggaaggtgtc tctgaactat   2940
ggtgagatca tttggacctt gcaggacacc aagagatca agcagcgcgt cgtgttcaag   3000
tactctcaaa tgatcaacat ttccgattac attaatcgtt ggatcttcgt gaccattacg   3060
aataaccgtc tgaataacag caagatttac atcaatggtc gcttgatcga tcagaaaccg   3120
attagcaacc tgggtaatat ccacgcaagc aacaacatta tgttcaaatt ggacggttgc   3180
cgcgataccc atcgttatat ctggatcaag tatttcaacc tgtttgataa agaactgaat   3240
gagaaggaga tcaaagattt gtatgacaac caatctaaca gcggcatttt gaaggacttc   3300
tggggcgatt atctgcaata cgataagccg tactatatgc tgaacctgta tgatccgaac   3360
aaatatgtgg atgtcaataa tgtgggtatt cgtggttaca tgtatttgaa gggtccgcgt   3420
ggcagcgtta tgacgaccaa catttacctg aactctagcc tgtaccgtgg tacgaaattc   3480
atcattaaga aatatgccag cggcaacaaa gataacattg tgcgtaataa cgatcgtgtc   3540
tacatcaacg tggtcgtgaa gaataaagag taccgtctgg cgaccaacgc ttcgcaggcg   3600
ggtgttgaga aaattctgag cgcgttggag atccctgatg tcggtaatct gagccaagtc   3660
gtggttatga agagcaagaa cgaccagggt atcactaaca agtgcaagat gaacctgcaa   3720
gacaacaatg gtaacgacat cggctttatt ggtttccacc agttcaacaa tattgctaaa   3780
ctggtagcga gcaattggta caatcgtcag attgagcgca gcagccgtac tttgggctgt   3840
agctgggagt ttatcccggt cgatgatggt tgggggcgaac gtccgctg              3888
```

<210> SEQ ID NO 14
<211> LENGTH: 1296
<212> TYPE: PRT

<213> ORGANISM: Artificial Sequence
<220> FEATURE:
<223> OTHER INFORMATION: BoNT/A1

<400> SEQUENCE: 14

Met Pro Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

Asp Asn Glu Lys Asp Asn Tyr Leu Lys Gly Val Thr Lys Leu Phe Glu
85 90 95

Arg Ile Tyr Ser Thr Asp Leu Gly Arg Met Leu Leu Thr Ser Ile Val
100 105 110

Arg Gly Ile Pro Phe Trp Gly Gly Ser Thr Ile Asp Thr Glu Leu Lys
115 120 125

Val Ile Asp Thr Asn Cys Ile Asn Val Ile Gln Pro Asp Gly Ser Tyr
130 135 140

Arg Ser Glu Glu Leu Asn Leu Val Ile Ile Gly Pro Ser Ala Asp Ile
145 150 155 160

Ile Gln Phe Glu Cys Lys Ser Phe Gly His Glu Val Leu Asn Leu Thr
165 170 175

Arg Asn Gly Tyr Gly Ser Thr Gln Tyr Ile Arg Phe Ser Pro Asp Phe
180 185 190

Thr Phe Gly Phe Glu Glu Ser Leu Glu Val Asp Thr Asn Pro Leu Leu
195 200 205

Gly Ala Gly Lys Phe Ala Thr Asp Pro Ala Val Thr Leu Ala His Glu
210 215 220

Leu Ile His Ala Gly His Arg Leu Tyr Gly Ile Ala Ile Asn Pro Asn
225 230 235 240

Arg Val Phe Lys Val Asn Thr Asn Ala Tyr Tyr Glu Met Ser Gly Leu
245 250 255

Glu Val Ser Phe Glu Glu Leu Arg Thr Phe Gly Gly His Asp Ala Lys
260 265 270

Phe Ile Asp Ser Leu Gln Glu Asn Glu Phe Arg Leu Tyr Tyr Tyr Asn
275 280 285

Lys Phe Lys Asp Ile Ala Ser Thr Leu Asn Lys Ala Lys Ser Ile Val
290 295 300

Gly Thr Thr Ala Ser Leu Gln Tyr Met Lys Asn Val Phe Lys Glu Lys
305 310 315 320

Tyr Leu Leu Ser Glu Asp Thr Ser Gly Lys Phe Ser Val Asp Lys Leu
325 330 335

Lys Phe Asp Lys Leu Tyr Lys Met Leu Thr Glu Ile Tyr Thr Glu Asp
340 345 350

Asn Phe Val Lys Phe Phe Lys Val Leu Asn Arg Lys Thr Tyr Leu Asn
355 360 365

Phe Asp Lys Ala Val Phe Lys Ile Asn Ile Val Pro Lys Val Asn Tyr
370 375 380

Thr Ile Tyr Asp Gly Phe Asn Leu Arg Asn Thr Asn Leu Ala Ala Asn

```
              385               390               395               400
       Phe Asn Gly Gln Asn Thr Glu Ile Asn Asn Met Asn Phe Thr Lys Leu
                       405               410               415
       Lys Asn Phe Thr Gly Leu Phe Glu Phe Tyr Lys Leu Leu Cys Val Arg
                       420               425               430
       Gly Ile Ile Thr Ser Lys Thr Lys Ser Leu Asp Lys Gly Tyr Asn Lys
                       435               440               445
       Ala Leu Asn Asp Leu Cys Ile Lys Val Asn Asn Trp Asp Leu Phe Phe
                   450               455               460
       Ser Pro Ser Glu Asp Asn Phe Thr Asn Asp Leu Asn Lys Gly Glu Glu
       465               470               475               480
       Ile Thr Ser Asp Thr Asn Ile Glu Ala Ala Glu Asn Ile Ser Leu
                           485               490               495
       Asp Leu Ile Gln Gln Tyr Tyr Leu Thr Phe Asn Phe Asp Asn Glu Pro
                       500               505               510
       Glu Asn Ile Ser Ile Glu Asn Leu Ser Ser Asp Ile Ile Gly Gln Leu
                       515               520               525
       Glu Leu Met Pro Asn Ile Glu Arg Phe Pro Asn Gly Lys Lys Tyr Glu
                   530               535               540
       Leu Asp Lys Tyr Thr Met Phe His Tyr Leu Arg Ala Gln Glu Phe Glu
       545               550               555               560
       His Gly Lys Ser Arg Ile Ala Leu Thr Asn Ser Val Asn Glu Ala Leu
                       565               570               575
       Leu Asn Pro Ser Arg Val Tyr Thr Phe Phe Ser Ser Asp Tyr Val Lys
                       580               585               590
       Lys Val Asn Lys Ala Thr Glu Ala Ala Met Phe Leu Gly Trp Val Glu
                       595               600               605
       Gln Leu Val Tyr Asp Phe Thr Asp Glu Thr Ser Glu Val Ser Thr Thr
                   610               615               620
       Asp Lys Ile Ala Asp Ile Thr Ile Ile Pro Tyr Ile Gly Pro Ala
       625               630               635               640
       Leu Asn Ile Gly Asn Met Leu Tyr Lys Asp Asp Phe Val Gly Ala Leu
                       645               650               655
       Ile Phe Ser Gly Ala Val Ile Leu Leu Glu Phe Ile Pro Glu Ile Ala
                       660               665               670
       Ile Pro Val Leu Gly Thr Phe Ala Leu Val Ser Tyr Ile Ala Asn Lys
                       675               680               685
       Val Leu Thr Val Gln Thr Ile Asp Asn Ala Leu Ser Lys Arg Asn Glu
                   690               695               700
       Lys Trp Asp Glu Val Tyr Lys Tyr Ile Val Thr Asn Trp Leu Ala Lys
       705               710               715               720
       Val Asn Thr Gln Ile Asp Leu Ile Arg Lys Lys Met Lys Glu Ala Leu
                       725               730               735
       Glu Asn Gln Ala Glu Ala Thr Lys Ala Ile Ile Asn Tyr Gln Tyr Asn
                       740               745               750
       Gln Tyr Thr Glu Glu Glu Lys Asn Asn Ile Asn Phe Asn Ile Asp Asp
                   755               760               765
       Leu Ser Ser Lys Leu Asn Glu Ser Ile Asn Lys Ala Met Ile Asn Ile
                   770               775               780
       Asn Lys Phe Leu Asn Gln Cys Ser Val Ser Tyr Leu Met Asn Ser Met
       785               790               795               800
       Ile Pro Tyr Gly Val Lys Arg Leu Glu Asp Phe Asp Ala Ser Leu Lys
                       805               810               815
```

```
Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
            930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg
1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215
```

```
Gln Val Val Met Lys Ser Lys Asn Asp Gln Gly Ile Thr Asn
    1220            1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 15
<211> LENGTH: 3888
<212> TYPE: DNA
<213> ORGANISM: Artificial Sequence
<220> FEATURE:
<223> OTHER INFORMATION: nucleotide encoding synthetic cationic BoNT/A1
      (Cat-A)

<400> SEQUENCE: 15
atgccattcg tcaacaagca attcaactac aaagacccag tcaacggcgt cgacatcgca      60
tacatcaaga ttccgaacgc cggtcaaatg cagccggtta aggcttttaa gatccacaac     120
aagatttggg ttatcccgga gcgtgacacc ttcacgaacc cggaagaagg cgatctgaac     180
ccgccaccgg aagcgaagca gtccctgtca gctactacg attcgacgta cctgagcacg      240
gataacgaaa agataacta cctgaaaggt gtgaccaagc tgttcgaacg tatctacagc      300
acggatctgg tcgcatgct gctgactagc attgttcgcg gtatcccgtt ctggggtggt      360
agcacgattg acaccgaact gaaggttatc gacactaact gcattaacgt tattcaaccg      420
gatggtagct atcgtagcga agagctgaat ctggtcatca ttggcccgag cgcagacatt      480
atccaattcg agtgcaagag ctttggtcac gaggttctga atctgacccg caatggctat      540
ggtagcaccc agtacattcg tttttcgccg gatttacct tcggctttga agagagcctg      600
gaggttgata ccaatccgtt gctgggtgcg ggcaaattcg ctaccgatcc ggctgtcacg      660
ctggcccatg aactgatcca cgcaggccac cgcctgtacg gcattgccat caacccaaac      720
cgtgtgttca ggttaatac gaatgcatac tacgagatga cgggctgga agtcagcttc      780 gaagaactgc gcaccttcgg tggccatgac gctaaattca ttgacagctt gcaagagaat      840
gagttccgtc tgtactacta taacaaattc aaagacattg caagcacgtt gaacaaggcc      900
aaaagcatcg ttggtactac cgcgtcgttg cagtatatga gaatgtgtt taagagaag      960 tacctgctgt ccgaggatac ctccggcaag tttagcgttg ataagctgaa gtttgacaaa     1020
ctgtacaaga tgctgaccga gatttacacc gaggacaact tgtgaaatt cttcaaagtg     1080 ttgaatcgta aacctatct gaattttgac aaagcggttt tcaagattaa catcgtgccg     1140
aaggtgaact acaccatcta tgacggtttt aacctgcgta caccaacct ggcggcgaac     1200 tttaacggtc agaatacgga aatcaacaac atgaatttca cgaagttgaa gaacttcacg     1260
ggtctgttcg agttctataa gctgctgtgc gtgcgcggta tcatcaccag caaaaccaaa     1320
agcctggaca aaggctacaa caaggcgctg aatgacctgt gcattaaggt aaacaattgg     1380
gatctgttct tttcgccatc cgaagataat tttaccaacg acctgaacaa gggtgaagaa     1440
atcaccagcg atacgaatat tgaagcagcg gaagagaata tcagcctgga tctgatccag     1500
```

-continued

```
cagtactatc tgacctttaa cttcgacaat gaaccggaga acattagcat tgagaatctg    1560
agcagcgaca ttatcggtca gctggaactg atgccgaata tcgaacgttt cccgaacggc    1620
aaaaagtacg agctggacaa gtacactatg ttccattacc tgcgtgcaca ggagtttgaa    1680
cacggtaaaa gccgtatcgc gctgaccaac agcgttaacg aggccctgct gaacccgagc    1740
cgtgtctata ccttcttcag cagcgactat gttaagaaag tgaacaaagc cactgaggcc    1800
gcgatgttcc tgggctgggt ggaacagctg gtatatgact tcacggacga gacgagcgaa    1860
gtgagcacta ccgacaaaat tgctgatatt accatcatta tcccgtatat tggtccggca    1920
ctgaacattg gcaacatgct gtacaaagac gattttgtgg gtgccctgat cttctccggt    1980
gccgtgattc tgctggagtt cattccggag attgcgatcc cggtgttggg taccttcgcg    2040
ctggtgtcct acatcgcgaa taaggttctg acggttcaga ccatcgataa cgcgctgtcg    2100
aaacgtaatg aaaaatggga cgaggtttac aaatacattg ttacgaattg gctggcgaaa    2160
gtcaataccc agatcgacct gatccgtaag aaaatgaaag aggcgctgga gaatcaggcg    2220
gaggccacca aagcaattat caactaccaa tacaaccagt acacgaagaa agagaagaat    2280
aacattaact tcaatatcga tgatttgagc agcaagctga atgaatctat caacaaagcg    2340
atgatcaata tcaacaagtt tttgaatcag tgtagcgttt cgtacctgat gaatagcatg    2400
attccgtatg gcgtcaaacg tctggaggac ttcgacgcca gcctgaaaga tgcgttgctg    2460
aaatacattt acgacaatcg tggtacgctg attggccaag ttgaccgctt gaaagacaaa    2520
gttaacaata ccctgagcac cgacatccca tttcaactga gcaagtatgt tgataatcaa    2580
cgtctgttga gcactttcac cgagtatatc aaaaacatca tcaatactag cattctgaac    2640
ctgcgttacg agagcaagca tctgattgat ctgagccgtt atgctagcaa gatcaacatc    2700
ggtagcaagg tcaattttga cccgatcgat aagaaccaga tccagctgtt taatctggaa    2760
tcgagcaaaa ttgaggttat cctgaaaaag gccattgtct acaactccat gtacgagaat    2820
ttctccacca gcttctggat tcgcatcccg aaatacttca acaagattag cctgaacaac    2880
gagtatacta tcatcaactg tatggagaac aacagcggtt ggaaggtgtc tctgaactat    2940
ggtgagatca tttggacctt gcaggacacc aaagagatca agcagcgcgt cgtgttcaag    3000
tactctcaaa tgatcaacat ttccgattac attaatcgtt ggatcttcgt gaccattacg    3060
aataaccgtc tgaataagag caagatttac atcaatggtc gcttgatcga tcagaaaccg    3120
attagcaacc tgggtaatat ccacgcaagc aacaagatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
ggtgttgaga aaattctgag cgcgttggag atccctgatg tcggtaatct gagccaagtc    3660
gtggttatga agagcaagaa cgacaagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg               3888
```

<210> SEQ ID NO 16
<211> LENGTH: 1296
<212> TYPE: PRT
<213> ORGANISM: Artificial Sequence
<220> FEATURE:
<223> OTHER INFORMATION: synthetic cationic BoNT/A1 (Cat-A)

<400> SEQUENCE: 16
```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365
```

```
Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
        450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
        770                 775                 780
```

```
Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Lys His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
            915                 920                 925

Lys Lys Ala Ile Val Tyr Asn Ser Met Tyr Glu Asn Phe Ser Thr Ser
930                 935                 940

Phe Trp Ile Arg Ile Pro Lys Tyr Phe Asn Lys Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Lys Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg
    1010                1015                1020

Leu Asn Lys Ser Lys Ile Tyr Ile Asn Gly Arg Leu Ile Asp Gln
    1025                1030                1035

Lys Pro Ile Ser Asn Leu Gly Asn Ile His Ala Ser Asn Lys Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
```

```
    1190                1195                1200

Lys Ile  Leu Ser Ala Leu Glu  Ile Pro Asp Val Gly  Asn Leu Ser
    1205                1210                1215

Gln Val  Val Val Met Lys Ser  Lys Asn Asp Lys Gly  Ile Thr Asn
    1220                1225                1230

Lys Cys  Lys Met Asn Leu Gln  Asp Asn Asn Gly Asn  Asp Ile Gly
    1235                1240                1245

Phe Ile  Gly Phe His Gln Phe  Asn Asn Ile Ala Lys  Leu Val Ala
    1250                1255                1260

Ser Asn  Trp Tyr Asn Arg Gln  Ile Glu Arg Ser Ser  Arg Thr Leu
    1265                1270                1275

Gly Cys  Ser Trp Glu Phe Ile  Pro Val Asp Asp Gly  Trp Gly Glu
    1280                1285                1290

Arg Pro  Leu
    1295
```

<210> SEQ ID NO 17
<211> LENGTH: 3888
<212> TYPE: DNA
<213> ORGANISM: Artificial Sequence
<220> FEATURE:
<223> OTHER INFORMATION: nucleotide encoding synthetic cationic BoNT/A1
(Cat-B)

<400> SEQUENCE: 17

```
atgccattcg tcaacaagca attcaactac aaagacccag tcaacggcgt cgacatcgca     60
tacatcaaga ttccgaacgc cggtcaaatg cagccggtta aggcttttaa gatccacaac    120
aagatttggg ttatcccgga gcgtgacacc ttcacgaacc cggaagaagg cgatctgaac    180
ccgccaccgg aagcgaagca agtccctgtc agctactacg attcgacgta cctgagcacg    240
gataacgaaa aagataacta cctgaaaggt gtgaccaagc tgttcgaacg tatctacagc    300
acggatctgg gtcgcatgct gctgactagc attgttcgcg gtatcccgtt ctggggtggt    360
agcacgattg acaccgaact gaaggttatc gacactaact gcattaacgt tattcaaccg    420
gatggtagct atcgtagcga agagctgaat ctggtcatca ttggcccgag cgcagacatt    480
atccaattcg agtgcaagag ctttggtcac gaggttctga atctgacccg caatggctat    540
ggtagcaccc agtacattcg tttttcgccg gattttacct tcggctttga agagagcctg    600
gaggttgata ccaatccgtt gctgggtgcg ggcaaattcg ctaccgatcc ggctgtcacg    660
ctggcccatg aactgatcca cgcaggccac cgcctgtacg gcattgccat caacccaaac    720
cgtgtgttca aggttaatac gaatgcatac tacgagatga gcggcctgga agtcagcttc    780
gaagaactgc gcaccttcgg tggccatgac gctaaattca ttgacagctt gcaagagaat    840
gagttccgtc tgtactacta taacaaattc aaagacattg caagcacgtt gaacaaggcc    900
aaaagcatcg ttggtactac cgcgtcgttg cagtatatga agaatgtgtt taaagagaag    960
tacctgctgt ccgaggatac ctccggcaag tttagcgttg ataagctgaa gtttgacaaa   1020
ctgtacaaga tgctgaccga gatttacacc gaggacaact ttgtgaaatt cttcaaagtg   1080
ttgaatcgta aaacctatct gaattttgac aaagcggttt tcaagattaa catcgtgccg   1140
aaggtgaact acaccatcta tgacggtttt aacctgcgta acaccaacct ggcggcgaac   1200
tttaacggtc agaatacgga aatcaacaac atgaatttca cgaagttgaa gaacttcacg   1260
ggtctgttcg agttctataa gctgctgtgc gtgcgcggta tcatcaccag caaaaccaaa   1320
agcctggaca aaggctacaa caaggcgctg aatgacctgt gcattaaggt aaacaattgg   1380
```

```
gatctgttct tttcgccatc cgaagataat tttaccaacg acctgaacaa gggtgaagaa    1440
atcaccagcg atacgaatat tgaagcagcg gaagagaata tcagcctgga tctgatccag    1500
cagtactatc tgacctttaa cttcgacaat gaaccggaga acattagcat tgagaatctg    1560
agcagcgaca ttatcggtca gctggaactg atgccgaata tcgaacgttt cccgaacggc    1620
aaaaagtacg agctggacaa gtacactatg ttccattacc tgcgtgcaca ggagtttgaa    1680
cacggtaaaa gccgtatcgc gctgaccaac agcgttaacg aggccctgct gaacccgagc    1740
cgtgtctata ccttcttcag cagcgactat gttaagaaag tgaacaaagc cactgaggcc    1800
gcgatgttcc tgggctgggt ggaacagctg gtatatgact tcacgacgga gacgagcgaa    1860
gtgagcacta ccgacaaaat tgctgatatt accatcatta tcccgtatat tggtccggca    1920
ctgaacattg caacatgct gtacaaagac gattttgtgg gtgccctgat cttctccggt    1980
gccgtgattc tgctggagtt cattccggag attgcgatcc cggtgttggg taccttcgcg    2040
ctggtgtcct acatcgcgaa taaggttctg acggttcaga ccatcgataa cgcgctgtcg    2100
aaacgtaatg aaaaatggga cgaggtttac aaatacattg ttacgaattg gctggcgaaa    2160
gtcaataccc agatcgacct gatccgtaag aaaatgaaag aggcgctgga gaatcaggcg    2220
gaggccacca aagcaattat caactaccaa tacaaccagt acacggaaga agagaagaat    2280
aacattaact tcaatatcga tgatttgagc agcaagctga tgaatctat caacaaagcg    2340 atgatcaata tcaacaagtt tttgaatcag tgtagcgttt cgtacctgat gaatagcatg    2400
attccgtatg gcgtcaaacg tctggaggac ttcgacgcca gcctgaaaga tgcgttgctg    2460
aaatacattt acgacaatcg tggtacgctg attggccaag ttgaccgctt gaaagacaaa    2520
gttaacaata ccctgagcac cgacatccca tttcaactga gcaagtatgt tgataatcaa    2580
cgtctgttga gcactttcac cgagtatatc aaaaacatca tcaatactag cattctgaac    2640
ctgcgttacg agagcaatca tctgattgat ctgagccgtt atgctagcaa gatcaacatc    2700
ggtagcaagg tcaattttga cccgatcgat aagaaccaga tccagctgtt taatctggaa    2760
tcgagcaaaa ttgaggttat cctgaaaaag gccattgtct acaactccat gtacgagaat    2820
ttctccacca gcttctggat tcgcatcccg aaatacttca gaagattag cctgaacaac    2880 gagtatacta tcatcaactg tatggagaac aacagcggtt ggaaggtgtc tctgaactat    2940
ggtgagatca tttggacctt gcaggacacc aaagagatca agcagcgcgt cgtgttcaag    3000
tactctcaaa tgatcaacat ttccgattac attaatcgtt ggatcttcgt gaccattacg    3060
aataaccgtc tgaataagag caagatttac atcaatggtc gcttgatcga tcagaaaccg    3120
attagcaacc tgggtaatat ccacgcaagc aacaagatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
ggtgttgaga aaattctgag cgcgttggag atccctgatg tcggtaatct gagccaagtc    3660
gtggttatga agagcaagaa cgacaagggt atcactaaca agtgcaagat gaacctgcaa    3720
```

```
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg                3888
```

<210> SEQ ID NO 18
<211> LENGTH: 1296
<212> TYPE: PRT
<213> ORGANISM: Artificial Sequence
<220> FEATURE:
<223> OTHER INFORMATION: synthetic cationic BoNT/A1 (Cat-B)

<400> SEQUENCE: 18

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335
```

-continued

```
Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
```

```
                755                 760                 765
Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Lys Ala Ile Val Tyr Asn Ser Met Tyr Glu Asn Phe Ser Thr Ser
930                 935                 940

Phe Trp Ile Arg Ile Pro Lys Tyr Phe Lys Lys Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Lys Glu
                980                 985                 990

Ile Lys Gln Arg Val Val Phe Lys  Tyr Ser Gln Met Ile  Asn Ile Ser
                995                 1000                1005

Asp Tyr  Ile Asn Arg Trp Ile  Phe Val Thr Ile Thr  Asn Asn Arg
1010                1015                1020

Leu Asn  Lys Ser Lys Ile Tyr  Ile Asn Gly Arg Leu  Ile Asp Gln
1025                1030                1035

Lys Pro  Ile Ser Asn Leu Gly  Asn Ile His Ala Ser  Asn Lys Ile
1040                1045                1050

Met Phe  Lys Leu Asp Gly Cys  Arg Asp Thr His Arg  Tyr Ile Trp
1055                1060                1065

Ile Lys  Tyr Phe Asn Leu Phe  Asp Lys Glu Leu Asn  Glu Lys Glu
1070                1075                1080

Ile Lys  Asp Leu Tyr Asp Asn  Gln Ser Asn Ser Gly  Ile Leu Lys
1085                1090                1095

Asp Phe  Trp Gly Asp Tyr Leu  Gln Tyr Asp Lys Pro  Tyr Tyr Met
1100                1105                1110

Leu Asn  Leu Tyr Asp Pro Asn  Lys Tyr Val Asp Val  Asn Asn Val
1115                1120                1125

Gly Ile  Arg Gly Tyr Met Tyr  Leu Lys Gly Pro Arg  Gly Ser Val
1130                1135                1140

Met Thr  Thr Asn Ile Tyr Leu  Asn Ser Ser Leu Tyr  Arg Gly Thr
1145                1150                1155

Lys Phe  Ile Ile Lys Lys Tyr  Ala Ser Gly Asn Lys  Asp Asn Ile
1160                1165                1170
```

```
Val Arg Asn Asn Asp Arg Val Tyr Ile Asn Val Val Lys Asn
    1175              1180              1185

Lys Glu Tyr Arg Leu Ala Thr Asn Ala Ser Gln Ala Gly Val Glu
    1190              1195              1200

Lys Ile Leu Ser Ala Leu Glu Ile Pro Asp Val Gly Asn Leu Ser
    1205              1210              1215

Gln Val Val Val Met Lys Ser Lys Asn Asp Lys Gly Ile Thr Asn
    1220              1225              1230

Lys Cys Lys Met Asn Leu Gln Asp Asn Asn Gly Asn Asp Ile Gly
    1235              1240              1245

Phe Ile Gly Phe His Gln Phe Asn Asn Ile Ala Lys Leu Val Ala
    1250              1255              1260

Ser Asn Trp Tyr Asn Arg Gln Ile Glu Arg Ser Ser Arg Thr Leu
    1265              1270              1275

Gly Cys Ser Trp Glu Phe Ile Pro Val Asp Asp Gly Trp Gly Glu
    1280              1285              1290

Arg Pro Leu
    1295

<210> SEQ ID NO 19
<211> LENGTH: 3888
<212> TYPE: DNA
<213> ORGANISM: Artificial Sequence
<220> FEATURE:
<223> OTHER INFORMATION: nucleotide encoding synthetic cationic BoNT/A1
      (Cat-C)

<400> SEQUENCE: 19
atgccattcg tcaacaagca attcaactac aaagacccag tcaacggcgt cgacatcgca      60
tacatcaaga ttccgaacgc cggtcaaatg cagccggtta aggcttttaa gatccacaac     120
aagatttggg ttatcccgga gcgtgacacc ttcacgaacc cggaagaagg cgatctgaac     180
ccgccaccgg aagcgaagca gtccctgtc agctactacg attcgacgta cctgagcacg     240
gataacgaaa agataacta cctgaaaggt gtgaccaagc tgttcgaacg tatctacagc     300
acggatctgg gtcgcatgct gctgactagc attgttcgcg gtatcccgtt ctggggtggt     360
agcacgattg acaccgaact gaaggttatc gacactaact gcattaacgt tattcaaccg     420
gatggtagct atcgtagcga agagctgaat ctggtcatca ttggcccgag cgcagacatt     480
atccaattcg agtgcaagag ctttggtcac gaggttctga atctgacccg caatggctat     540
ggtagcaccc agtacattcg ttttttcgcc g atttttacct tcggctttga agagagcctg     600
gaggttgata ccaatccgtt gctgggtgcg ggcaaattcg ctaccgatcc ggctgtcacg     660
ctggcccatg aactgatcca cgcaggccac cgcctgtacg gcattgccat caacccaaac     720
cgtgtgttca aggttaatac gaatgcatac tacgagatga cggcctgga agtcagcttc     780 gaagaactgc gcaccttcgg tggccatgac gctaaattca ttgacagctt gcaagagaat     840
gagttccgtc tgtactacta taacaaattc aaagacattg caagcacgtt gaacaaggcc     900
aaaagcatcg ttggtactac cgcgtcgttg cagtatatga agaatgtgtt taaagagaag     960
tacctgctgt ccgaggatac ctccggcaag tttagcgttg ataagctgaa gtttgacaaa     1020
ctgtacaaga tgctgaccga gatttacacc gaggacaact tgtgaaaatt cttcaaagtg     1080
ttgaatcgta aacctatct gaattttgac aaagcggttt tcaagattaa catcgtgccg     1140
aaggtgaact acaccatcta tgacggttt aacctgcgta caccaacct ggcggcgaac     1200
```

-continued

```
tttaacggtc agaatacgga aatcaacaac atgaatttca cgaagttgaa gaacttcacg    1260
ggtctgttcg agttctataa gctgctgtgc gtgcgcggta tcatcaccag caaaaccaaa    1320
agcctggaca aaggctacaa caaggcgctg aatgacctgt gcattaaggt aaacaattgg    1380
gatctgttct tttcgccatc cgaagataat tttaccaacg acctgaacaa gggtgaagaa    1440
atcaccagcg atacgaatat tgaagcagcg gaagagaata tcagcctgga tctgatccag    1500
cagtactatc tgacctttaa cttcgacaat gaaccggaga acattagcat tgagaatctg    1560
agcagcgaca ttatcggtca gctggaactg atgccgaata tcgaacgttt cccgaacggc    1620
aaaaagtacg agctggacaa gtacactatg ttccattacc tgcgtgcaca ggagtttgaa    1680
cacggtaaaa gccgtatcgc gctgaccaac agcgttaacg aggccctgct gaacccgagc    1740
cgtgtctata ccttcttcag cagcgactat gttaagaaag tgaacaaagc cactgaggcc    1800
gcgatgttcc tgggctgggt ggaacagctg gtatatgact tcacggacga gacgagcgaa    1860
gtgagcacta ccgacaaaat tgctgatatt accatcatta tcccgtatat tggtccggca    1920
ctgaacattg gcaacatgct gtacaaagac gattttgtgg gtgccctgat cttctccggt    1980
gccgtgattc tgctggagtt cattccggag attgcgatcc cggtgttggg taccttcgcg    2040
ctggtgtcct acatcgcgaa taaggttctg acgttcaga ccatcgataa cgcgctgtcg    2100
aaacgtaatg aaaaatggga cgaggtttac aaatacattg ttacgaattg gctggcgaaa    2160
gtcaatcccc agatcgacct gatccgtaag aaaatgaaag aggcgctgga gaatcaggcg    2220
gaggccacca aagcaattat caactaccaa tacaaccagt acacggaaga agagaagaat    2280
aacattaact tcaatatcga tgatttgagc agcaagctga atgaatctat caacaaagcg    2340
atgatcaata tcaacaagtt tttgaatcag tgtagcgttt cgtacctgat gaatagcatg    2400
attccgtatg gcgtcaaacg tctggaggac ttcgacgcca gcctgaaaga tgcgttgctg    2460
aaatacattt acgacaatcg tggtacgctg attggccaag ttgaccgctt gaaagacaaa    2520
gttaacaata ccctgagcac cgacatccca tttcaactga gcaagtatgt tgataatcaa    2580
cgtctgttga gcactttcac cgagtatatc aaaaacatca tcaatactag cattctgaac    2640
ctgcgttacg agagcaatca tctgattgat ctgagccgtt atgctagcaa gatcaacatc    2700
ggtagcaagg tcaattttga cccgatcgat aagaaccaga tccagctgtt taatctggaa    2760
tcgagcaaaa ttgaggttat cctgaaaaag gccattgtct acaactccat gtacgagaat    2820
ttctccacca gcttctggat tcgcatcccg aaatacttca acaagattag cctgaacaac    2880
gagtatacta tcatcaactg tatggagaac aacagcggtt ggaaggtgtc tctgaactat    2940
ggtgagatca tttggacctt gcaggacacc aaagagatca agcagcgcgt cgtgttcaag    3000
tactctcaaa tgatcaacat ttccgattac attaatcgtt ggatcttcgt gaccattacg    3060
aataaccgtc tgaagaagag caagatttac atcaatggtc gcttgatcga tcagaaaccg    3120
attagcaacc tggtaatat ccacgcaagc aacaagatta tgttcaaatt ggacggttgc    3180 cgcgatacccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
```

-continued

```
ggtgttgaga aaattctgag cgcgttggag atccctgatg tcggtaatct gagccaagtc   3660
gtggttatga agagcaagaa cgacaagggt atcactaaca agtgcaagat gaacctgcaa   3720
gacaacaatg gtaacgacat cggctttatt ggtttccacc agttcaacaa tattgctaaa   3780
ctggtagcga gcaattggta caatcgtcag attgagcgca gcagccgtac tttgggctgt   3840
agctgggagt ttatcccggt cgatgatggt tggggcgaac gtccgctg              3888
```

```
<210> SEQ ID NO 20
<211> LENGTH: 1296
<212> TYPE: PRT
<213> ORGANISM: Artificial Sequence
<220> FEATURE:
<223> OTHER INFORMATION: synthetic cationic BoNT/A1 (Cat-C)

<400> SEQUENCE: 20
```

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys

-continued

```
             305                 310                 315                 320
Tyr Leu Leu Ser Glu Asp Thr Ser Gly Lys Phe Ser Val Asp Lys Leu
                 325                 330                 335
Lys Phe Asp Lys Leu Tyr Lys Met Leu Thr Glu Ile Tyr Thr Glu Asp
                 340                 345                 350
Asn Phe Val Lys Phe Phe Lys Val Leu Asn Arg Lys Thr Tyr Leu Asn
                 355                 360                 365
Phe Asp Lys Ala Val Phe Lys Ile Asn Ile Val Pro Lys Val Asn Tyr
                 370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                 405                 410                 415
Lys Asn Phe Thr Gly Leu Phe Glu Phe Tyr Lys Leu Leu Cys Val Arg
                 420                 425                 430
Gly Ile Ile Thr Ser Lys Thr Lys Ser Leu Asp Lys Gly Tyr Asn Lys
                 435                 440                 445
Ala Leu Asn Asp Leu Cys Ile Lys Val Asn Asn Trp Asp Leu Phe Phe
                 450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                 485                 490                 495
Asp Leu Ile Gln Gln Tyr Tyr Leu Thr Phe Asn Phe Asp Asn Glu Pro
                 500                 505                 510
Glu Asn Ile Ser Ile Glu Asn Leu Ser Ser Asp Ile Ile Gly Gln Leu
                 515                 520                 525
Glu Leu Met Pro Asn Ile Glu Arg Phe Pro Asn Gly Lys Lys Tyr Glu
                 530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                 565                 570                 575
Leu Asn Pro Ser Arg Val Tyr Thr Phe Phe Ser Ser Asp Tyr Val Lys
                 580                 585                 590
Lys Val Asn Lys Ala Thr Glu Ala Ala Met Phe Leu Gly Trp Val Glu
                 595                 600                 605
Gln Leu Val Tyr Asp Phe Thr Asp Glu Thr Ser Glu Val Ser Thr Thr
                 610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                 645                 650                 655
Ile Phe Ser Gly Ala Val Ile Leu Leu Glu Phe Ile Pro Glu Ile Ala
                 660                 665                 670
Ile Pro Val Leu Gly Thr Phe Ala Leu Val Ser Tyr Ile Ala Asn Lys
                 675                 680                 685
Val Leu Thr Val Gln Thr Ile Asp Asn Ala Leu Ser Lys Arg Asn Glu
                 690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                 725                 730                 735
```

```
Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
                850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Lys Ala Ile Val Tyr Asn Ser Met Tyr Glu Asn Phe Ser Thr Ser
930                 935                 940

Phe Trp Ile Arg Ile Pro Lys Tyr Phe Asn Lys Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Lys Glu
                980                 985                 990

Ile Lys Gln Arg Val Val Phe Lys Tyr Ser Gln Met Ile Asn Ile Ser
                995                1000                1005

Asp Tyr Ile Asn Arg Trp Ile Phe Val Thr Ile Thr Asn Asn Arg
                1010                1015                1020

Leu Lys Lys Ser Lys Ile Tyr Ile Asn Gly Arg Leu Ile Asp Gln
                1025                1030                1035

Lys Pro Ile Ser Asn Leu Gly Asn Ile His Ala Ser Asn Lys Ile
                1040                1045                1050

Met Phe Lys Leu Asp Gly Cys Arg Asp Thr His Arg Tyr Ile Trp
                1055                1060                1065

Ile Lys Tyr Phe Asn Leu Phe Asp Lys Glu Leu Asn Glu Lys Glu
                1070                1075                1080

Ile Lys Asp Leu Tyr Asp Asn Gln Ser Asn Ser Gly Ile Leu Lys
                1085                1090                1095

Asp Phe Trp Gly Asp Tyr Leu Gln Tyr Asp Lys Pro Tyr Tyr Met
                1100                1105                1110

Leu Asn Leu Tyr Asp Pro Asn Lys Tyr Val Asp Val Asn Asn Val
                1115                1120                1125

Gly Ile Arg Gly Tyr Met Tyr Leu Lys Gly Pro Arg Gly Ser Val
                1130                1135                1140
```

-continued

```
Met Thr  Thr Asn Ile Tyr Leu  Asn Ser Ser Leu Tyr  Arg Gly Thr
    1145                 1150                 1155

Lys Phe  Ile Ile Lys Lys Tyr  Ala Ser Gly Asn Lys  Asp Asn Ile
    1160                 1165                 1170

Val Arg  Asn Asn Asp Arg Val  Tyr Ile Asn Val Val  Val Lys Asn
    1175                 1180                 1185

Lys Glu  Tyr Arg Leu Ala Thr  Asn Ala Ser Gln Ala  Gly Val Glu
    1190                 1195                 1200

Lys Ile  Leu Ser Ala Leu Glu  Ile Pro Asp Val Gly  Asn Leu Ser
    1205                 1210                 1215

Gln Val  Val Val Met Lys Ser  Lys Asn Asp Lys Gly  Ile Thr Asn
    1220                 1225                 1230

Lys Cys  Lys Met Asn Leu Gln  Asp Asn Asn Gly Asn  Asp Ile Gly
    1235                 1240                 1245

Phe Ile  Gly Phe His Gln Phe  Asn Asn Ile Ala Lys  Leu Val Ala
    1250                 1255                 1260

Ser Asn  Trp Tyr Asn Arg Gln  Ile Glu Arg Ser Ser  Arg Thr Leu
    1265                 1270                 1275

Gly Cys  Ser Trp Glu Phe Ile  Pro Val Asp Asp Gly  Trp Gly Glu
    1280                 1285                 1290

Arg Pro  Leu
    1295
```

<210> SEQ ID NO 21
<211> LENGTH: 3888
<212> TYPE: DNA
<213> ORGANISM: Artificial Sequence
<220> FEATURE:
<223> OTHER INFORMATION: nucleotide encoding synthetic cationic BoNT/A1
(Cat-D)

<400> SEQUENCE: 21

```
atgccattcg tcaacaagca attcaactac aaagacccag tcaacggcgt cgacatcgca     60
tacatcaaga ttccgaacgc cggtcaaatg cagccggtta aggcttttaa gatccacaac    120
aagatttggg ttatcccgga gcgtgacacc ttcacgaacc cggaagaagg cgatctgaac    180
ccgccaccgg aagcgaagca agtccctgtc agctactacg attcgacgta cctgagcacg    240
gataacgaaa aagataacta cctgaaaggt gtgaccaagc tgttcgaacg tatctacagc    300
acggatctgg gtcgcatgct gctgactagc attgttcgcg gtatcccgtt ctggggtggt    360
agcacgattg acaccgaact gaaggttatc gacactaact gcattaacgt tattcaaccg    420
gatggtagct atcgtagcga agagctgaat ctggtcatca ttggcccgag cgcagacatt    480
atccaattcg agtgcaagag ctttggtcac gaggttctga atctgacccg caatggctat    540
ggtagcaccc agtacattcg tttttcgccg gattttacct tcggctttga agagagcctg    600
gaggttgata ccaatccgtt gctgggtgcg ggcaaattcg ctaccgatcc ggctgtcacg    660
ctggcccatg aactgatcca cgcaggccac cgcctgtacg gcattgccat caacccaaac    720
cgtgtgttca aggttaatac gaatgcatac tacgagatga gcggcctgga agtcagcttc    780
gaagaactgc gcaccttcgg tggccatgac gctaaattca ttgacagctt gcaagagaat    840
gagttccgtc tgtactacta taacaaattc aaagacattg caagcacgtt gaacaaggcc    900
aaaagcatcg ttggtactac cgcgtcgttg cagtatatga agaatgtgtt taaagagaag    960
tacctgctgt ccgaggatac ctccggcaag tttagcgttg ataagctgaa gtttgacaaa   1020
ctgtacaaga tgctgaccga gatttacacc gaggacaact ttgtgaaatt cttcaaagtg   1080
```

```
ttgaatcgta aaacctatct gaattttgac aaagcggttt tcaagattaa catcgtgccg   1140
aaggtgaact acaccatcta tgacggtttt aacctgcgta acaccaacct ggcggcgaac   1200
tttaacggtc agaatacgga aatcaacaac atgaatttca cgaagttgaa gaacttcacg   1260
ggtctgttcg agttctataa gctgctgtgc gtgcgcggta tcatcaccag caaaaccaaa   1320
agcctggaca aaggctacaa caaggcgctg aatgacctgt gcattaaggt aaacaattgg   1380
gatctgttct tttcgccatc cgaagataat tttaccaacg acctgaacaa gggtgaagaa   1440
atcaccagcg atacgaatat tgaagcagcg gaagagaata tcagcctgga tctgatccag   1500
cagtactatc tgacctttaa cttcgacaat gaaccggaga acattagcat tgagaatctg   1560
agcagcgaca ttatcggtca gctggaactg atgccgaata tcgaacgttt cccgaacggc   1620
aaaaagtacg agctggacaa gtacactatg ttccattacc tgcgtgcaca ggagtttgaa   1680
cacggtaaaa gccgtatcgc gctgaccaac agcgttaacg aggccctgct gaacccgagc   1740
cgtgtctata ccttcttcag cagcgactat gttaagaaag tgaacaaagc cactgaggcc   1800
gcgatgttcc tgggctgggt ggaacagctg gtatatgact tcacggacga gacgagcgaa   1860
gtgagcacta ccgacaaaat tgctgatatt accatcatta tcccgtatat tggtccggca   1920
ctgaacattg caacatgct gtacaaagac gattttgtgg gtgccctgat cttctccggt   1980
gccgtgattc tgctggagtt cattccggag attgcgatcc cggtgttggg taccttcgcg   2040
ctggtgtcct acatcgcgaa taaggttctg acggttcaga ccatcgataa cgcgctgtcg   2100
aaacgtaatg aaaatggga cgaggtttac aaatacattg ttacgaattg gctggcgaaa   2160
gtcaataccc agatcgacct gatccgtaag aaaatgaaag aggcgctgga gaatcaggcg   2220
gaggccacca aagcaattat caactaccaa tacaaccagt acacggaaga agagaagaat   2280
aacattaact tcaatatcga tgatttgagc agcaagctga tgaatctat caacaaagcg   2340 atgatcaata tcaacaagtt tttgaatcag tgtagcgttt cgtacctgat gaatagcatg   2400
attccgtatg gcgtcaaacg tctggaggac ttcgacgcca gcctgaaaga tgcgttgctg   2460
aaatacattt acgacaatcg tggtacgctg attggccaag ttgaccgctt gaaagacaaa   2520
gttaacaata ccctgagcac cgacatccca tttcaactga gcaagtatgt tgataatcaa   2580
cgtctgttga gcactttcac cgagtatatc aaaaacatca tcaatactag cattctgaac   2640
ctgcgttacg agagcaatca tctgattgat ctgagccgtt atgcaagcaa gatcaacatc   2700
ggtagcaagg tcaattttga cccgatcgat aagaaccaga tccagctgtt taatctggaa   2760
tcgagcaaaa ttgaggttat cctgaaaaac gccattgtct acaactccat gtacgagaat   2820
ttctccacca gcttctggat tcgcatcccg aaatacttca acagcattag cctgaacaac   2880
gagtatacta tcatcaactg tatggagaac aacagcggtt ggaaggtgtc tctgaactat   2940
ggtgagatca tttggaccct gcaggacacc caagagatca agcagcgcgt cgtgttcaag   3000
tactctcaaa tgatcaacat ttccgattac attaatcgtt ggatcttcgt gaccattacg   3060
aataaccgtc tgaataacag caagatttac atcaatggtc gcttgatcga tcagaaaccg   3120
attagcaacc tgggtaatat ccacgcaagc aacaacatta tgttcaaatt ggacggttgc   3180
cgcgataccc atcgttatat ctggatcaag tatttcaacc tgtttgataa agaactgaat   3240
gagaaggaga tcaaagattt gtatgacaac caatctaaca gcggcatttt gaaggacttc   3300
tggggcgatt atctgcaata cgataagccg tactatatgc tgaacctgta tgatccgaac   3360
aaatatgtgg atgtcaataa tgtgggtatt cgtggttaca tgtatttgaa gggtccgcgt   3420
```

-continued

```
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gcgtaaagag taccgtctgg cgaccaacgc ttcgcaggcg    3600
ggtgttgaga aaattctgag cgcgttggag atccctcgtg tccgtcgtct gagccaagtc    3660
gtggttatga agagcaagaa cgaccagggt atcactaaca agtgcaagat gaacctgcaa    3720
gaccgtcgtg gtaacgacat cggctttatt ggtttccacc agttcaacaa tattgctaaa    3780
ctggtagcga gcaattggta caatcgtcag attgagcgcc gtagccgtcg tttgggctgt    3840
agctgggagt ttatcccggt cgatgatggt tggggcgaac gtccgctg                 3888
```

<210> SEQ ID NO 22
<211> LENGTH: 1296
<212> TYPE: PRT
<213> ORGANISM: Artificial Sequence
<220> FEATURE:
<223> OTHER INFORMATION: synthetic cationic BoNT/A1 (Cat-D)

<400> SEQUENCE: 22

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285
```

```
Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
    690                 695                 700
```

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
                995                 1000                1005

Asp Tyr Ile Asn Arg Trp Ile Phe Val Thr Ile Thr Asn Asn Arg
1010                1015                1020

Leu Asn Asn Ser Lys Ile Tyr Ile Asn Gly Arg Leu Ile Asp Gln
1025                1030                1035

Lys Pro Ile Ser Asn Leu Gly Asn Ile His Ala Ser Asn Asn Ile
1040                1045                1050

Met Phe Lys Leu Asp Gly Cys Arg Asp Thr His Arg Tyr Ile Trp
1055                1060                1065

Ile Lys Tyr Phe Asn Leu Phe Asp Lys Glu Leu Asn Glu Lys Glu
1070                1075                1080

Ile Lys Asp Leu Tyr Asp Asn Gln Ser Asn Ser Gly Ile Leu Lys
1085                1090                1095

Asp Phe Trp Gly Asp Tyr Leu Gln Tyr Asp Lys Pro Tyr Tyr Met
1100                1105                1110

Leu Asn Leu Tyr Asp Pro Asn Lys Tyr Val Asp Val Asn Asn Val

```
            1115                1120                1125

Gly Ile Arg Gly Tyr Met Tyr Leu Lys Gly Pro Arg Gly Ser Val
        1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Lys Arg
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Arg Val Arg Arg Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Arg Arg Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Arg Arg Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 23
<211> LENGTH: 5
<212> TYPE: PRT
<213> ORGANISM: Artificial Sequence
<220> FEATURE:
<223> OTHER INFORMATION: Enterokinase cleavage site

<400> SEQUENCE: 23

Asp Asp Asp Asp Lys
1               5

<210> SEQ ID NO 24
<211> LENGTH: 4
<212> TYPE: PRT
<213> ORGANISM: Artificial Sequence
<220> FEATURE:
<223> OTHER INFORMATION: Factor Xa cleavage site

<400> SEQUENCE: 24

Ile Glu Gly Arg
1

<210> SEQ ID NO 25
<211> LENGTH: 4
<212> TYPE: PRT
<213> ORGANISM: Artificial Sequence
<220> FEATURE:
<223> OTHER INFORMATION: Factor Xa cleavage site

<400> SEQUENCE: 25

Ile Asp Gly Arg
1

<210> SEQ ID NO 26
```

```
<211> LENGTH: 7
<212> TYPE: PRT
<213> ORGANISM: Artificial Sequence
<220> FEATURE:
<223> OTHER INFORMATION: Tobacco Etch virus cleavage site

<400> SEQUENCE: 26

Glu Asn Leu Tyr Phe Gln Gly
1               5

<210> SEQ ID NO 27
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 27

Leu Val Pro Arg Gly Ser
1               5

<210> SEQ ID NO 28
<211> LENGTH: 8
<212> TYPE: PRT
<213> ORGANISM: Artificial Sequence
<220> FEATURE:
<223> OTHER INFORMATION: PreScission cleavage site

<400> SEQUENCE: 28

Leu Glu Val Leu Phe Gln Gly Pro
1               5
```